US009603895B2

(12) United States Patent
Or et al.

(10) Patent No.: US 9,603,895 B2
(45) Date of Patent: Mar. 28, 2017

(54) CYCLOSPORIN ANALOGUES FOR PREVENTING OR TREATING HEPATITIS C INFECTION

(71) Applicant: Enanta Pharmaceuticals, Inc., Watertown, MA (US)

(72) Inventors: Yat Sun Or, Watertown, MA (US); Guoqiang Wang, Belmont, MA (US); Jiang Long, Wayland, MA (US); Xuri Gao, Newton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/843,119

(22) Filed: Sep. 2, 2015

(65) Prior Publication Data
US 2016/0051625 A1 Feb. 25, 2016

Related U.S. Application Data

(63) Continuation of application No. 13/734,074, filed on Jan. 4, 2013, now Pat. No. 9,156,886, which is a continuation of application No. 12/697,215, filed on Jan. 30, 2010, now Pat. No. 8,367,618.

(60) Provisional application No. 61/148,583, filed on Jan. 30, 2009.

(51) Int. Cl.

| A61K 38/00 | (2006.01) |
|---|---|
| C07K 5/00 | (2006.01) |
| C07K 7/00 | (2006.01) |
| C07K 16/00 | (2006.01) |
| C07K 17/00 | (2006.01) |
| A61K 38/13 | (2006.01) |
| A61K 31/7088 | (2006.01) |
| A61K 38/21 | (2006.01) |
| A61K 45/00 | (2006.01) |
| C07K 7/52 | (2006.01) |
| A61K 45/06 | (2006.01) |
| C07K 7/64 | (2006.01) |

(52) U.S. Cl.
CPC .......... *A61K 38/13* (2013.01); *A61K 31/7088* (2013.01); *A61K 38/21* (2013.01); *A61K 45/00* (2013.01); *A61K 45/06* (2013.01); *C07K 7/52* (2013.01); *C07K 7/645* (2013.01)

(58) Field of Classification Search
CPC .... A61K 31/7088; A61K 38/13; A61K 38/21; A61K 45/00; A61K 45/06; C07K 7/52; C07K 7/645
See application file for complete search history.

(56) References Cited

U.S. PATENT DOCUMENTS

| RE40,987 E * | 11/2009 | Wenger | C07K 7/645 424/278.1 |
|---|---|---|---|
| 8,367,618 B2 * | 2/2013 | Or | A61K 38/13 514/20.5 |
| 9,156,886 B2 * | 10/2015 | Or | A61K 38/13 |
| 9,221,878 B2 * | 12/2015 | Or | A61K 38/21 |

OTHER PUBLICATIONS

Muamba et al. New Synthetic Routes to NEtXaa4-Cyclosporin Derivatives as Potential Anti-HIV Drugs. Peptides: The Wave of the Future MichalLebland Richard A. Houghten (Editors) American Peptide Society, 2001, 2 pages.*
Scribner, Andrew, et al., "Synthesis and biological evaluation of [D-lysine )8cydosporin A analogs as potential anti-HVC agents," Bioorganic & Medicinal Chemistry Letters, 20(22):6542-6546, 2010.

* cited by examiner

*Primary Examiner* — Marcela M Cordero Garcia
(74) *Attorney, Agent, or Firm* — Edgar W. Harlan; Carolyn S. Elmore, Esq.; Elmore Patent Law Group, P.C.

(57) ABSTRACT

The present invention relates to cyclosporin analogues having antiviral activity against HCV and useful in the treatment of HCV infections. More particularly, the invention relates to novel cyclosporin analogue compounds, compositions containing such compounds and methods for using the same, as well as processes for making such compounds.

16 Claims, No Drawings

US 9,603,895 B2

CYCLOSPORIN ANALOGUES FOR PREVENTING OR TREATING HEPATITIS C INFECTION

RELATED APPLICATION

This application is a continuation of U.S. application Ser. No. 13/734,074, filed Jan. 4, 2013, now U.S. Pat. No. 9,156,886, which is a continuation application of U.S. application Ser. No. 12/697,215, filed Jan. 30, 2010, now U.S. Pat. No. 8,367,618, which claims the benefit of U.S. Provisional Application No. 61/148,583, filed on Jan. 30, 2009. The entire teachings of the above applications are incorporated herein by reference.

TECHNICAL FIELD

The present invention relates to novel cyclosporin analogues having antiviral activity against HCV and useful in the treatment of HCV infections. More particularly, the invention relates to novel cyclosporin analogue compounds, compositions containing such compounds and methods for using the same, as well as processes for making such compounds.

BACKGROUND OF THE INVENTION

Infection with HCV is a major cause of human liver disease throughout the world. In the U.S., an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the U.S. in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Due to the high degree of variability in the viral surface antigens, existence of multiple viral genotypes, and demonstrated specificity of immunity, the development of a successful vaccine in the near future is unlikely. Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

Cyclosporin A (CsA), a neutral cyclic undecapeptide isolated from the fungus *Tolypocladium injlaturn* and currently marketed as Neoral and sandimmunem (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Cyclosporin A and certain derivatives have been reported as having anti-HCV activity, see Watashi et al., Hepatology, 2003, Volume 38, pp 1282-1288, Nakagawa et al., Biochem. Biophys. Res. Commun. 2004, Volume 3 13, pp 42-7, and Shimotohno and K. Watashi, 2004 American Transplant Congress, Abstract No. 648 (American Journal of Transplantation 2004, Volume 4, Issue s8, Pages 1-653). The authors of the Nakagawa et al. paper state that certain chaperone activities, such as those of cyclophilins, may be crucial for the processing and maturation of the viralproteins and for viral replication. Cyclosporin derivatives having HCV activity are known from International Publication No's. WO 2005/021028, WO 2006/039668, WO 2006/038088, WO 2006/039688, WO 2007/112352, WO 2007/112357, WO 2007/112345 and WO 2007/041631.

A subsequent controlled clinical trial showed that a combination of cyclosporin A with interferon α2b is more effective than interferon monotherapy, especially in patients with high viral loads (Inoue et al., "Combined Interferon α2b nd Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporins for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Debio-025 does possess potent binding affinity for cyclophilin A.

SUMMARY OF THE INVENTION

The present invention relates to cyclosporin analogues represented herein below, pharmaceutical compositions comprising such compounds, and methods for the treatment of viral (particularly hepatitis C viral) infection in a subject in need of such therapy with said compounds.

In its principal embodiment, the present invention provides a compound of formula (I);

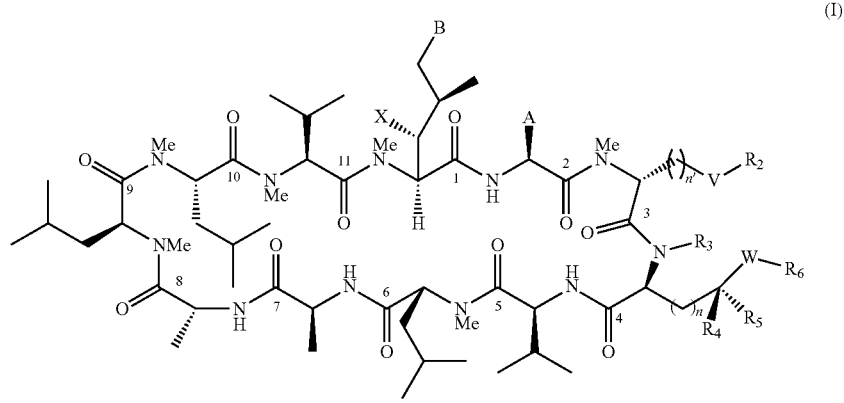

(I)

where
X is OH or OAc;
B is

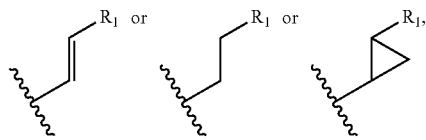

where $R_1$ is selected from:
a) $R_{11}$, where $R_{11}$ is selected from:
 1) Hydrogen;
 2) Deuterium;
 3) $C_1$-$C_8$ alkyl;
 4) Substituted $C_1$-$C_8$ alkyl;
 5) $C_2$-$C_8$ alkenyl;
 6) Substituted $C_2$-$C_8$ alkenyl;
 7) $C_2$-$C_8$ alkynyl;
 8) Substituted $C_2$-$C_8$ alkynyl;
 9) $C_3$-$C_{12}$ cycloalkyl;
 10) Substituted $C_3$-$C_{12}$ cycloalkyl;
 11) Aryl;
 12) Substituted aryl;
 13) Heterocycloalkyl;
 14) Substituted heterocycloalkyl;
 15) Heteroaryl; and
 16) Substituted heteroaryl;
b) —C(O)O$R_{11}$, where $R_{11}$ is as previously defined;
c) —C(O)$R_{11}$, where $R_{11}$ is as previously defined;
d) —C(O)OCH$_2$-T-$R_{12}$, where T is —O— or —S— and $R_{12}$ is selected from:
 1) $C_1$-$C_8$ alkyl;
 2) Substituted $C_1$-$C_8$ alkyl;
 3) $C_2$-$C_8$ alkenyl;
 4) Substituted $C_2$-$C_8$ alkenyl;
 5) $C_2$-$C_8$ alkynyl;
 6) Substituted $C_2$-$C_8$ alkynyl;
 7) $C_3$-$C_{12}$ cycloalkyl;
 8) Substituted $C_3$-$C_{12}$ cycloalkyl;
 9) Aryl;
 10) Substituted aryl;
 11) Heterocycloalkyl;
 12) Substituted heterocycloalkyl;
 13) Heteroaryl; or
 14) Substituted heteroaryl;

e) —C(O)N($R_{13}$)($R_{14}$), where $R_{13}$ and $R_{14}$ are independently selected from $R_{11}$ and $R_{11}$ is as previously defined or $R_{13}$ and $R_{14}$, together with the nitrogen atom to which they are attached, form a substituted or unsubstituted heterocycloalkyl;
f) —C(O)S$R_{11}$, where $R_{11}$ is as previously defined;
g) —C(S)O$R_{11}$, where $R_{11}$ is as previously defined;
h) —C(O)OCH$_2$OC(O)$R_{12}$, where $R_{12}$ is as previously defined;
i) —C(S)S $R_{11}$, where $R_{11}$ is as previously defined;
j) $R_{15}$, where $R_{15}$ is selected from:
 1) -M-$R_{11}$, where $R_{11}$ is as previously defined and M is selected from:
  i. $C_1$-$C_8$ alkyl;
  ii. Substituted $C_1$-$C_8$ alkyl;
  iii. $C_2$-$C_8$ alkenyl;
  iv. Substituted $C_2$-$C_8$ alkenyl;
  v. $C_2$-$C_8$ alkynyl;
  vi. Substituted $C_2$-$C_8$ alkynyl;
  vii. $C_3$-$C_{12}$ cycloalkyl; and
  viii. Substituted $C_3$-$C_{12}$ cycloalkyl;
 2) -M-N$R_{16}R_{11}$, where $R_{16}$ is $R_{11}$ or $R_{16}$ and $R_{11}$ together with the nitrogen atom to which they are attached form a substituted or unsubstituted heterocycloalkyl, M is as previously defined;
 3) -M-S(O)$_m R_{11}$, where m=0, 1, or 2; M and $R_{11}$ are as previously defined;
 4) -M-O$R_{11}$, where M and $R_{11}$ are as previously defined;
 5) -M-C(O)$R_{11}$, where M and $R_{11}$ are as previously defined;
 6) -M-OC(O)$R_{12}$, where M and $R_{12}$ are as previously defined;
 7) -M-OC(O)O $R_{12}$, where M and $R_{12}$ are as previously defined;
 8) -M-N$R_{17}$C(O)$R_{12}$, where $R_{17}$ is $R_{11}$, M and $R_{12}$ are as previously defined;
 9) -MN$R_{17}$C(O)O $R_{12}$, where $R_{17}$, M and $R_{12}$ are as previously defined;
 10) -M-C(O)N$R_{16}R_{11}$, where $R_{16}$, M and $R_{11}$ are as previously defined;

11) -M-C(O)N($R_{16}$)—$OR_{11}$, where $R_{16}$, M and $R_{11}$ are as previously defined;
12) -M-OC(O)$NR_{16}R_{11}$, where $R_{16}$, M and $R_{11}$ are as previously defined;
13) -M-$NR_{17}$C(O)$NR_{16}R_{11}$, where M, $R_{11}$, $R_{17}$ and $R_{16}$ are as previously defined or $R_{16}$ and $R_{11}$ together with the nitrogen atom to which they are attached form a substituted or unsubstituted heterocycloalkyl;
14) -M-C(S)S $R_{11}$, where M and $R_{11}$ are as previously defined;
15) -M-OC(S)S $R_{12}$, where M and $R_{12}$ are as previously defined;
16) -M-$NR_{17}$C(O)S $R_{12}$, where M, $R_{17}$ and $R_{12}$ are as previously defined;
17) -M-SC(O)$NR_{16}R_{11}$, where M, $R_{11}$ and $R_{16}$ are as previously defined or $R_{16}$ and $R_{11}$ together with the nitrogen atom to which they are attached form a substituted or unsubstituted heterocycloalkyl;
18) -M-CH=N—$OR_{11}$, where M and $R_{11}$ are as previously defined;
19) -M-CH=N—$NR_{16}R_{11}$, where M, $R_{11}$ and $R_{16}$ are as previously defined or $R_{16}$ and $R_{11}$ together with the nitrogen atom to which they are attached form a substituted or unsubstituted heterocycloalkyl;

A is ethyl, 1-hydroxyethyl, isopropyl or n-propyl;
W and V are each independently absent, —O—, or —S(O)$_m$—, where m=0, 1, or 2;
$R_2$ is $R_1$, where $R_1$ is as previously defined;
$R_3$ is selected from methyl or ethyl or allyl or propyl;
$R_4$ and $R_5$ are independently selected from: hydrogen or methyl or ethyl or allyl, or propyl, or isopropyl;
$R_6$ is $R_1$, where $R_1$ is as previously defined; and
n and n' are each independently 0, 1, or 2.

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In yet another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of formula (I) as illustrated above, or a pharmaceutically acceptable salt, ester or prodrug thereof.

Representative subgenera of the present invention include:

Compounds of formula (I) which are represented by the formula (IIa) or (IIb);

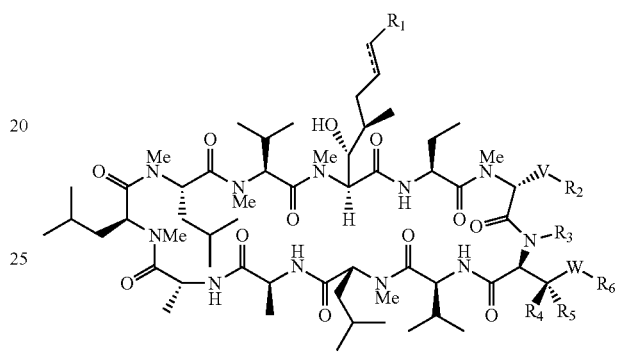

(IIa)

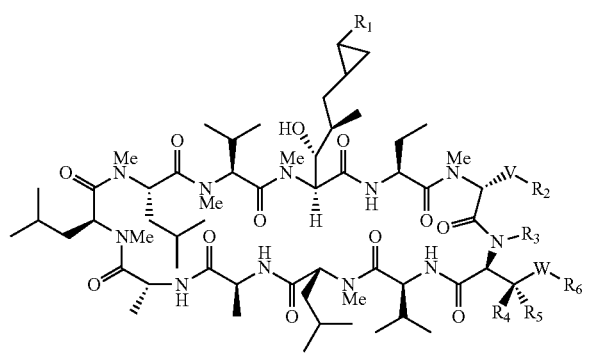

(IIb)

wherein $R_1$, $R_2$, $R_3$, $R_4$, $R_5$, $R_6$, V, and W are as defined above and ═══ represents a single bond or a double bond;

Compounds of formula (I) which are represented by the formula (IIIa) or (IIIb);

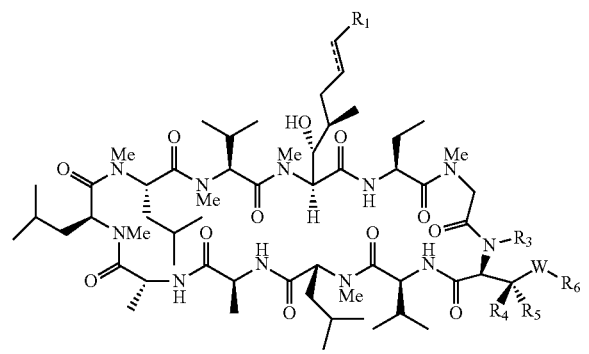

(IIIa)

(IIIb)

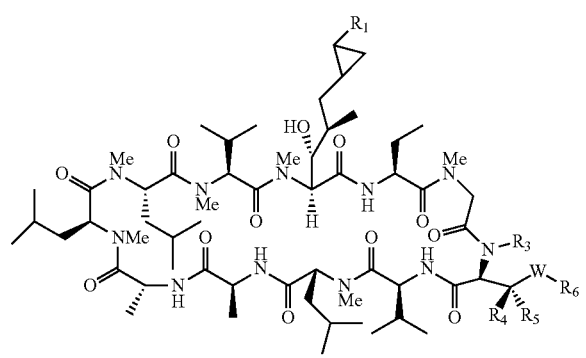

wherein R₁, R₂, R₃, R₄, R₅, R₆, V and W are as defined above and ═ represents a single bond or a double bond.

Compounds of formula (I) which are represented by the formula (IV);

(IV)

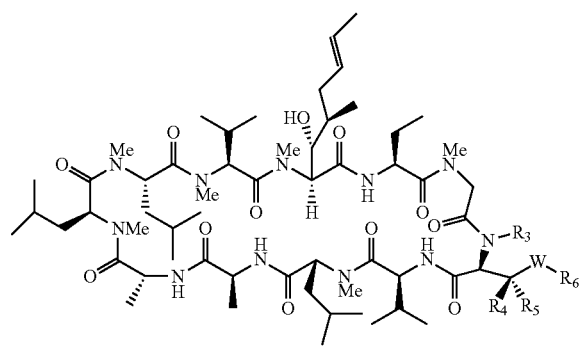

wherein, $R_3$, $R_4$, $R_5$, $R_6$, and W are as defined above.

Compounds of formula (I) which are represented by the formula (V) or (VI):

(V)

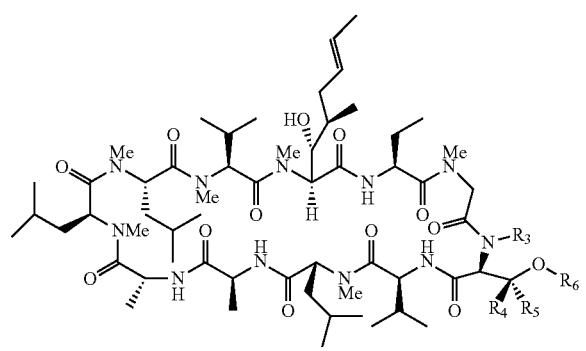

(VI)

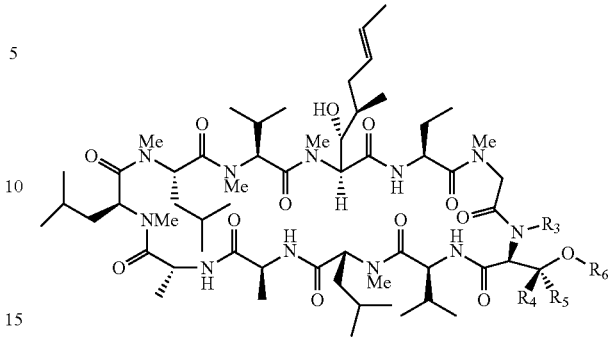

wherein $R_3$, $R_4$, $R_5$ and $R_6$ are as defined above.

Representative species of the present invention include the following compounds of formula (V) or (VI):

Example 1

Compound of Formula V: $R_3=CH_3$, $R_4=H$, $R_5=CH_3$ and $R_6=Ac$;

Example 2

Compound of Formula V: $R_3=CH_3$, $R_4=H$, $R_5=CH_3$ and $R_6=$allyl;

Example 3

Compound of Formula V: $R_3=CH_3$, $R_4=H$, $R_5=CH_3$ and $R_6=$benzyl;

Example 4

Compound of Formula V: $R_3=CH_3$, $R_4=H$, $R_5=CH_3$ and $R_6=$

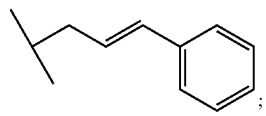
;

Example 5

Compound of Formula V: $R_3=CH_3$, $R_4=H$, $R_5=CH_3$ and $R_6=$

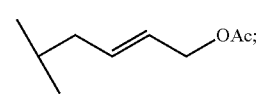

Example 6

Compound of Formula V: $R_3=CH_3$, $R_4=H$, $R_5=CH_3$ and $R_6=$

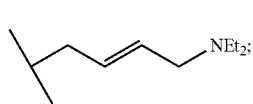

Example 7

Compound of Formula V: $R_3=CH_3$, $R_4=H$, $R_5=CH_3$ and $R_6=$

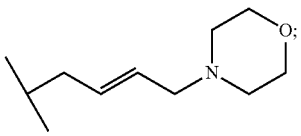

Example 8

Compound of Formula V: $R_3=CH_3$, $R_4=H$, $R_5=CH_3$ and $R_6=$

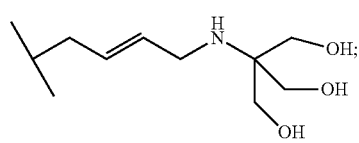

Example 9

Compound of Formula V: $R_3=CH_3$, $R_4=H$, $R_5=CH_3$ and $R_6=$

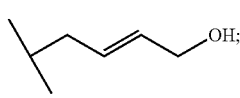

Example 10

Compound of Formula V: $R_3=CH_3$, $R_4=H$, $R_5=CH_3$ and $R_6=$

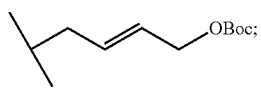

Example 11

Compound of Formula V: $R_3=CH_3$, $R_4=H$, $R_5=CH_3$ and $R_6=$

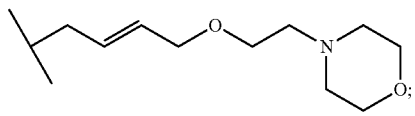 [SMILES: CC(C)C/C=C/COCCN1CCOCC1]

Example 12

Compound of Formula V: $R_3=CH_3$, $R_4=H$, $R_5=CH_3$ and $R_6=$

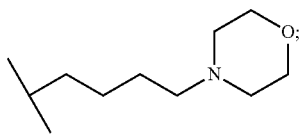

Example 13

Compound of Formula V: $R_3=CH_3$, $R_4=H$, $R_5=CH_3$ and $R_6=$

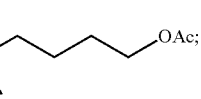

Example 14

Compound of Formula V: $R_3=CH_3$, $R_4=H$, $R_5=CH_3$ and $R_6=$

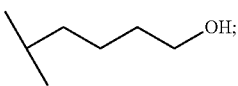

Example 15

Compound of Formula V: $R_3=CH_3$, $R_4=H$, $R_5=CH_3$ and $R_6=$

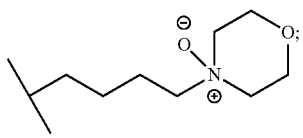

Example 16

Compound of Formula V: $R_3=CH_3$, $R_4=H$, $R_5=CH_3$ and $R_6=$

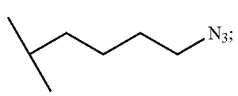

Example 17

Compound of Formula V: $R_3=CH_3$, $R_4=H$, $R_5=CH_3$ and $R_6=$

11

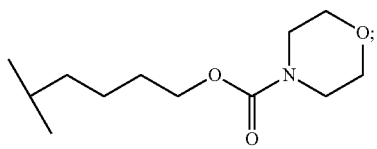 [SMILES: CC(C)CCCCOC(=O)N1CCOCC1]

Example 18

Compound of Formula V: $R_3$=$CH_3$, $R_4$=H, $R_5$=$CH_3$ and $R_6$=

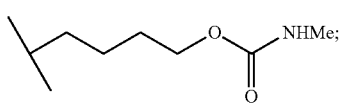

Example 19

Compound of Formula V: $R_3$=$CH_3$, $R_4$=H, $R_5$=$CH_3$ and $R_6$=

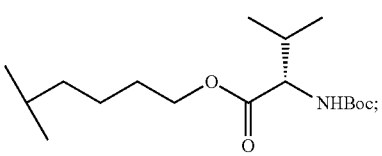 [SMILES: CC(C)CCCCOC(=O)[C@@H](NC(=O)OC(C)(C)C)C(C)C]

Example 20

Compound of Formula V: $R_3$=$CH_3$, $R_4$=H, $R_5$=$CH_3$ and $R_6$=

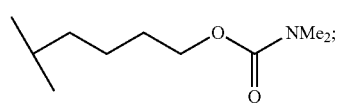

Example 21

Compound of Formula V: $R_3$=$CH_3$, $R_4$=H, $R_5$=$CH_3$ and $R_6$=

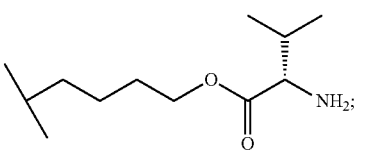

Example 22

Compound of Formula V: $R_3$=$CH_3$, $R_4$=H, $R_5$=$CH_3$ and $R_6$=

12

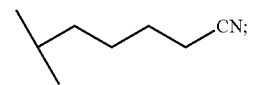

Example 23

Compound of Formula V: $R_3$=$CH_3$, $R_4$=H, $R_5$=$CH_3$ and $R_6$=

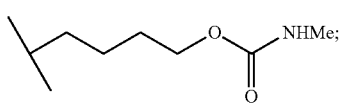

Example 24

Compound of Formula V: $R_3$=$CH_3$, $R_4$=H, $R_5$=$CH_3$ and $R_6$=

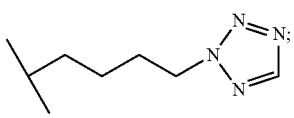

Example 25

Compound of Formula V: $R_3$=$CH_3$, $R_4$=H, $R_5$=$CH_3$ and $R_6$=

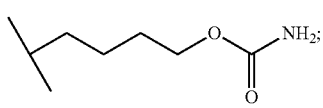

Example 26

Compound of Formula V: $R_3$=$CH_3$, $R_4$=H, $R_5$=$CH_3$ and $R_6$=

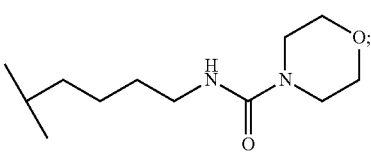 [SMILES: CC(C)CCCCNC(=O)N1CCOCC1]

Example 27

Compound of Formula V: $R_3$=$CH_3$, $R_4$=H, $R_5$=$CH_3$ and $R_6$=

Example 28

Compound of Formula V: $R_3=CH_3$, $R_4=H$, $R_5=CH_3$ and $R_6=$

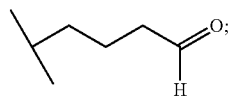

Example 29

Compound of Formula V: $R_3=CH_3$, $R_4=H$, $R_5=CH_3$ and $R_6=$

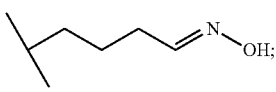

Example 30

Compound of Formula V: $R_3=CH_3$, $R_4=H$, $R_5=CH_3$ and $R_6=$

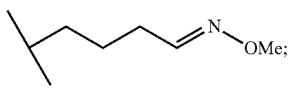

Example 31

Compound of Formula V: $R_3=CH_3$, $R_4=H$, $R_5=CH_3$ and $R_6=$

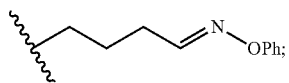

Example 32

Compound of Formula V: $R_3=CH_3$, $R_4=H$, $R_5=CH_3$ and $R_6=$

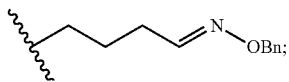 [SMILES: *CCC/C=N/OCc1ccccc1]

Example 33

Compound of Formula V: $R_3=CH_3$, $R_4=H$, $R_5=CH_3$ and $R_6=$

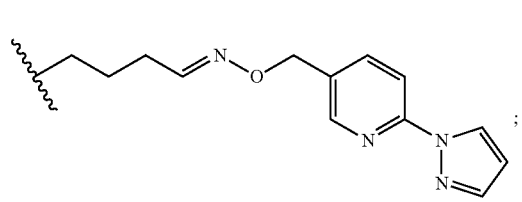 [SMILES: *CCC/C=N/OCc1ccc(-n2cccn2)nc1]

Example 34

Compound of Formula V: $R_3=CH_3$, $R_4=H$, $R_5=CH_3$ and $R_6=$

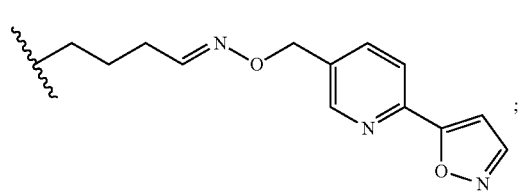 [SMILES: *CCC/C=N/OCc1ccc(-c2ccno2)nc1]

Example 35

Compound of Formula V: $R_3=CH_3$, $R_4=H$, $R_5=CH_3$ and $R_6=$

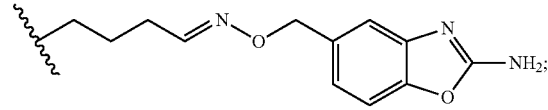 [SMILES: *CCC/C=N/OCc1ccc2oc(N)nc2c1]

Example 36

Compound of Formula V: $R_3=CH_3$, $R_4=H$, $R_5=CH_3$ and $R_6=$

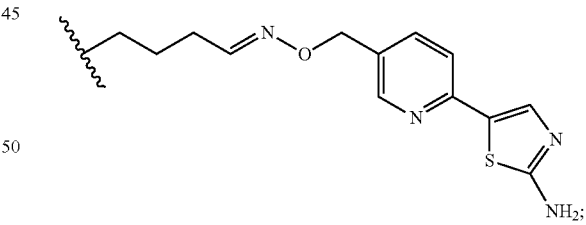

Example 37

Compound of Formula V: $R_3=CH_3$, $R_4=H$, $R_5=CH_3$ and $R_6=$

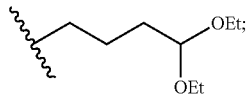 [SMILES: *CCCC(OCC)OCC]

Example 38

Compound of Formula V: $R_3=CH_3$, $R_4=H$, $R_5=CH_3$ and $R_6=$

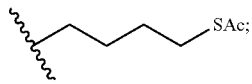

Example 39

Compound of Formula V: $R_3=CH_3$, $R_4=H$, $R_5=CH_3$ and $R_6=$

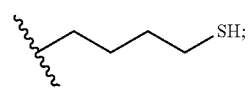 [SMILES: *CCCCS]

Example 40

Compound of Formula V: $R_3=CH_3$, $R_4=H$, $R_5=CH_3$ and $R_6=$

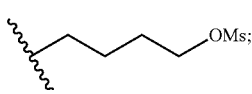

Example 41

Compound of Formula V: $R_3=CH_3$, $R_4=H$, $R_5=CH_3$ and $R_6=$

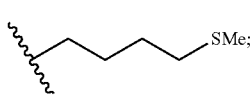 [SMILES: *CCCCSC]

Example 42

Compound of Formula V: $R_3=CH_3$, $R_4=H$, $R_5=CH_3$ and $R_6=$

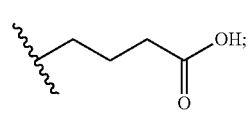 [SMILES: *CCCC(=O)O]

Example 43

Compound of Formula V: $R_3=CH_3$, $R_4=H$, $R_5=CH_3$ and $R_6=$

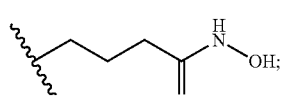

Example 44

Compound of Formula V: $R_3=CH_3$, $R_4=H$, $R_5=CH_3$ and $R_6=$

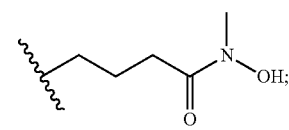 [SMILES: *CCCC(=O)N(C)O]

Example 45

Compound of Formula V: $R_3=CH_3$, $R_4=H$, $R_5=CH_3$ and $R_6=$

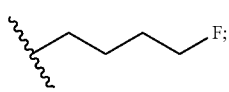 [SMILES: *CCCCF]

Example 46

Compound of Formula V: $R_3=CH_3$, $R_4=H$, $R_5=CH_3$ and $R_6=$

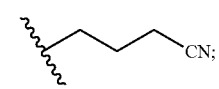 [SMILES: *CCCC#N]

Example 47

Compound of Formula V: $R_3=$allyl, $R_4=H$, $R_5=CH_3$ and $R_6=$

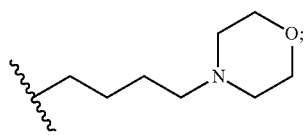 [SMILES: *CCCCN1CCOCC1]

and

Example 48

Compound of Formula V: $R_3=CH_3$, $R_4=CH_3$, $R_5=H$ and $R_6=$allyl;

Example 49

Compound of Formula VI: $R_3=CH_3$, $R_4=H$, $R_5=CH_3$ and $R_6=H$;

Example 50

Compound of Formula VI: $R_3=CH_3$, $R_4=H$, $R_5=CH_3$ and $R_6=$allyl;

Example 51

Compound of Formula VI: $R_3=CH_3$, $R_4=H$, $R_5=CH_3$ and $R_6=$benzyl;

Example 52

Compound of Formula VI: $R_3=CH_3$, $R_4=H$, $R_5=CH_3$ and $R_6=$

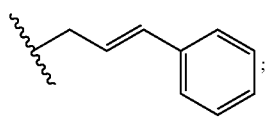 [SMILES: *C/C=C/c1ccccc1]

Example 53

Compound of Formula VI: $R_3=CH_3$, $R_4=H$, $R_5=CH_3$ and $R_6=$

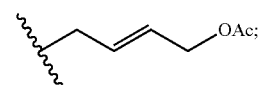 [SMILES: *C/C=C/COC(C)=O]

Example 54

Compound of Formula VI: $R_3=CH_3$, $R_4=H$, $R_5=CH_3$ and $R_6=$

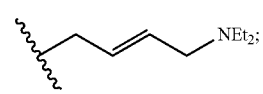

Example 55

Compound of Formula VI: $R_3=CH_3$, $R_4=H$, $R_5=CH_3$ and $R_6=$

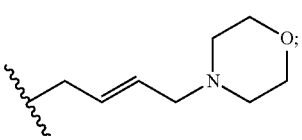 [SMILES: *C/C=C/CN1CCOCC1]

Example 56

Compound of Formula VI: $R_3=CH_3$, $R_4=H$, $R_5=CH_3$ and $R_6=$

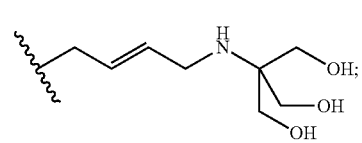 [SMILES: *C/C=C/CNC(CO)(CO)CO]

Example 57

Compound of Formula VI: $R_3=CH_3$, $R_4=H$, $R_5=CH_3$ and $R_6=$

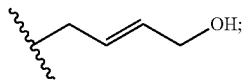 [SMILES: *C/C=C/CO]

Example 58

Compound of Formula VI: $R_3=CH_3$, $R_4=H$, $R_5=CH_3$ and $R_6=$

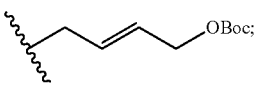

Example 59

Compound of Formula VI: $R_3=CH_3$, $R_4=H$, $R_5=CH_3$ and $R_6=$

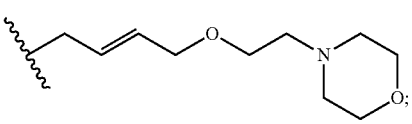 [SMILES: *C/C=C/COCCN1CCOCC1]

Example 60

Compound of Formula VI: $R_3=CH_3$, $R_4=H$, $R_5=CH_3$ and $R_6=$

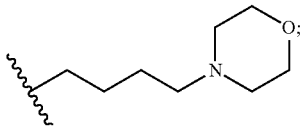 [SMILES: *CCCCN1CCOCC1]

Example 61

Compound of Formula VI: $R_3=CH_3$, $R_4=H$, $R_5=CH_3$ and $R_6=$

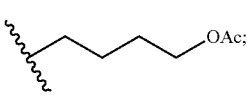 [SMILES: *CCCCOC(C)=O]

Example 62

Compound of Formula VI: $R_3=CH_3$, $R_4=H$, $R_5=CH_3$ and $R_6=$

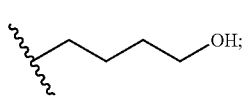 [SMILES: *CCCCO]

Example 63

Compound of Formula VI: $R_3$=$CH_3$, $R_4$=H, $R_5$=$CH_3$ and $R_6$=

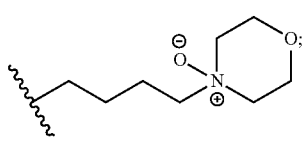 [SMILES: *CCCC[N+]1([O-])CCOCC1]

Example 64

Compound of Formula VI: $R_3$=$CH_3$, $R_4$=H, $R_5$=$CH_3$ and $R_6$=

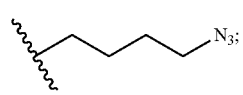 [SMILES: *CCCCN=[N+]=[N-]]

Example 65

Compound of Formula VI: $R_3$=$CH_3$, $R_4$=H, $R_5$=$CH_3$ and $R_6$=

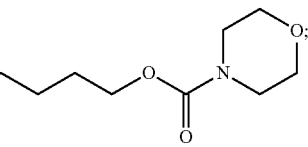

Example 66

Compound of Formula VI: $R_3$=$CH_3$, $R_4$=H, $R_5$=$CH_3$ and $R_6$=

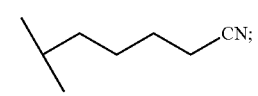

Example 67

Compound of Formula VI: $R_3$=$CH_3$, $R_4$=H, $R_5$=$CH_3$ and $R_6$=

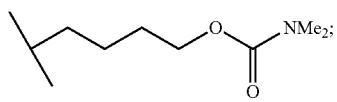

Example 68

Compound of Formula VI: $R_3$=$CH_3$, $R_4$=H, $R_5$=$CH_3$ and $R_6$=

Example 69

Compound of Formula VI: $R_3$=$CH_3$, $R_4$=H, $R_5$=$CH_3$ and $R_6$=

Example 70

Compound of Formula VI: $R_3$=$CH_3$, $R_4$=H, $R_5$=$CH_3$ and $R_6$=

Example 71

Compound of Formula VI: $R_3$=$CH_3$, $R_4$=H, $R_5$=$CH_3$ and $R_6$=

Example 72

Compound of Formula VI: $R_3$=$CH_3$, $R_4$=H, $R_5$=$CH_3$ and $R_6$=

Example 73

Compound of Formula VI: $R_3$=$CH_3$, $R_4$=H, $R_5$=$CH_3$ and $R_6$=

21

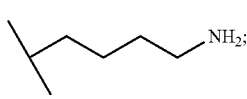

Example 74

Compound of Formula VI: $R_3=CH_3$, $R_4=H$, $R_5=CH_3$ and $R_6=$

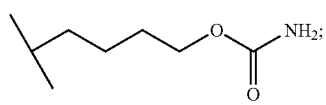

Example 75

Compound of Formula VI: $R_3=CH_3$, $R_4=H$, $R_5=CH_3$ and $R_6=$

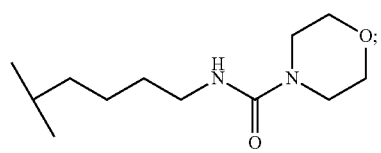 [SMILES: CC(C)CCCCNC(=O)N1CCOCC1]

Example 76

Compound of Formula VI: $R_3=CH_3$, $R_4=H$, $R_5=CH_3$ and $R_6=$

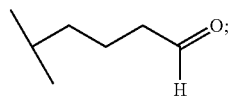

Example 77

Compound of Formula VI: $R_3=CH_3$, $R_4=H$, $R_5=CH_3$ and $R_6=$

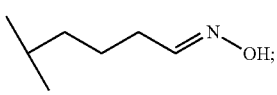

Example 78

Compound of Formula VI: $R_3=CH_3$, $R_4=H$, $R_5=CH_3$ and $R_6=$

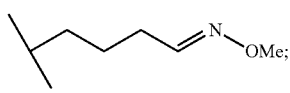

22

Example 79

Compound of Formula VI: $R_3=CH_3$, $R_4=H$, $R_5=CH_3$ and $R_6=$

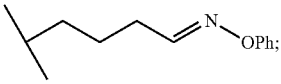

Example 80

Compound of Formula VI: $R_3=CH_3$, $R_4=H$, $R_5=CH_3$ and $R_6=$

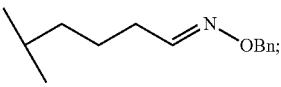 [SMILES: CC(C)CCC/C=N/OCc1ccccc1]

Example 81

Compound of Formula VI: $R_3=CH_3$, $R_4=H$, $R_5=CH_3$ and $R_6=$

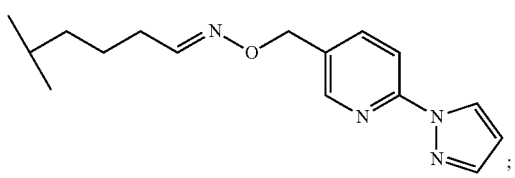 [SMILES: CC(C)CCC/C=N/OCc1ccc(-n2cccn2)nc1]

Example 82

Compound of Formula VI: $R_3=CH_3$, $R_4=H$, $R_5=CH_3$ and $R_6=$

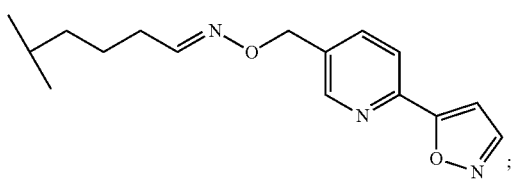 [SMILES: CC(C)CCC/C=N/OCc1ccc(-c2ccno2)nc1]

Example 83

Compound of Formula VI: $R_3=CH_3$, $R_4=H$, $R_5=CH_3$ and $R_6=$

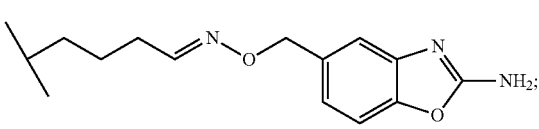 [SMILES: CC(C)CCC/C=N/OCc1ccc2oc(N)nc2c1]

Example 84

Compound of Formula VI: $R_3$=CH$_3$, $R_4$=H, $R_5$=CH$_3$ and $R_6$=

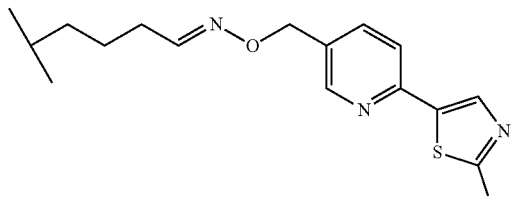

Example 85

Compound of Formula VI: $R_3$=CH$_3$, $R_4$=H, $R_5$=CH$_3$ and $R_6$=

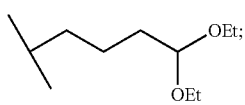

Example 86

Compound of Formula VI: $R_3$=CH$_3$, $R_4$=H, $R_5$=CH$_3$ and $R_6$=

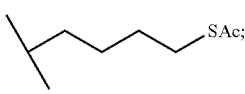

Example 87

Compound of Formula VI: $R_3$=CH$_3$, $R_4$=H, $R_5$=CH$_3$ and $R_6$=

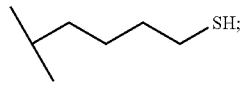

Example 88

Compound of Formula VI: $R_3$=CH$_3$, $R_4$=H, $R_5$=CH$_3$ and $R_6$=

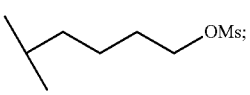

Example 89

Compound of Formula VI: $R_3$=CH$_3$, $R_4$=H, $R_5$=CH$_3$ and $R_6$=

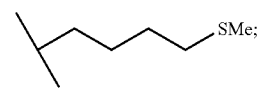

Example 90

Compound of Formula VI: $R_3$=CH$_3$, $R_4$=H, $R_5$=CH$_3$ and $R_6$=

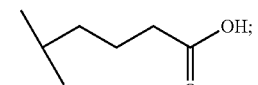

Example 91

Compound of Formula VI: $R_3$=CH$_3$, $R_4$=H, $R_5$=CH$_3$ and $R_6$=

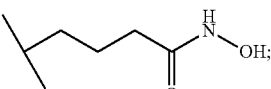

Example 92

Compound of Formula VI: $R_3$=CH$_3$, $R_4$=H, $R_5$=CH$_3$ and $R_6$=

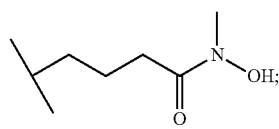

Example 93

Compound of Formula VI: $R_3$=CH$_3$, $R_4$=H, $R_5$=CH$_3$ and $R_6$=

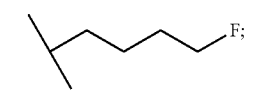

Example 94

Compound of Formula VI: $R_3$=CH$_3$, $R_4$=H, $R_5$=CH$_3$ and $R_6$=

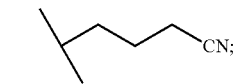

Example 95

Compound of Formula VI: $R_3$=Me, $R_4$=H, $R_5$=$CH_3$ and $R_6$=

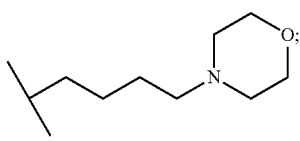

Example 96

Compound of Formula VI: $R_3$=Me, $R_4$=H, $R_5$=$CH_3$ and $R_6$=

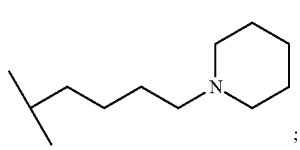

Example 97

Compound of Formula VI: $R_3$=Me, $R_4$=H, $R_5$=$CH_3$ and $R_6$=

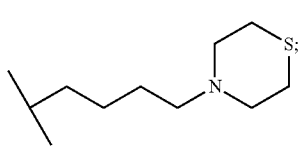

Example 98

Compound of Formula VI: $R_3$=Me, $R_4$=H, $R_5$=$CH_3$ and $R_6$=

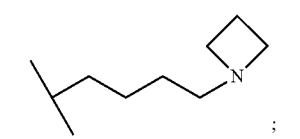

Example 99

Compound of Formula VI: $R_3$=Me, $R_4$=H, $R_5$=$CH_3$ and $R_6$=

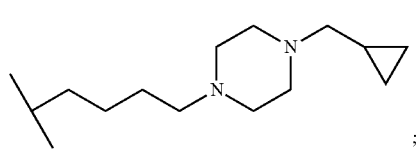 [SMILES: CC(C)CCCCN1CCN(CC2CC2)CC1]

Example 100

Compound of Formula VI: $R_3$=Me, $R_4$=H, $R_5$=$CH_3$ and $R_6$=

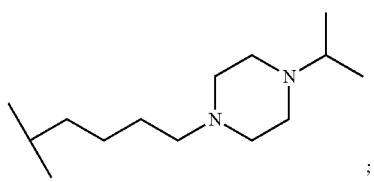 [SMILES: CC(C)CCCCN1CCN(C(C)C)CC1]

Example 101

Compound of Formula VI: $R_3$=Me, $R_4$=H, $R_5$=$CH_3$ and $R_6$=

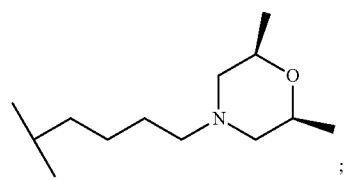

Example 102

Compound of Formula VI: $R_3$=Me, $R_4$=H, $R_5$=$CH_3$ and $R_6$=

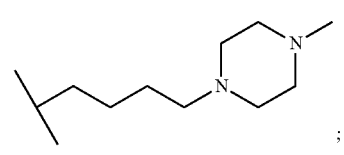

Example 103

Compound of Formula VI: $R_3$=Me, $R_4$=H, $R_5$=$CH_3$ and $R_6$=

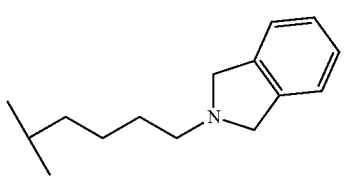

Example 104

Compound of Formula VI: $R_3$=Me, $R_4$=H, $R_5$=$CH_3$ and $R_6$=

27

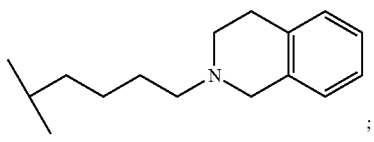 [SMILES: CC(C)CCCCN1CCc2ccccc2C1]

Example 105

Compound of Formula VI: R₃=Me, R₄=H, R₅=CH₃ and R₆=

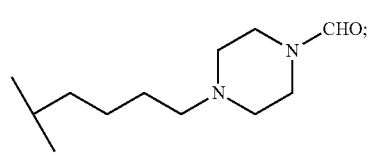

Example 106

Compound of Formula VI: R₃=Me, R₄=H, R₅=CH₃ and R₆=

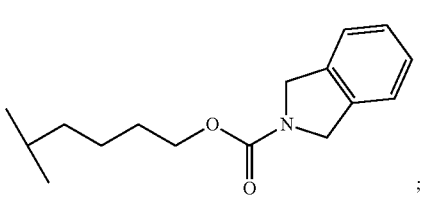 [SMILES: CC(C)CCCCOC(=O)N1Cc2ccccc2C1]

Example 107

Compound of Formula VI: R₃=Me, R₄=H, R₅=CH₃ and R₆=

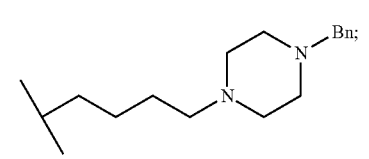 [SMILES: CC(C)CCCCN1CCN(Cc2ccccc2)CC1]

Example 108

Compound of Formula VI: R₃=Me, R₄=H, R₅=CH₃ and R₆=

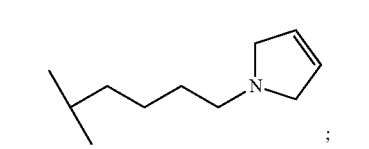

Example 109

Compound of Formula VI: R₃=Me, R₄=H, R₅=CH₃ and R₆=

28

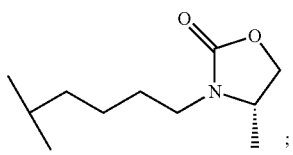

Example 110

Compound of Formula VI: R₃=Me, R₄=H, R₅=CH₃ and R₆=

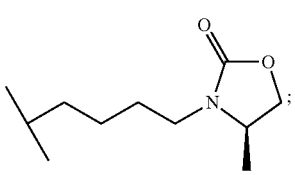

Example 111

Compound of Formula VI: R₃=Me, R₄=H, R₅=CH₃ and R₆=

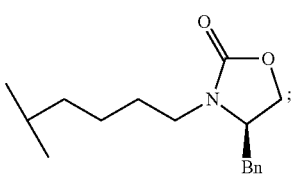 [SMILES: CC(C)CCCCN1C(=O)OC[C@H]1Cc1ccccc1]

Example 112

Compound of Formula VI: R₃=Me, R₄=H, R₅=CH₃ and R₆=

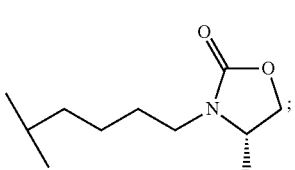

Example 113

Compound of Formula VI: R₃=Me, R₄=H, R₅=CH₃ and R₆=

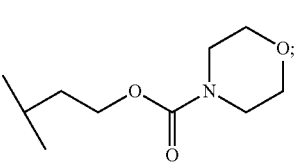

Example 114

Compound of Formula VI: $R_3$=Me, $R_4$=H, $R_5$=CH$_3$ and $R_6$=

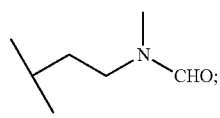

Example 115

Compound of Formula VI: $R_3$=Me, $R_4$=H, $R_5$=CH$_3$ and $R_6$=

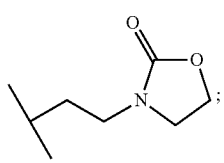

Example 116

Compound of Formula VI: $R_3$=Me, $R_4$=H, $R_5$=CH$_3$ and $R_6$=

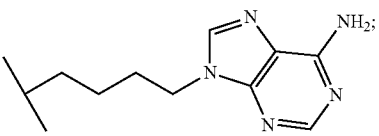 [SMILES: CC(C)CCCCn1cnc2c(N)ncnc21]

Example 117

Compound of Formula VI: $R_3$=Me, $R_4$=H, $R_5$=CH$_3$ and $R_6$=

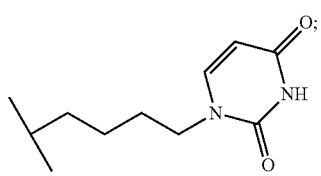

Example 118

Compound of Formula VI: $R_3$=Me, $R_4$=H, $R_5$=CH$_3$ and $R_6$=

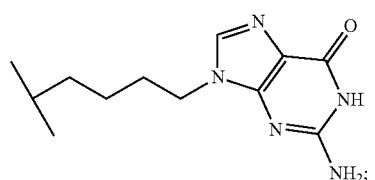

Example 119

Compound of Formula VI: $R_3$=Me, $R_4$=H, $R_5$=CH$_3$ and $R_6$=

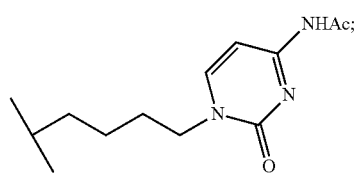 [SMILES: CC(=O)Nc1ccn(CCCCC(C)C)c(=O)n1]

Example 120

Compound of Formula VI: $R_3$=Me, $R_4$=H, $R_5$=CH$_3$ and $R_6$=

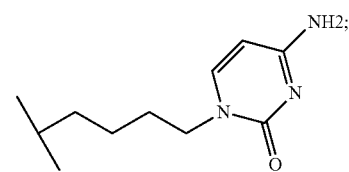

Example 121

Compound of Formula VI: $R_3$=Me, $R_4$=H, $R_5$=CH$_3$ and $R_6$=

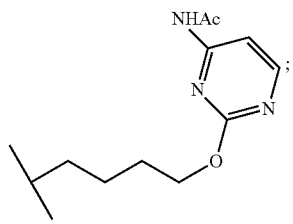 [SMILES: CC(=O)Nc1ccnc(OCCCCC(C)C)n1]

Example 122

Compound of Formula VI: $R_3$=Me, $R_4$=H, $R_5$=CH$_3$ and $R_6$=

Example 123

Compound of Formula VI: $R_3$=Me, $R_4$=H, $R_5$=CH$_3$ and $R_6$=

31

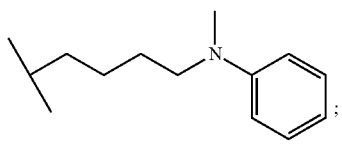

Example 124

Compound of Formula VI: $R_3$=Me, $R_4$=H, $R_5$=CH$_3$ and $R_6$=

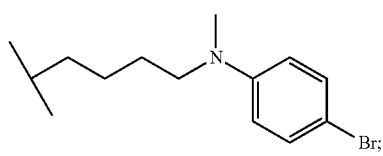 [SMILES: CC(C)CCCCN(C)c1ccc(Br)cc1]

Example 125

Compound of Formula VI: $R_3$=Me, $R_4$=H, $R_5$=CH$_3$ and $R_6$=

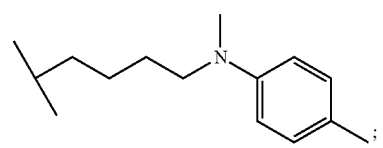 [SMILES: Cc1ccc(N(C)CCCCC(C)C)cc1]

Example 126

Compound of Formula VI: $R_3$=Me, $R_4$=H, $R_5$=CH$_3$ and $R_6$=

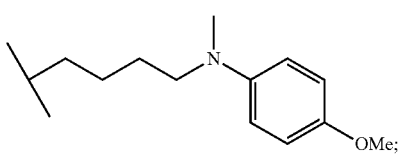 [SMILES: COc1ccc(N(C)CCCCC(C)C)cc1]

Example 127

Compound of Formula VI: $R_3$=Me, $R_4$=H, $R_5$=CH$_3$ and $R_6$=

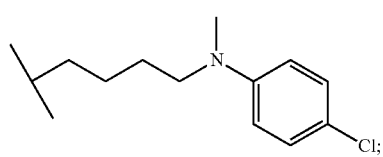

Example 128

Compound of Formula VI: $R_3$=Me, $R_4$=H, $R_5$=CH$_3$ and $R_6$=

32

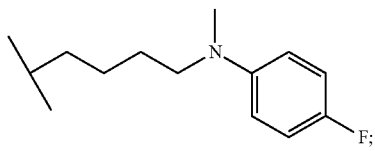 [SMILES: CC(C)CCCCN(C)c1ccc(F)cc1]

Example 129

Compound of Formula VI: $R_3$=Me, $R_4$=H, $R_5$=CH$_3$ and $R_6$=

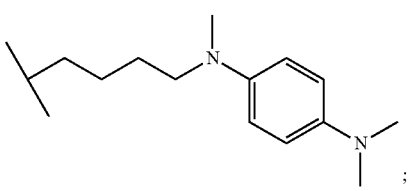 [SMILES: CC(C)CCCCN(C)c1ccc(N(C)C)cc1]

Example 130

Compound of Formula VI: $R_3$=Me, $R_4$=H, $R_5$=CH$_3$ and $R_6$=

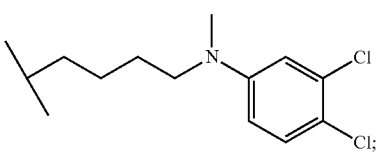

and

Example 131

Compound of Formula VI: $R_3$=Me, $R_4$=H, $R_5$=CH$_3$ and $R_6$=

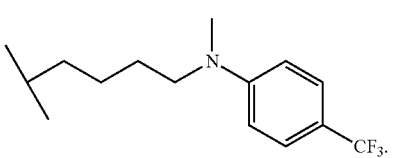 [SMILES: CC(C)CCCCN(C)c1ccc(C(F)(F)F)cc1]

A further embodiment of the present invention includes pharmaceutical compositions comprising any single compound delineated herein, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

Yet a further embodiment of the present invention is a pharmaceutical composition comprising any single compound delineated herein in combination with one or more HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121 (A2), or U.S. Pat. No. 6,348,587B1 or WO 01/60315 or WO 01/32153 or non-nucleoside inhibitors such as, for example, benzimidazole polymerase inhibitors described in EP 1 162196A1 or WO 02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_8$ alkyl," or "$C_1$-$C_{12}$ alkyl," as used herein, refer to saturated, straight- or branched-chain hydrocarbon radicals containing between one and eight, or one and twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_8$ alkenyl," as used herein, refer to straight- or branched-chain hydrocarbon radicals containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The term "$C_2$-$C_8$ alkynyl," as used herein, refer to straight- or branched-chain hydrocarbon radicals containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$ cycloalkenyl" or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —CN, —$N_3$, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl,—NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2$^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)-for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews,* 8:1-38(1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
$Boc_2O$ for di-tert-butyl-dicarbonate;
Boc for t-butoxycarbonyl;
Bz for benzoyl;
Bn for benzyl;
BocNHOH for tert-butyl N-hydroxycarbamate;
t-BuOK for potassium tert-butoxide;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
$Et_2O$ for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
$K_2CO_3$ for potassium carbonate;
MeOH for methanol;
Ms for mesyl or $—SO_2—CH_3$;
$Ms_2O$ for methanesulfonic anhydride or mesyl-anhydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;

NaHSO$_3$ for sodium bisulfite or sodium hydrogen sulfite;
Na$_2$S$_2$O$_3$ for sodium thiosulfate;
NH$_2$NH$_2$ for hydrazine;
NH$_4$HCO$_3$ for ammonium bicarbonate;
NH$_4$Cl for ammonium chloride;
NMMO for N-methylmorpholine N-oxide;
NaIO$_4$ for sodium periodate;
OH for hydroxy;
OsO$_4$ for osmium tetroxide;
TEA or Et$_3$N for triethylamine;
TFA for trifluoroacetic acid;
THF for tetrahydrofuran;
TPP or PPh$_3$ for triphenylphosphine;
Ts for tosyl or —SO$_2$—C$_6$H$_4$CH$_3$;
Ts$_2$O for tolylsulfonic anhydride or tosyl-anhydride;
TsOH for p-tolylsulfonic acid;
Pd for palladium;
Ph for phenyl;
Pd$_2$(dba)$_3$ for tris(dibenzylideneacetone)dipalladium (0);
Pd(PPh$_3$)$_4$ for tetrakis(triphenylphosphine)palladium (0);
TBS for tert-butyl dimethylsilyl; or
TMS for trimethylsilyl;
TMSCl for trimethylsilyl chloride; and
CsA for cyclosporin A.

Synthetic Methods

The compounds and processes of the present invention will be better understood in connection with the following synthetic schemes that illustrate the methods by which the compounds of the invention may be prepared.

The novel cyclosporin analogues of the present invention are derived from cyclosporin A. As shown in Scheme 1, a key intermediate of formula (1-3) was prepared by selective removal of amino acid in position four—N-methyl leucine of cyclosporin A (see Roland Wenger et al, "Synthetic routes to NEtXaa$^4$-cycloporin A derivatives as potential anti-HIV I drugs", *Tetrahedron Letters*, 2000, 41, 7193, which is hereby incorporated by reference in its entirety). Thus, cyclosporin A was reacted with acetic anhydride, optionally in the presence of pyridine or DMAP in CH$_2$Cl$_2$ to give acetylated intermediate (1-1), which was followed by selective cleavage of the amide bond between position three and position four amino acid with trimethyloxonium tetrafluoroborate in CH$_2$Cl$_2$ to afford the intermediate (1-2). Edman degradation of (1-2) gave the key intermediate (1-3).

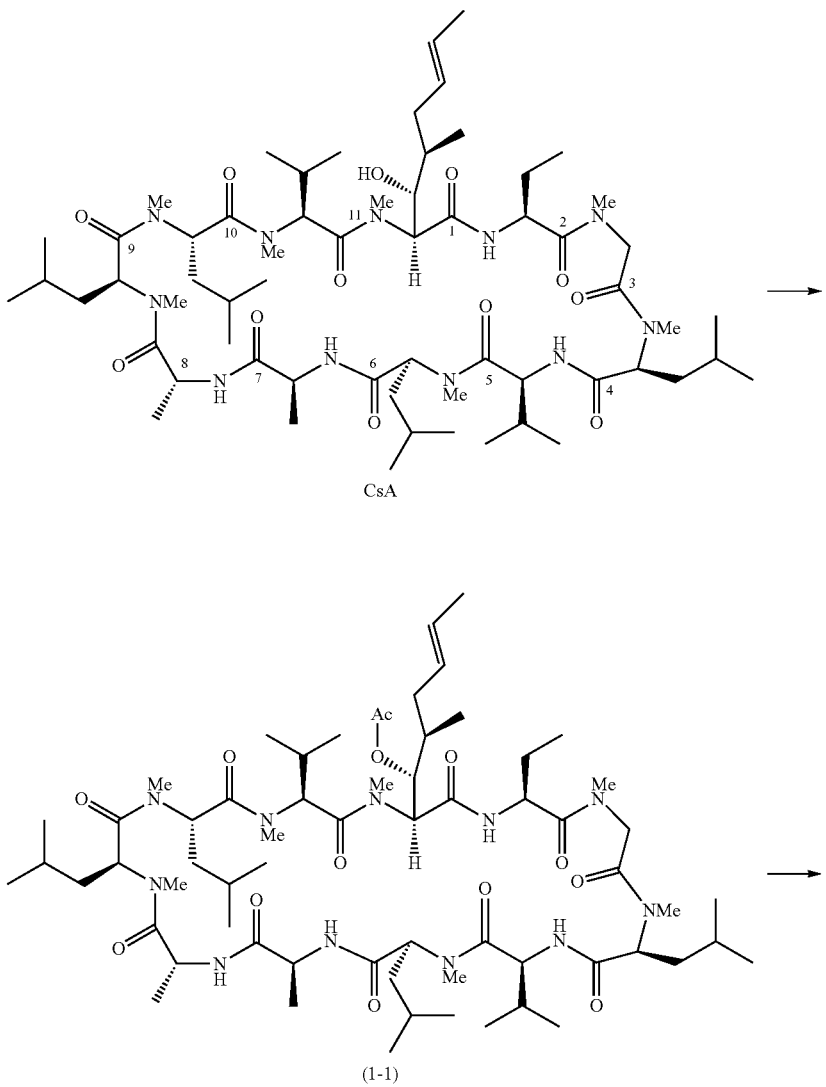

Scheme 1

-continued

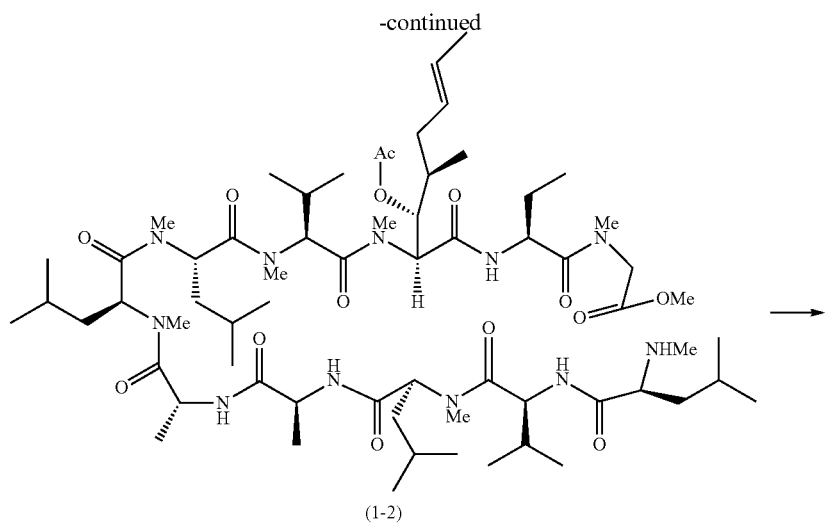

(1-2)

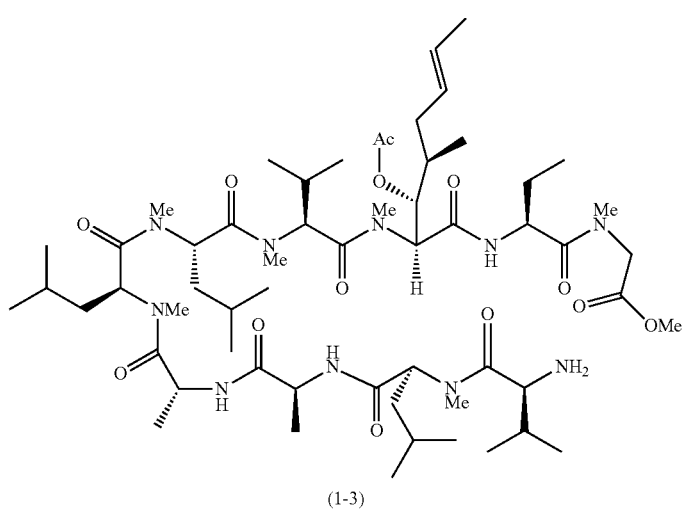 [SMILES: C/C=C/C[C@@H](C)[C@@H](OC(C)=O)[C@@H](C(=O)N[C@@H](CC)C(=O)N(C)CC(=O)OC)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](N)C(C)C ; "(1-3)"]

(1-3)

Scheme 2 illustrates a process of the invention for the preparation of compounds according to the invention. The intermediate of formula (1-3), is then converted to the compound of formula (2-1) by hydrolysis promoted with inorganic base such as but not limited to sodium methoxide, potassium carbonate, sodium carbonate, and the like. The reaction is carried our in a solvent such as but not limited to methanol, ethanol, THF, DMF, $CH_3CN$. The most preferred solvent is methanol. The reaction temperature can vary from 0° C. to about 50° C.

Scheme 2
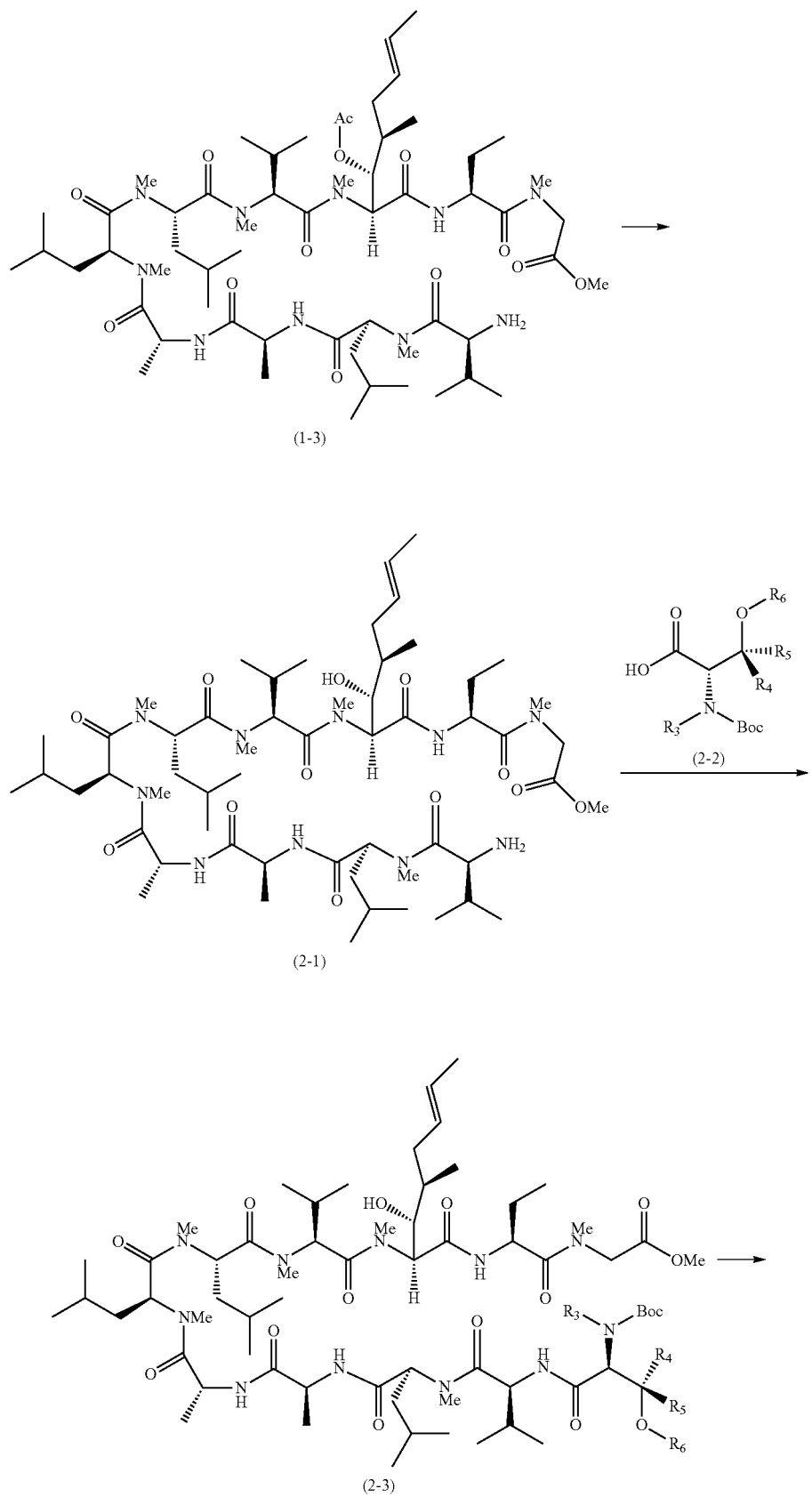

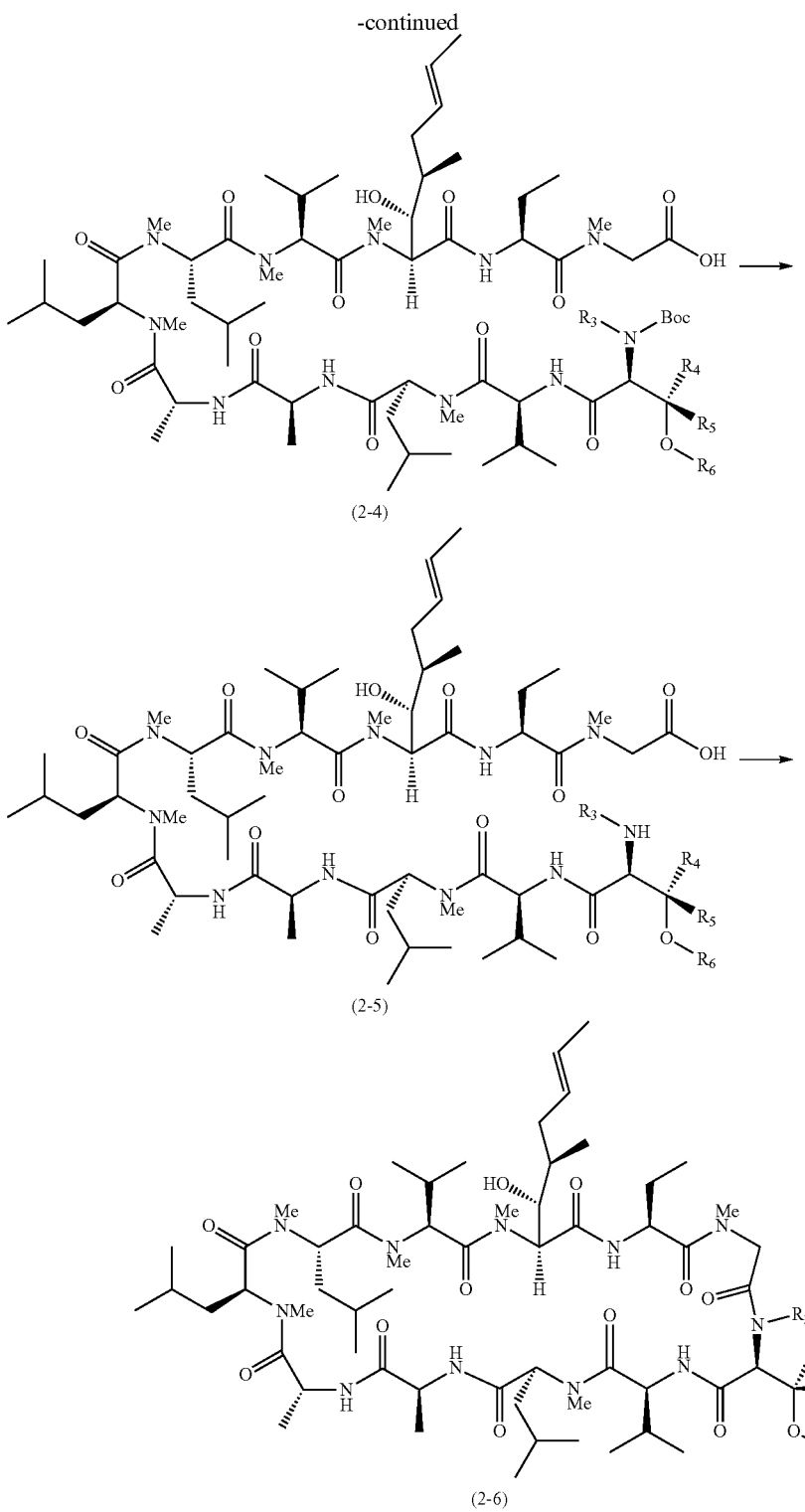

(2-4)

(2-5)

(2-6)

Then the compound of formula (2-1) is coupled with a protected amino acid of the formula (2-2), where $R_6$, $R_3$, $R_4$ and $R_5$ are as previously defined to give the compound of formula (2-3). The coupling regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

The protected amino acids of formula (2-2) are prepared by the method described in Hu, T. and Panek, J. S.; *J. Am. Chem. Soc.* 2002, 124, 11372.

The methyl ester of compound of formula (2-3) is converted to the corresponding acid compound of formula (2-4) via alkaline hydrolysis in protic solvents. Representative alkali compounds include lithium hydroxide, sodium hydroxide, potassium hydroxide, and the like. Suitable solvents include, but are not limited to, methanol, ethanol, isopropanol, butanol, THF, 1,4-dioxane and mixtures thereof. The reaction temperature is preferably 0° to 35° C.

Compound of formula (2-4) is converted to the compound of formula (2-5) by acidic Boc deprotection. The acid can be selected from, but not limited to, TFA, HCl in dioxane, methanesulfonic acid. A more through discussion of the procedures, reagents and conditions for removing protecting groups is described in literature, for example, by T. W. Greene and P. G. M. Wuts in "*Pretective Groups in Organic Synthesis*" 3$^{rd}$ ed., John Wiley & Son, Inc., 1999.

Compound of formula (2-6) is prepared by intramolecular amide formation reaction. The regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, CH$_2$Cl$_2$, DMF and THF. The reaction temperature can vary from 0° C. to about 50° C.

An alternative process for the preparation of the novel cyclosporin analogues of the present invention is also illustrated in Scheme 3.

Scheme 3

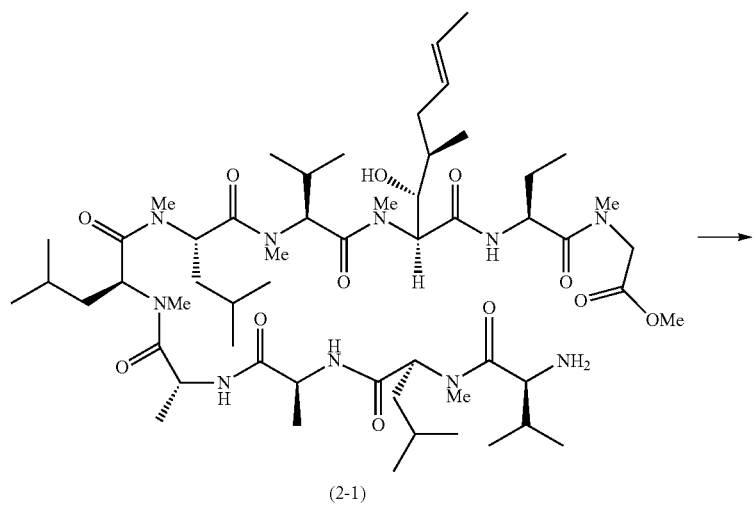

(2-1)

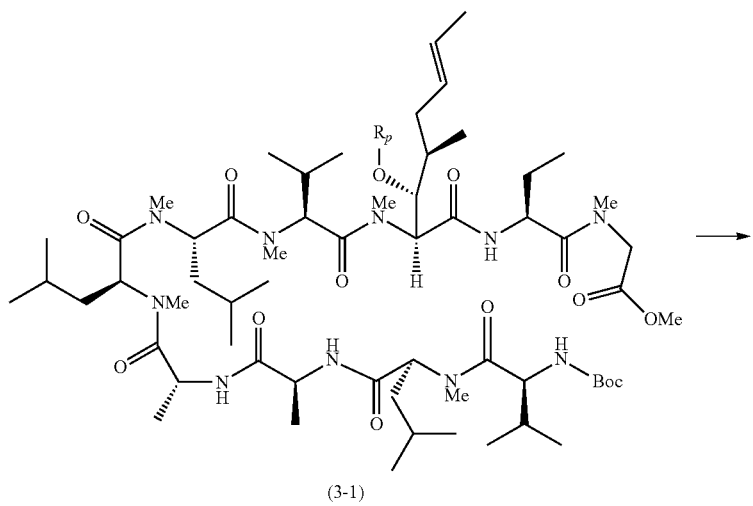

(3-1)

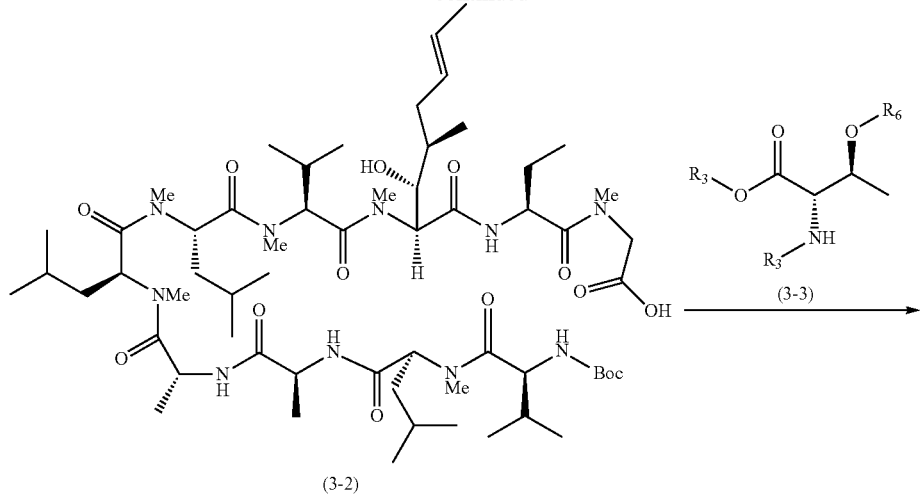
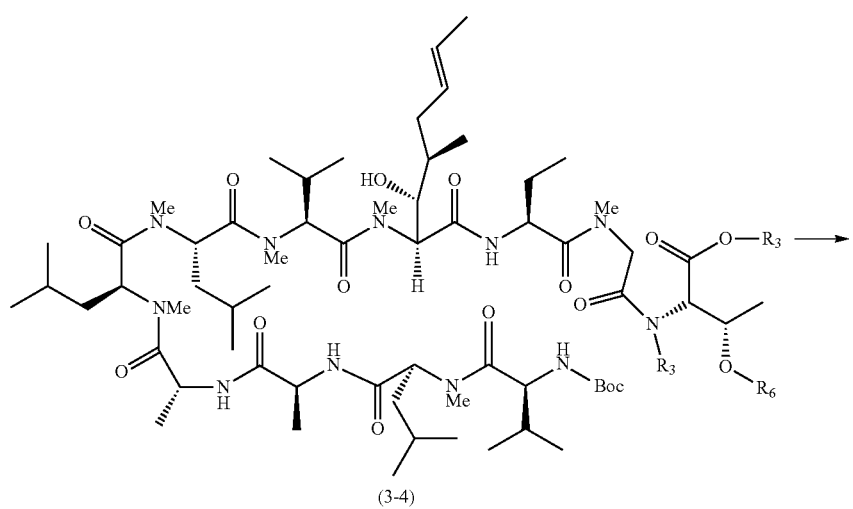
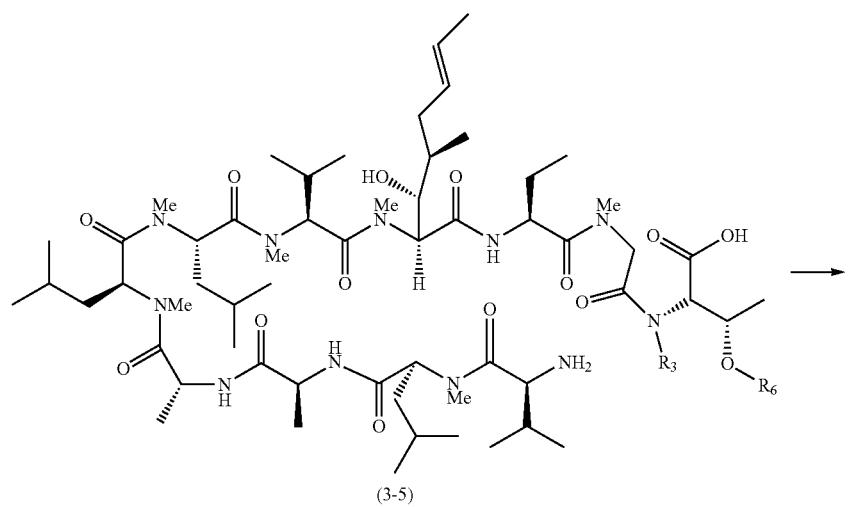

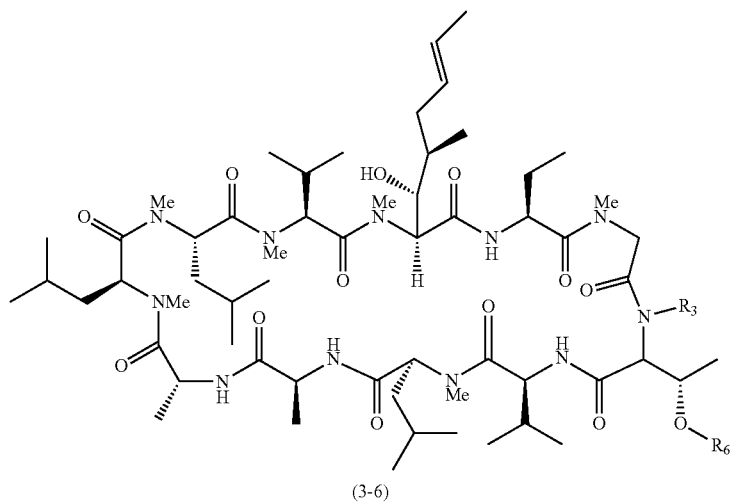

(3-6)

$R_p$ is hydroxy protecting group

The amino group of compound of formula (2-1) is protected by reacting with Boc$_2$O in the presence of a base such as, but limited to TEA, DIPEA, DMAP, pyridine and the like. The reaction can be carried out in a variety of organic solvents such as CH$_2$Cl$_2$, toluene, Et$_2$O, EtOAc and chloroform. Then the hydroxyl group is protected with silylating reagents such as, but not limited to, TMSCl, TBSCl, TESCl, TMSOTf and N, O-bis(trimethylsilyl) acetamide in the presence of an organic base. Preferably, the silylating reagent is TMSCl and N, O-bis-(trimethylsilyl)acetamide, the organic base is 1-methylimidazole. A more through discussion of the procedures, reagents and conditions for protecting hydroxyl group is described in literature, for example, by T. W. Greene and P. G. M. Wuts in "*Pretective Groups in Organic Synthesis*" 3$^{rd}$ Ed., John Wiley & Son, Inc., 1999.

The compound of formula (3-1) is converted to the compound of formula (3-2) by hydrolysis with the essential same condition described in the conversion of (1-3) to (2-1). Further coupling of (3-2) with a protected amino acid of formula (3-3) is proceeded using essential same condition described in the conversion of (2-1) to (2-3) to give the compound of formula (3-4).

Compound of formula (3-4) is converted to the compound of formula (3-5) by acidic N-Boc deprotection followed by ester deprotection. A through discussion of the procedures, reagents and conditions for removing protecting groups is described in literature, for example, by T. W. Greene and P. G. M. Wuts in "*Pretective Groups in Organic Synthesis*" 3$^{rd}$ Ed., John Wiley & Son, Inc., 1999.

Compound of formula (3-6) is prepared by intramolecular amide formation reaction, which is descried in the conversion of (2-5) to (2-6).

Scheme 4 illustrates a process of the invention for the preparation of compounds according to the invention. Reduction of the compound of formula (1-3) with a reducing agent such as, but not limited to NaBH$_4$, followed by protection of the amino group with Fmoc affords the compound of formula (4-1). The reduction is carried out in a protic solvent such as, but not limited to, methanol, ethanol, isopropanol or tert-butanol or a mixture of two protic solvents. The reaction temperature can vary from 0° C. to about 50° C. Protection of the amino group with Fmoc-Cl in the presence of an organic base such as, but not limited to, triethylamine, diisopropylethylamine, DBU, N-methylmorpholine or DMAP, gives the compound of formula (4-1). The reaction is carried out in an aprotic solvent such as, but not limited to, CH$_2$Cl$_2$, DMF or THF. The reaction temperature can vary from 0° C. to about 50° C. Further rearrangement of the compound of formula (4-1) in the presence of an acid, followed by acetyl protection gives the compound of formula (4-2). Suitable acids include, but are not limited to, methanesufonic acid, toluenesulfonic acid, and camphorsulfonic acid. The rearrangement reaction is carried out in a protic solvent such as, but not limited to, methanol, ethanol, isopropanol or tert-butanol.

Scheme 4
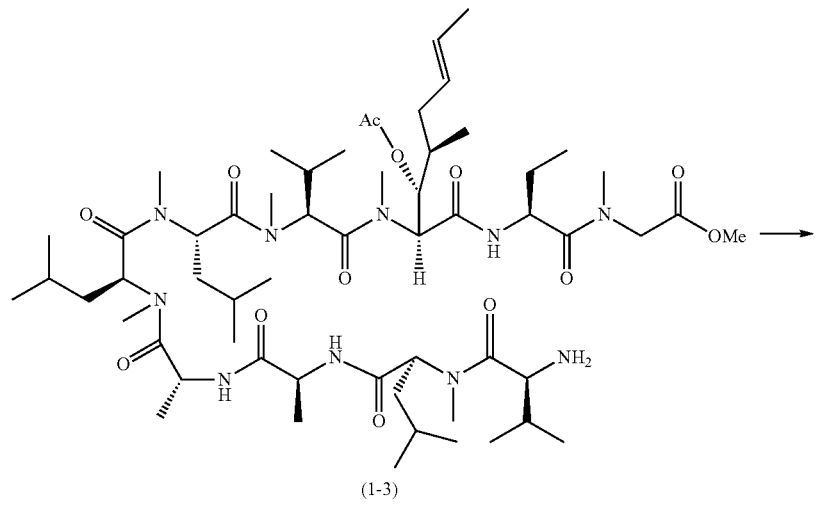
(1-3)
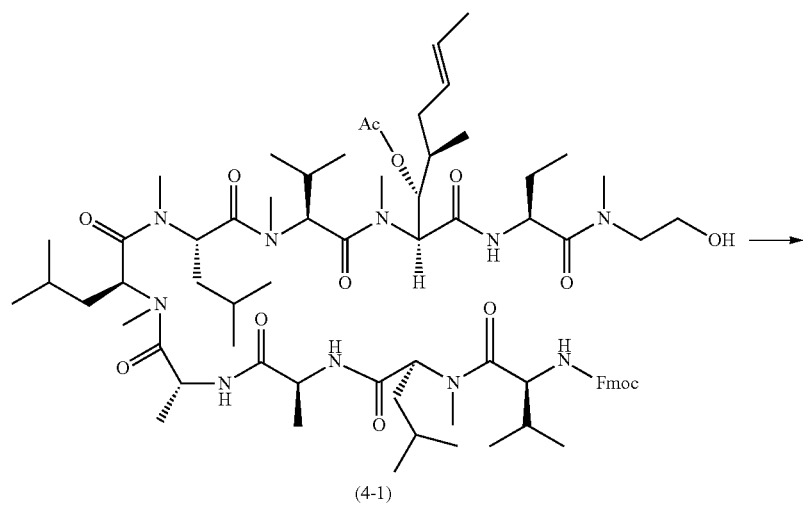
(4-1)
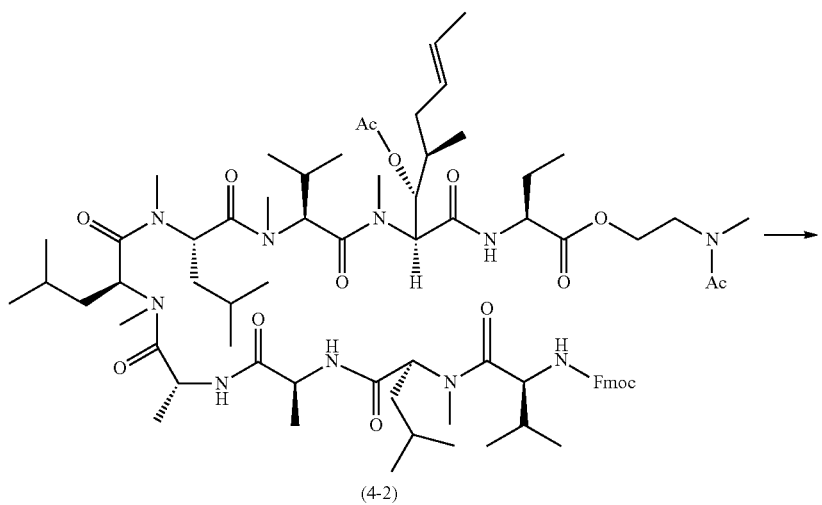
(4-2)

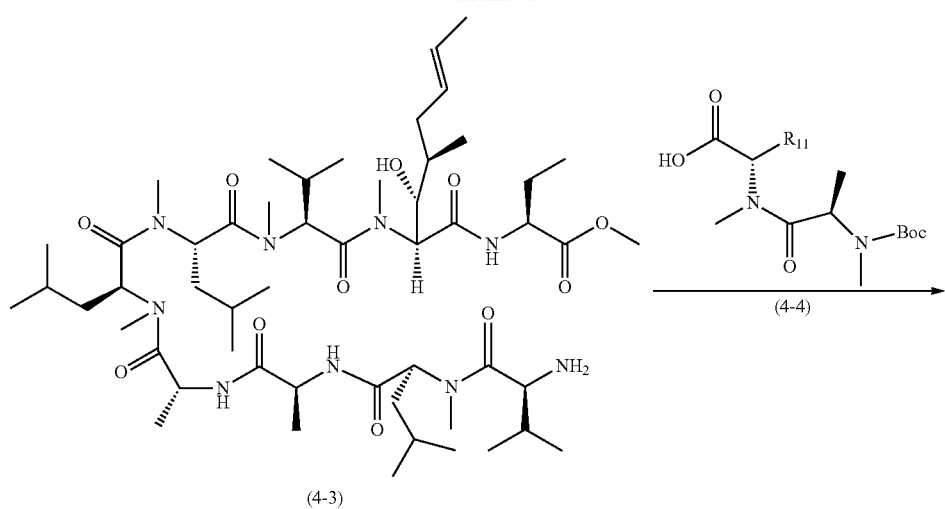
(4-3) (4-4)
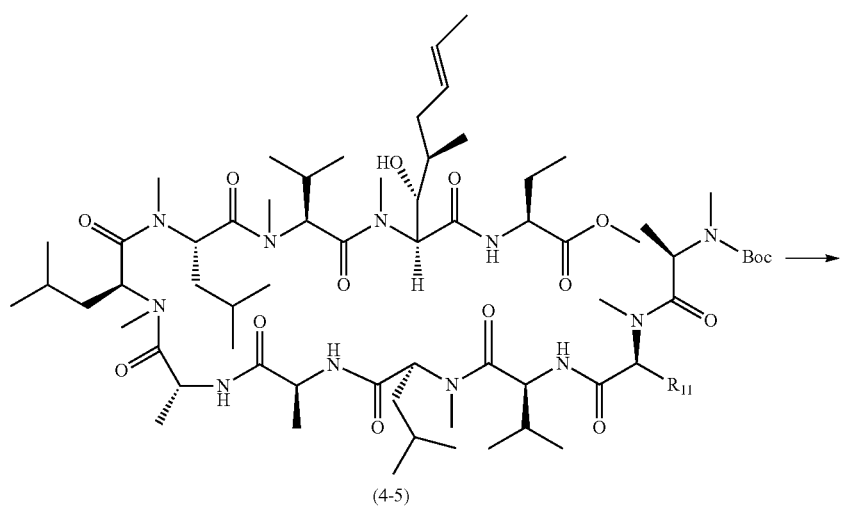
(4-5)
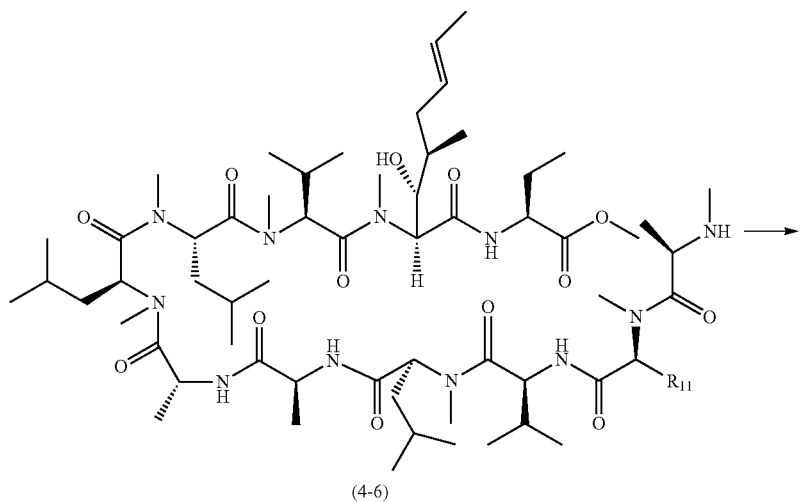
(4-6)

-continued

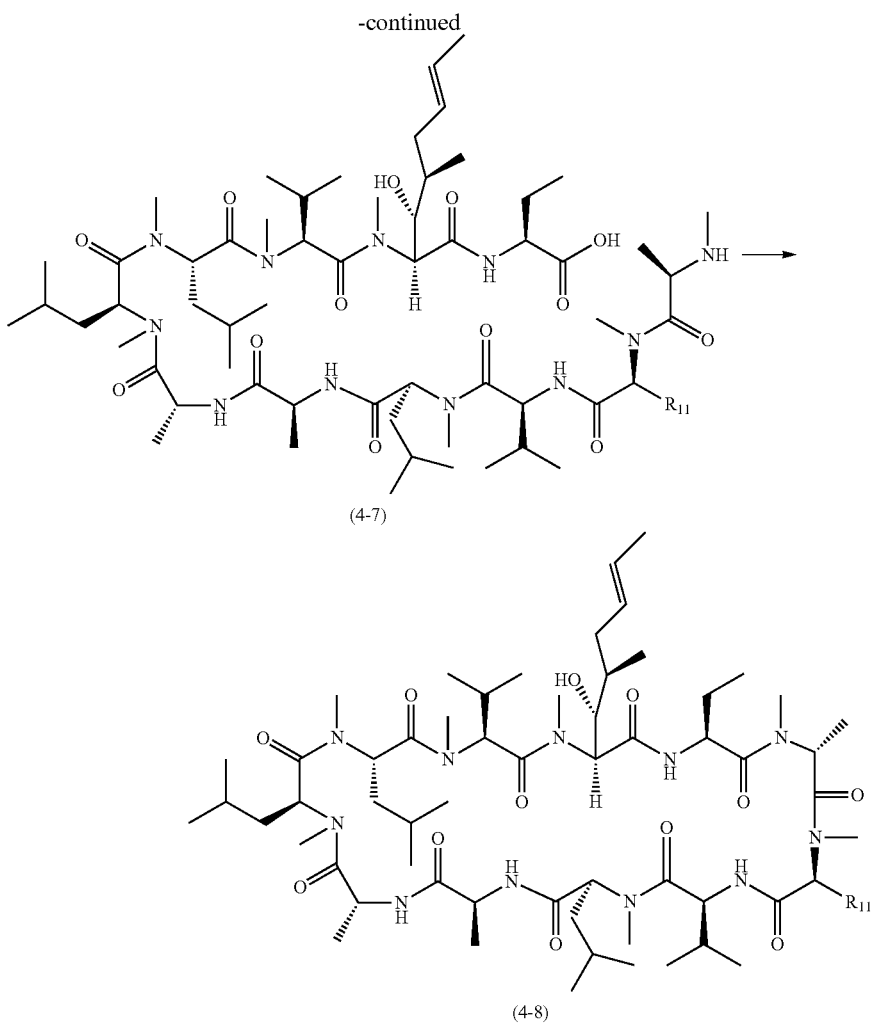

(4-7)

(4-8)

The acetyl protection reaction is carried out in an aprotic solvent such as, but not limited to, $CH_2Cl_2$, $ClCH_2CH_2Cl$, DMF or THF, with acetic anhydride in the presence of base. Suitable bases include, but are not limited to, triethylamine, diisopropylethylamine, DBU, N-methylmorpholine and DMAP. The compound of formula (4-2) is converted to the compound of formula (4-3) with sodium methoxide in methanol.

Then the compound of formula (4-3) is coupled with a protected dipeptide of the formula (4-4) to give the compound of formula (4-5). The coupling regent can be selected from, but not limited to, DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C.

The protected dipeptides of formula (4-4) can be prepared by the method described in Hu, T. and Panek, J. S.; *J. Am. Chem. Soc.* 2002, 124, 11372.

The compound of formula (4-5) is converted to the compound of formula (4-6) by acidic Boc deprotection. The acid can be selected from, but not limited to, TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" $3^{rd}$ ed., John Wiley & Son, Inc., 1999.

The methyl ester of compound of formula (4-6) is converted to the corresponding acid compound of formula (4-7) via alkaline hydrolysis in protic solvents. Representative alkali compounds include lithium hydroxide, sodium hydroxide, potassium hydroxide, and the like. Suitable solvents include, but are not limited to, methanol, ethanol, isopropanol, butanol, THF, 1,4-dioxane and mixtures there of. The reaction temperature is preferably 0° to 35° C. Compound of formula (4-8) is prepared by intramolecular amide formation reaction. The regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

Compound of Formula V: $R_3$=$CH_3$, $R_4$=H, $R_5$=$CH_3$ and $R_6$=Ac

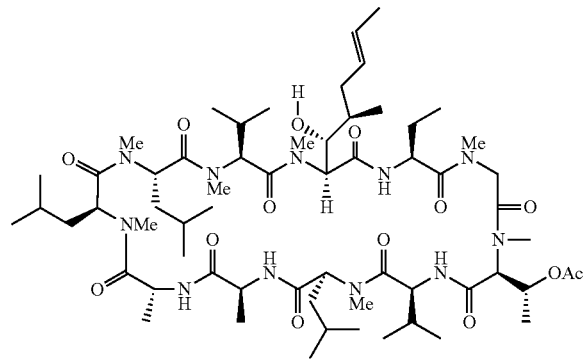 [SMILES: C/C=C/C[C@@H](C)[C@@H](O)[C@H]1C(=O)N[C@@H](CC)C(=O)N(C)CC(=O)N(C)[C@@H]([C@@H](C)OC(C)=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1a: Compound of Formula (1-1)

CsA (481 g, 0.4 mol) was dissolved in anhydrous $CH_2Cl_2$ (1.8 L). Acetic anhydride (163.3 g, 1.6 mol) was added followed by DMAP (48.86 g, 0.4 mol) at room temperature under nitrogen. The reaction mixture was stirred for 36 hrs. The reaction mixture was diluted with 6 L of isopropyl acetate, followed by 8 L of water and stirred for 30 mins. The organic layer was separated and washed with saturated $NaHCO_3$ (4×6 L) and brine (6 L). The organic phase was dried over $Na_2SO_4$ and concentrated. The resulted white foam was dried under vacuum to afford the compound of formula (1-1) (520 g, 95.5% HPLC purity).

MS (ESI): 1244.8 m/z (M+1).

Step 1b: Compound of Formula (1-2)

Compound of formula (1-1) (250 g, 0.2 mole) was dissolved in anhydrous $CH_2Cl_2$ (2 L). Trimethyloxoniumtetrafluoroborate (89.12 g, 0.6 mol) was added at 0° C. and the reaction mixture was stirred at room temperature for 20 hrs. Methanol and water (1:1 mixture, 2.5 L) was added via a dropping funnel over 15 mins at 0° C. and then stirred at room temperature for 3 hrs. Reaction mixture was further diluted with 2 L of $CH_2Cl_2$ and 2 L of water. The organic layer was separated and washed with saturated $Na_2CO_3$ (2 L) and brine (2 L), and then dried over $Na_2SO_4$. The solvent was removed and the residue was purified on silica gel column to afford the compound of formula (1-2) (170 g, 92.5 HPLC purity).

MS (ESI): 1276.8 m/z (M+1).

Step 1c: Compound of Formula (1-3)

Compound of formula (1-2) (230 g, 0.18 mole) was dissolved in anhydrous THF (1.5 L) and Phenyl thioisocyanate (24.35 g, 0.18 mole) was added over 15 mins at 0° C. The reaction mixture was stirred at room temperature for 2 hrs and diluted with 1 L of water and 2.5 L of ethyl acetate. The organic layer was separated and washed with brine (1 L), and then dried over $Na_2SO_4$ and concentrated. After dried under vacuum for 24 hrs, the residue was dissolved in anhydrous $CH_2Cl_2$ (2.66 L). TFA (455 mL) was added at 0° C. over 30 mins and the reaction mixture was stirred at room temperature for 4 hours. Reaction was quenched with saturated $Na_2CO_3$ (3 L) at −15° C. The organic layer was separated and washed with brine (3 L), and then dried over $MgSO_4$. Concentrated and the residue was purified on silica gel column to afford the compound of formula (1-3) (130 g).

MS (ESI): 1149.7 m/z (M+1).

Step 1d: Compound of Formula (2-1)

Compound of formula (1-3) (11.6 g, 10 mmol)) was dissolved in anhydrous MeOH (100 ml). The solution was added sodium methoxide (1.62 g, 30 mmol) and stirred at room temperature for 6 hrs. The mixture was diluted with ethyl acetate (200 ml) and quenched with 1N HCl (pH-5). The organic layer was separated and washed with saturated $NaHCO_3$ and brine, and then dried over $MgSO_4$. Concentrated and the residue was purified on silica gel column to afford the compound of formula (2-1) (9.8 g).

MS (ESI): 1107.8 m/z (M+1).

Step 1e: Compound of Formula (2-3)

To a 250 mL round-bottomed flask were added the compound from step 1d (0.91 g, 0.82 mmol), the compound of formula (2-2), where $R_3$ is methyl, $R_4$ is H, $R_5$ is methyl and $R_6$ acetyl (276 mg, 1 mmol), $CH_2Cl_2$ (20 mL), BOP (437.9 mg, 0.99 mmol), and DMAP (241.9 mg, 1.98 mmol) respectively. The solution was stirred at room temperature for 16 hrs. Diluted with $CH_2Cl_2$, washed with 10% citric acid, water, saturated $NaHCO_3$, brine and dried over $Na_2SO_4$. Concentrated and the residue was purified by flash chromatography (MeOH in $CH_2Cl_2$, 0~20%, v/v) to afford a white solid 1.1 g.

MS (ESI): 1364.8 m/z (M+1).

Step 1f: Compound of Formula (2-4)

To a 50 ml, round-bottomed flask were added the compound from step 1e (1.08 g, 0.79 mmol), THF (7 mL) and water (3 mL) respectively and the solution was cooled to 0° C. followed by the addition of lithium hydroxide monohydrate (100 mg, 2.4 mmol). After stirred at 0° C. for 3 h, the reaction mixture was diluted with ethyl acetate (50 ml), washed with 10% citric acid solution, brine and dried over anhydrous $Na_2SO_4$. The solvent was removed to give the desired product 1.0 g as white foam which was used for next step reaction without further purification.

MS (ESI): 1350.8 m/z (M+1).

Step 1g: Compound of Formula (2-5)

To a 50 mL round-bottomed flask were added the compound from step 1f (380 mg, 0.26 mmol) from step 1f were added $CH_2Cl_2$ (3 mL) and the solution was cooled to 0° C. followed by the addition of TFA (3 mL) dropwise. The reaction mixture was stirred at 0° C. for 2 hrs and the solvents were removed in vacuo and the residue was dissolved in $CH_2Cl_2$ (30 mL). Washed with saturated $NaHCO_3$, brine and dried over anhydrous $Na_2SO_4$, The solvent was removed and the residue was purified by flash chromatography (MeOH/$CH_2Cl_2$, 1-10%, v/v) to give colorless oil 380 mg.

MS (ESI): 1250.8 m/z (M+1).

Step 1h: Compound of Formula (2-6)

To a 500 ml round-bottomed flask equipped with a dropping funnel were added BOP (141.5 mg, 0.32 mmol), $CH_2Cl_2$ (250 ml) followed by addition of a solution of DMAP (39.1 mg, 0.32 mmol) and the compound from step 1g (200 mg, 0.16 mmol) in $CH_2Cl_2$ (100 mL) during 2 hrs at room temperature. The solution was stirred at room temperature for 16 hrs. The reaction was quenched with saturated $NaHCO_3$. The organic layer was separated and washed with brine dried over anhydrous $Na_2SO_4$. The solvent was removed and the residue was purified by flash chromatography ($MeOH/CH_2Cl_2$, 1-10%, v/v) to give a white solid 134 mg.

MS (ESI): 1232.9 m/z (M+1).

Example 2

Compound of Formula V: $R_3$=$CH_3$, $R_4$=H, $R_5$=$CH_3$ and $R_6$=allyl the residue was purified by column chromatography (40% ethyl acetate in hexane) to give a pail yellow syrup 2.09 g. (yield: 80.8%).

$^1$H-NMR (500 MHz, $CDCl_3$): δ 1.23 (d, 3H, J=6.5 Hz), 1.46 (s, 9H), 3.94 (dd, 1H, J=5.5, 7.0 Hz), 4.06-4.14 (m, 2H), 4.34 (dd, 1H, J=2.0, 7.0 Hz) 5.17 (dd, 1H, J=0.9, 8.5 Hz), 5.23-5.27 (m, 1H), 5.30 (d, 1H, J=8.5 Hz), 5.81-5.86 (m, 1H).

Step 2b: Compound of Formula (2-2) where $R_3$ is methyl $R_4$=H, $R_5$=$CH_3$ and $R_6$ is allyl To a solution of the compound from step 2a (1.96 g, 7.57 mmol) in mixture of THF: DMF (17:1, 24 ml) was added sodium hydride (60% dispersion in mineral oil, 1.0 g) at 0° C., After stirred for 20 min at 0° C. methyliodide (1.41 ml, 22.7 mmol) was added, the reaction mixture was stirred at 0° C. for 2 hrs, then at room temperature for 17 hrs. The reaction mixture was poured into ice water (100 ml), acidified with 10% citric acid and extracted with ethyl acetate (3×100 ml). The combined organic layers were washed with

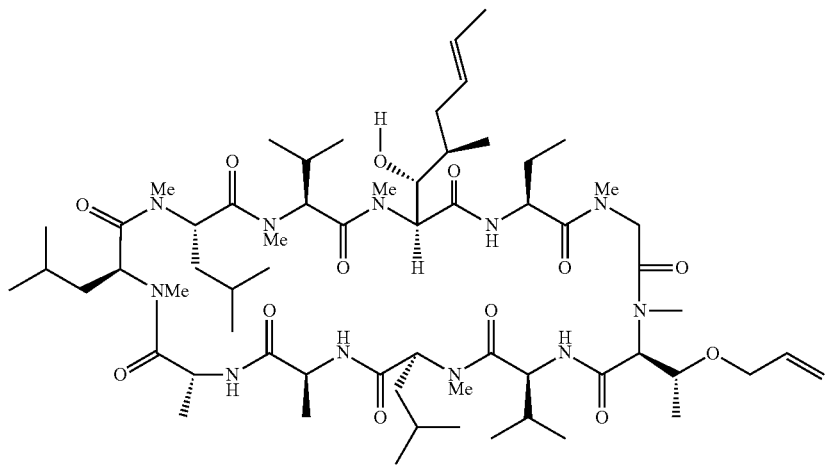 [SMILES: C=CCO[C@H](C)[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)CC(=O)N1C]

Step 2a: Compound of Formula (2-2) where $R_3$ is H, $R_4$=H, $R_5$=$CH_3$ and $R_6$ is allyl To a solution of N-Boc threonine (2.19 g, 9.98 mmol) in DMF (35 ml), sodium hydride (60% dispersion in mineral oil, 0.88 g) was added at −15° C. After stirred for 2 hrs at −15° C., allyl bromide (1.33 g, 10.98 mmol) was added and the mixture was stirred for overnight at room temperature. The reaction mixture was poured into water (100 ml), extracted with diethyl ether (2×100 ml). The aqueous layer was acidified with 10% citric acid, extracted with ethyl acetate (3×100 ml). The combined organic layers were washed with water (6×100 ml), then brine (2×100 ml), and dried over anhydrous $Na_2SO_4$. The solvent was removed and water (3×100 ml), brine (2×100 ml) and dried over anhydrous sodium sulfate. The solvent was removed and the residue was purified on flash column (25% ethyl acetate inhexanes) to give pail yellow syrup (1.6 g, 77.3%).

$^1$H-NMR (500 MHz, $CDCl_3$): δ 1.20 (t, 3H, J=6.5 Hz), 1.44 (s, 3H), 1.47 (s, 6H), 3.00 (d, 3H, J=7.5 Hz), 3.89-3.93 (m, 1H), 4.05-4.23 (m, 3H), 4.64 (d, 0.3H J=5.0 Hz), 4.85 (d, 0.6 H, J=5 Hz), 5.12 (dd, 1H, J=0.9, 8.5 Hz), 5.20-5.25 (m, 1H), 5.82-5.88 (m, 1H).

Then the compound of example 2 was prepared using essentially same procedure from step 1e to step 1h in the preparation of the compound of example 1 with the compound from step 1d and the compound of formula (2-2) where $R_3$ is methyl and $R_6$ is allyl which was prepared in step 2b.

MS (ESI): 1230.7 m/z (M+1).

73 …

Example 3

Compound of Formula V: $R_3$=$CH_3$, $R_4$=H, $R_5$=$CH_3$ and $R_6$=benzyl

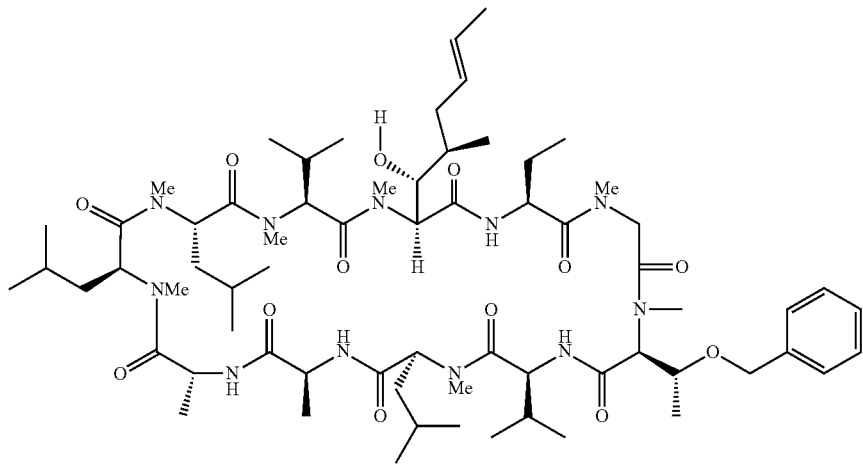 [SMILES: C/C=C/C[C@@H](C)[C@@H](O)[C@H]1C(=O)N[C@@H](CC)C(=O)N(C)CC(=O)N(C)[C@@H]([C@@H](C)OCc2ccccc2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

The compound of example 3 was prepared using essentially same procedure from step 1e to step 1h in the preparation of the compound of example 1 with the compound from step 1d and the compound of formula (2-2) where $R_3$ is methyl and $R_6$ is benzyl.

MS (ESI): 1280.8 m/z (M+1).

Example 4

Compound of Formula V: $R_3$=$CH_3$, $R_4$=H, $R_5$=$CH_3$ and $R_6$=

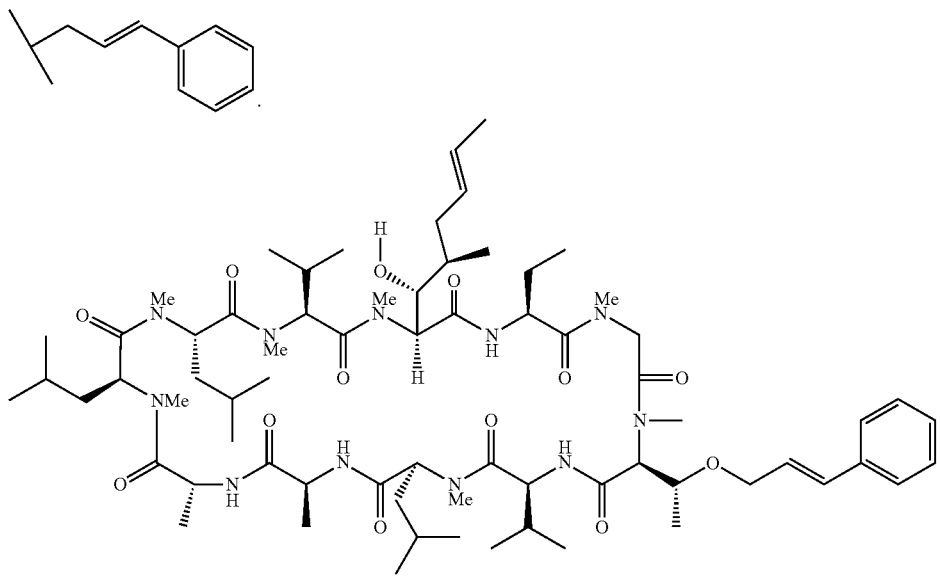

To a 2 mL vial were added the compound of example 2 (10 mg), bromobenzene (100 μL), Pd(OAc)$_2$ (4.5 mg), PPh$_3$ (25 mg), CH$_3$CN (0.5 mL), Et$_3$N (110 μL) under N$_2$ and the vial was sealed and then the mixture was irridiated on microwave reactor at 150° C. for 5 min. Solvents were removed and the residue was purified by column chromatography (5% MeOH in DCM) to give desired product.

ESI MS m/z=1306.91 [M+H]$^+$.

Example 5

Compound of Formula V: $R_3$=$CH_3$, $R_4$=H, $R_5$=$CH_3$ and $R_6$=

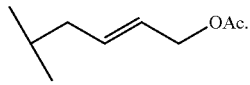

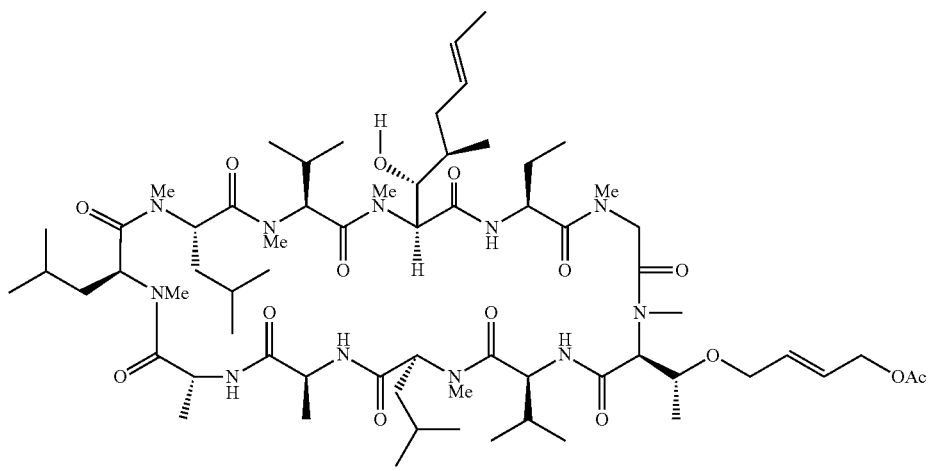

Step 5a: Compound of Formula (2-2) where $R_3$ is methyl $R_4$=H, $R_5$=$CH_3$ and $R_6$ is

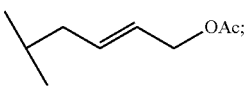

To a 250 mL round-bottomed flask were added the compound of step 2b (1.8 g, 6.59 mmol), 1,4-diacetoxy-2-butene (16.2 g, 56.2 mmol), Hoveyda-Grubbs 2nd generation catalyst (413.6 mg, 0.66 mmol) and the flask was capped with a rubber septum stopper. Vacuum was applied and backflashed with $N_2$ three times. Degassed 1,2-dichloroethane (70 mL) was added and the reaction mixture was stirred at 40° C. for 16 hrs. Concentrated and charged with water (100 mL). The biphasic mixture was cooled to 0° C. followed by addition of 2 N NaOH (6.5 mL). The mixture was stirred for 10 min at 0° C., extracted with $Et_2O$ (100 mL×2). The aqueous layer was acidified with 2 N HCl at 0° and extracted with $Et_2O$ (250 mL×3). The combined organic layers were washed with brine, dried, concentrated to give pale brown syrup 2.2 g, 83% yield.

Then the compound of example 5 was prepared using essentially same procedure from step 1e to step 1h in the preparation of the compound of example 1 with the compound from step 1d and the compound of formula (2-2) where $R_3$ is methyl $R_4$=H, $R_5$=$CH_3$ and $R_6$ is

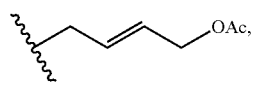 [SMILES: *C/C=C/COC(C)=O]

which was prepared in step 5a.

ESI MS m/z=1302.8 [M+H]$^+$.

Example 6

Compound of Formula V: $R_3$=$CH_3$, $R_4$=H, $R_5$=$CH_3$ and $R_6$=

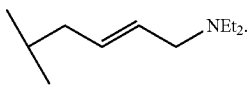

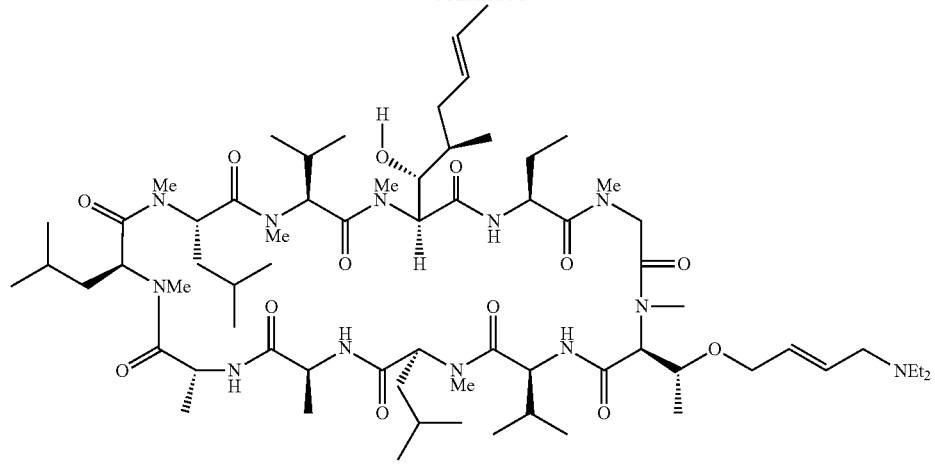

To a solution of the compound of example 5 (22 mg), Pd$_2$(dba)$_3$ (18 mg), dppb (16 mg) in THF (2 mL) was added diethylamine (0.6 mL) under N$_2$. The mixture was degassed and refluxed for 4 hrs. The solvent was removed and the residue was purified by column chromatography to give light brown foam (20 mg).

ESIMS m/z=1315.9 [M+H]$^+$.

Example 7

Compound of Formula V: R$_3$=CH$_3$, R$_4$=H, R$_5$=CH$_3$ and R$_6$=

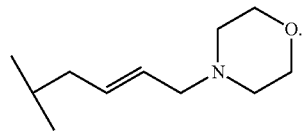

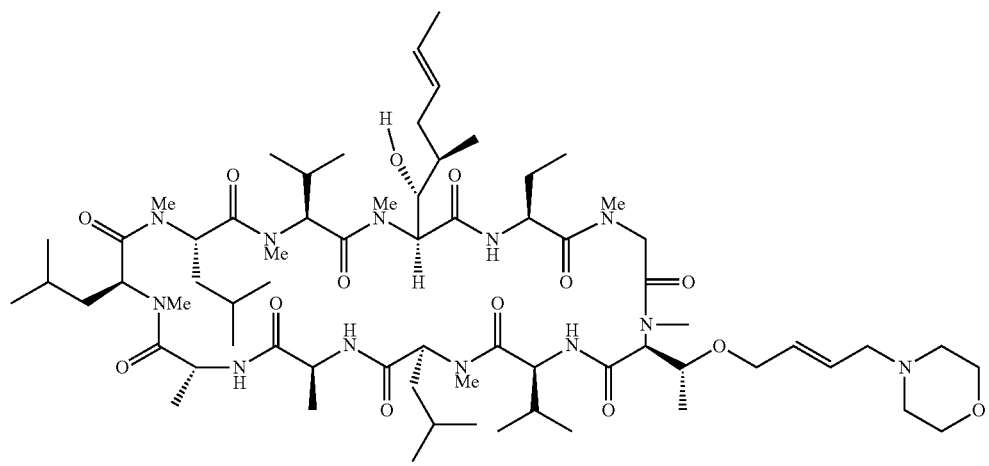

The compound of example 7 was prepared using essentially same procedure in the preparation of the compound of example 6 with the compound of example 5 and morpholine.

ESI MS m/z=1329.9 [M+H]$^+$.

Example 8
Compound of Formula V: $R_3$=$CH_3$, $R_4$=H, $R_5$=$CH_3$ and $R_6$=
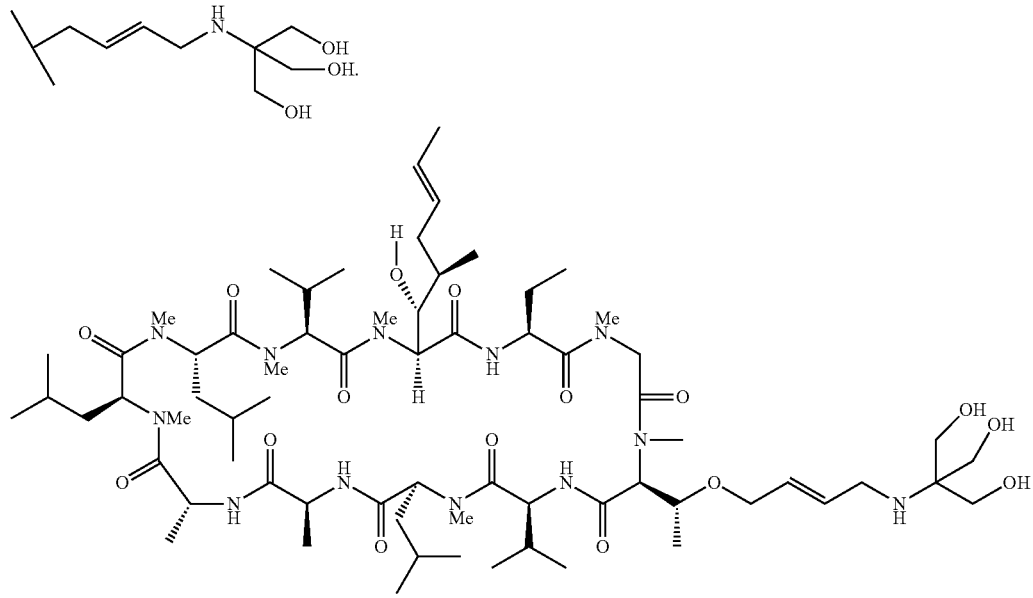
The compound of example 8 was prepared using essentially same procedure in the preparation of the compound of example 6 with the compound of example 5 and tris-(hydroxymethyl)aminomethane.
ESI MS m/z=1363.9 [M+H]$^+$.
Example 9
Compound of Formula V: $R_3$=$CH_3$, $R_4$=H, $R_5$=$CH_3$ and $R_6$=
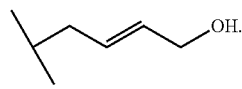
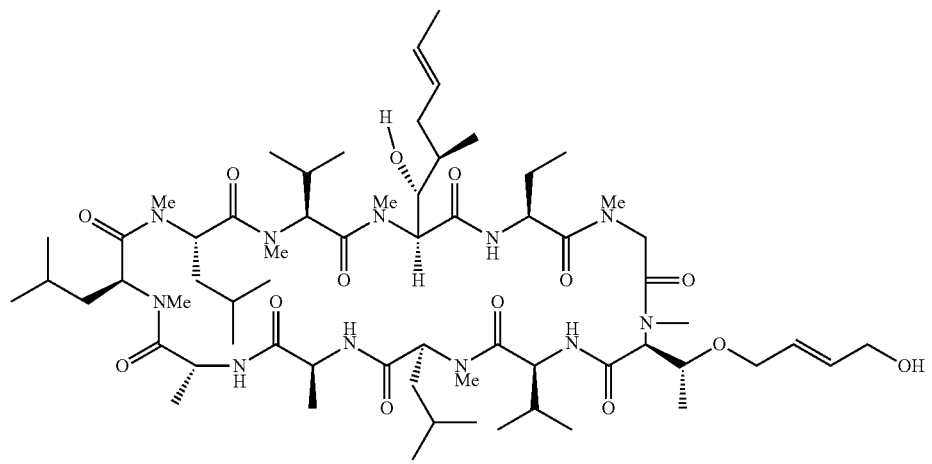

To a solution of compound of example 5 (47 mg, 0.038 mmol) in MeOH (2 mL) was added $K_2CO_3$ (30 mg, 0.22 mmol) at 0° C. After stirred at 0° C. for 2 hrs, the reaction mixture was concentrated and purified by HPLC to give a white solid 25 mg.

ESI MS m/z=1260.8 $[M+H]^+$.

Example 10

Compound of Formula V: $R_3$=$CH_3$, $R_4$=H, $R_5$=$CH_3$ and $R_6$=

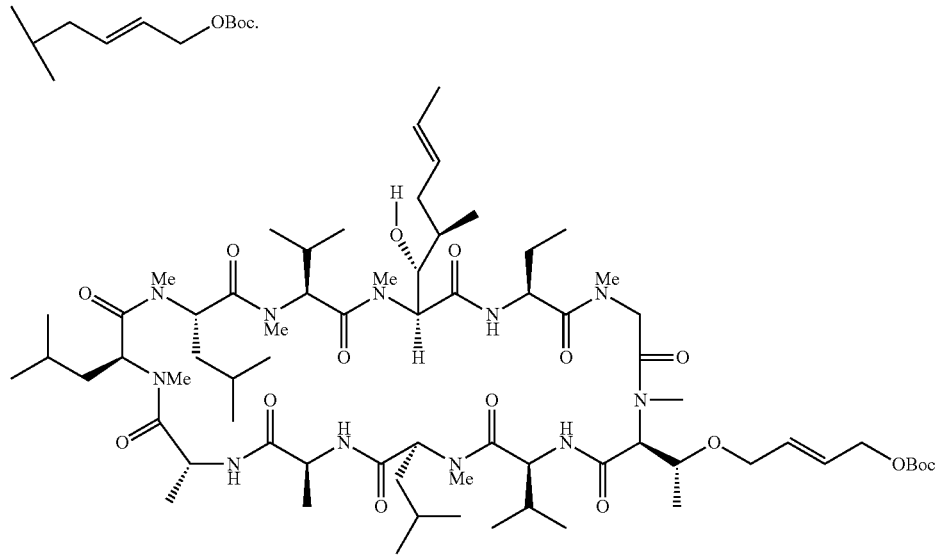

To a solution of compound of example 9 (330 mg, 0.26 mmol) in $CH_2Cl_2$ (10 ml) was added $Boc_2O$ (114 mg, 0.52 mmol), DMAP (16.5 mg) at room temperature. After stirred at room temperature for 4 hrs, the reaction mixture was concentrated and purified by flash chromatography to give a white solid 300 mg.

ESI MS m/z=1360.8 $[M+H]^+$.

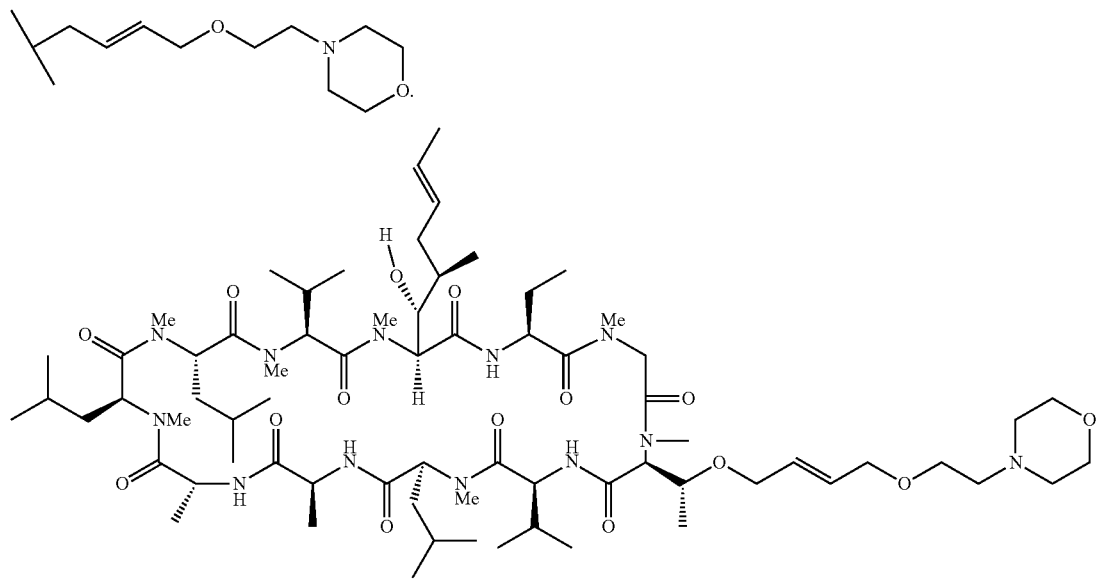

Example 11

Compound of Formula V: $R_3$=$CH_3$, $R_4$=H, $R_5$=$CH_3$ and $R_6$=

The compound of example 11 was prepared using essentially same procedure in the preparation of the compound of example 6 with the compound of example 10 and 2-morpholin-4-yl-ethanol.
ESI MS m/z=1373.9 [M+H]$^+$.

Example 12

Compound of Formula V: $R_3$=$CH_3$, $R_4$=H, $R_5$=$CH_3$ and $R_6$=

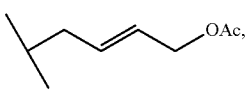

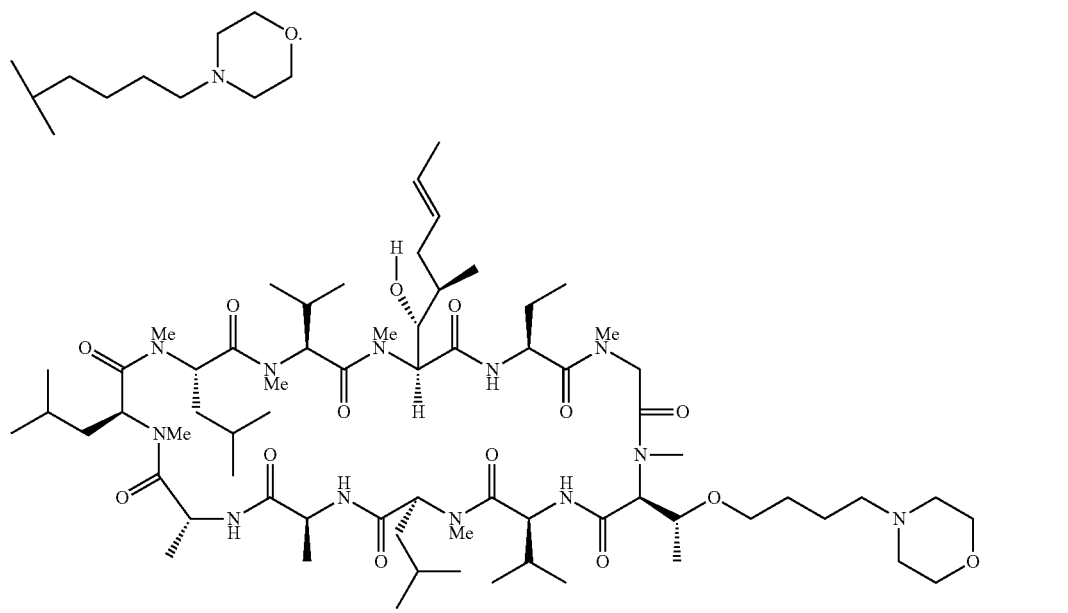

Step 12a: Compound of Formula (2-2) where $R_3$ is methyl $R_4$=H, $R_5$=$CH_3$ and $R_6$ is

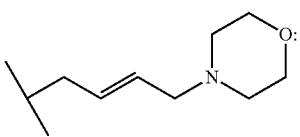

To a solution of compound of formula (2-2) where $R_3$ is methyl, $R_4$ is H, $R_5$ is $CH_3$ and $R_2$ is which was prepared in step 5a (2.76 g, 8 mmol) in anhydrous THF was added morphline (6.76 g, 80 mmol), $Pd_2(dba)_2$ (460 mmol, 0.5 mmol) and dppb (424 mg, 1 mmol) at room temperature. The mixture was degassed and heated to 65° C. After stirred at 65° C. for 4 hrs, the reaction mixture was concentrated and the residue was purified by flash chromatography to give colorless oil (2.5 g).

Step 12b: Compound of Formula (2-2) where $R_3$ is methyl $R_4$=H, $R_5$=$CH_3$ and $R_6$ is A mixture of compound of formula (2-2) where $R_3$ is methyl and $R_6$ is

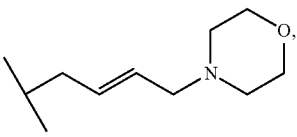

which was prepared in step 12a (350 mg) and 10% palladium on carbon (40 mg) in MeOH (10 ml) was stirred at room temperature under $H_2$ for 13 hrs. The mixture was filtered through a pad of celite and the filtrate was concentrated to give the title compound as colorless oil (350 mg).

Then the compound of example 12 was prepared using essentially same procedure from step 1e to step 1h in the preparation of the compound of example 1 with the compound from step 1d and the compound of formula (2-2) where $R_3$ is methyl $R_4$=H, $R_5$=$CH_3$ and $R_6$ is

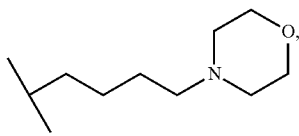

which was prepared in step 12b.
ESI MS m/z=1331.9 [M+H]⁺.

Example 13

Compound of Formula V: $R_3$=CH$_3$, $R_4$=H, $R_5$=CH$_3$ and $R_6$=

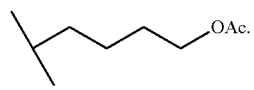

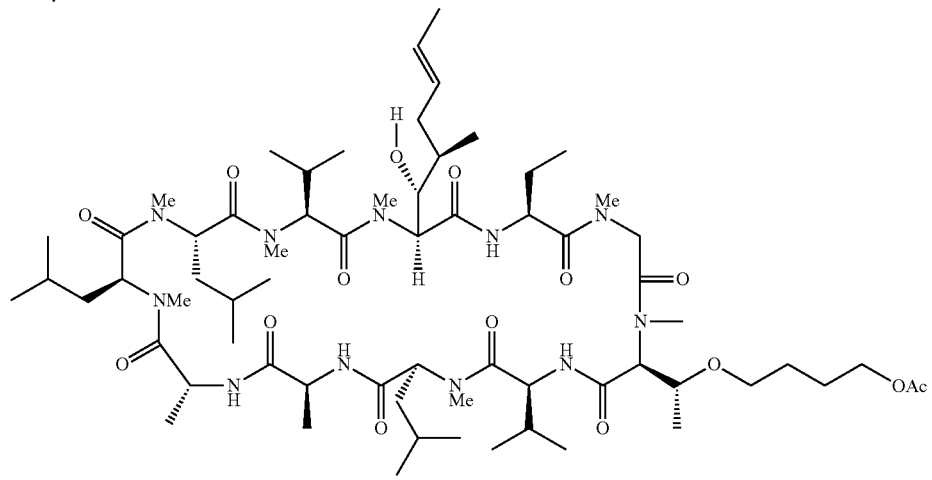

Step 13a: Compound of Formula (2-2) where $R_3$ is methyl $R_4$=H, $R_5$=CH$_3$ and $R_6$ is

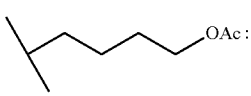

To a solution of compound of formula (2-2) where $R_3$ is methyl and $R_4$ is

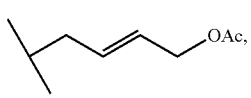

which was prepared in step 5a (2.76 g, 8 mmol) in ethyl acetate (40 ml) was added 5% palladium on carbon (400 mg). The mixture was stirred under H2 (1 atm) at 0° C. for 2 hrs and filtered through a pad of celite. The filtrate was concentrated and purified by flash chromatography to give the title compound as colorless oil (2.0 g).

Then the compound of example 13 was prepared using essentially same procedure from step 1e to step 1h in the preparation of the compound of example 1 with the compound from step 1d and the compound of formula (2-2) where $R_3$ is methyl $R_4$=H, $R_5$=CH$_3$ and $R_6$ is

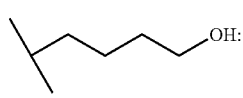

which was prepared in step 13a.
ESI MS m/z=1304.8 [M+H]⁺.

Example 14

Compound of Formula V: $R_3$=CH$_3$, $R_4$=H, $R_5$=CH$_3$ and $R_6$=

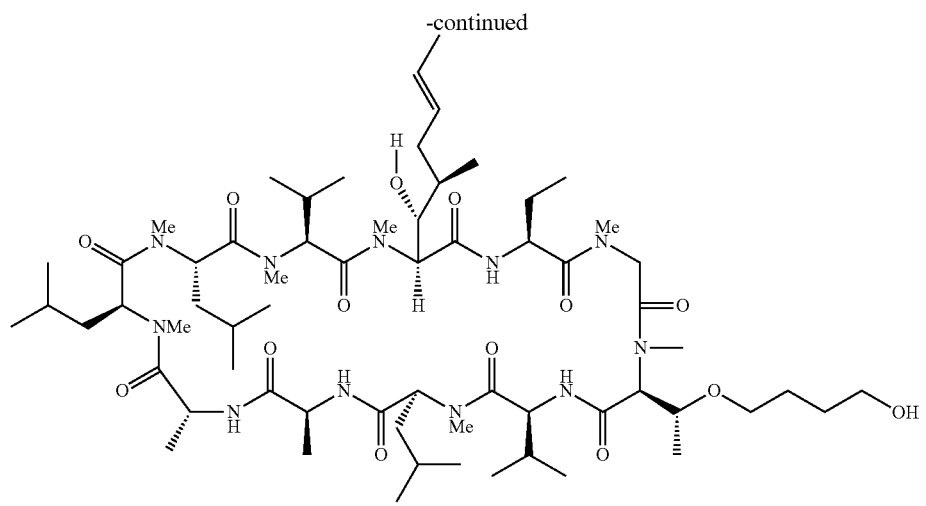

A solution of compound of example 13 (1.3 g, 1 mmol) in MeOH (20 mL) was added K$_2$CO$_3$ (152 mg, 1.1 mmol) at 0° C. After stirred at 0° C. for 2 hrs, the reaction mixture was quenched with 10% citric acid (5 ml). The mixture was added saturated NaHCO$_3$ (50 ml) and extracted with ethyl acetate (50 ml×2). The combined organic layers were washed with saturated NaHCO$_3$ and brine, and then dried over anhydrous Na$_2$SO$_4$. The solvent was removed and the residue was purified by flash chromatography to give the title compound as white solid (1.0 g).

ESI MS m/z=1262.8 [M+H]$^+$.

Example 15

Compound of Formula V: R$_3$=CH$_3$, R$_4$=H, R$_5$=CH$_3$ and R$_6$=

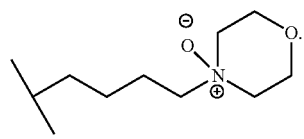

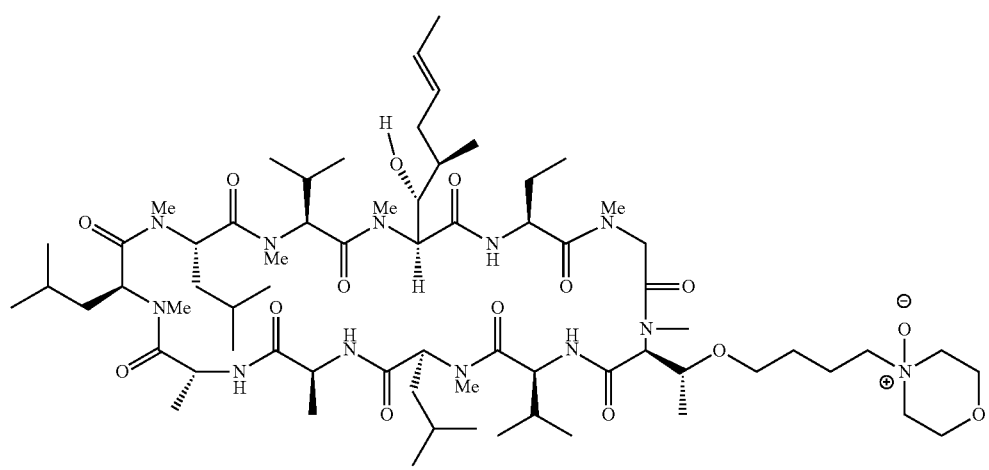

To a solution of compound of example 12 (40 mg, 0.03 mmol) in CH$_2$Cl$_2$ (1 mL) was added m-CPBA (0.033 mmol) at 0° C. The reaction mixture was stirred at 0° C. for 0.5 hr and diluted with CH$_2$Cl$_2$ (10 mL), washed with 10% Na$_2$CO$_3$, brine and dried over Na$_2$SO$_4$. Filtered and the filtrate was concentrated, and then purified by HPLC to give the title compound as white solid (32 mg).

ESIMS m/z=1278.8 [M+H]$^+$.

Example 16

Compound of Formula V: R$_3$=CH$_3$, R$_4$=H, R$_5$=CH$_3$ and R$_6$=

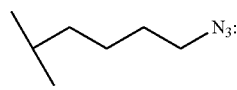

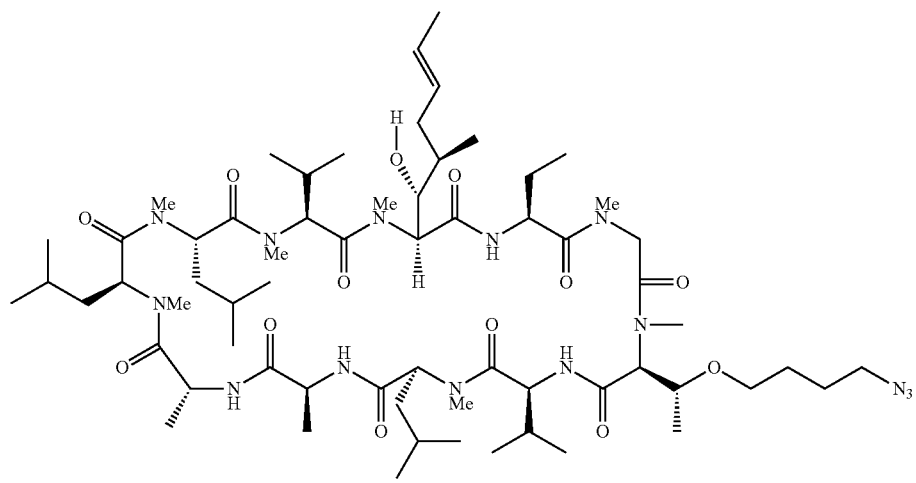

To a 4-drum vial were added compound of example 14 (100 mg, 0.079 mmol), THF (2 mL), triphenylphosphine (excess), DEAD (excess) and DPPA (excess) respectively and the solution was stirred at 50° C. overnight. The crude was passed through a short column by eluting with a mixed solvent MeOH in CH$_2$Cl$_2$ (0~10%) and then further purified by HPLC to afford the title compound (20 mg).

ESI MS m/z=1287.6 [M+H]$^+$.

Example 17

Compound of Formula V: R$_3$=CH$_3$, R$_4$=H, R$_5$=CH$_3$ and R$_6$=

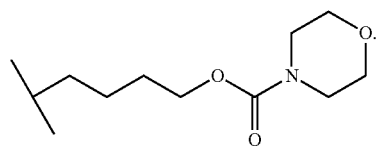

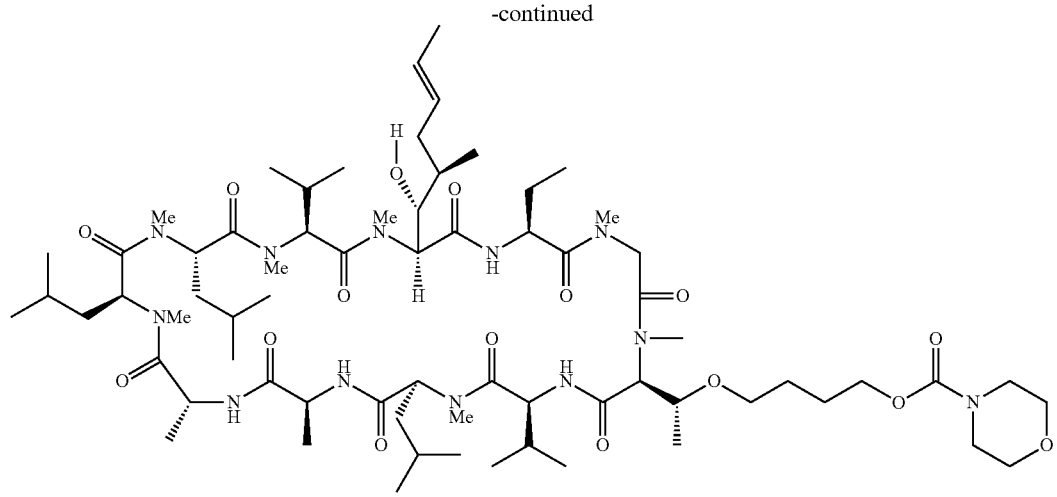

To a 1-dram vial were added compound of example 14 (100 mg, 0.079 mmol), CH$_2$Cl$_2$ (2 mL), CDI (25.6 mg, 0.158 mmol) respectively and the reaction mixture was stirred for 1 hr at room temperature. Morpholine (100 μL) was charged and the reaction was heated at 40° C. for 16 hrs. The crude product mixture was passed through a short column by eluting with a mixed solvent MeOH in CH$_2$Cl$_2$ (0~10%) and then further purified by HPLC to afford the title compound (30 mg).

ESI MS m/z=1375.8 [M+H]$^+$.

Example 18

Compound of Formula V: R$_3$=CH$_3$, R$_4$=H, R$_5$=CH$_3$ and R$_6$=

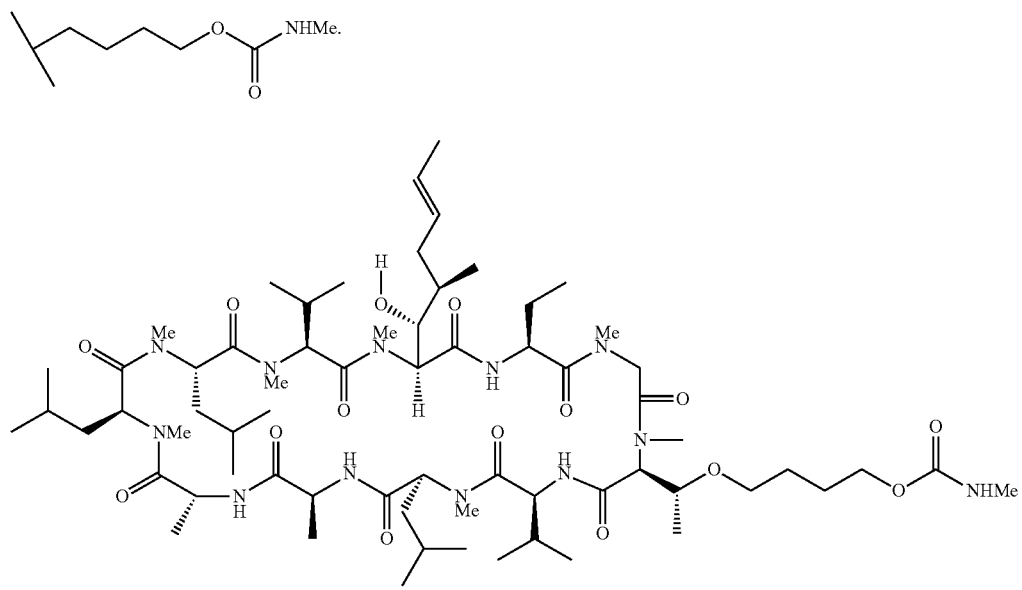

The compound of example 18 was prepared using essential same procedure in the preparation of example 17 (30 mg).

ESI MS m/z=1319.8 [M+H]$^+$.

Example 19

Compound of Formula V: R$_3$=CH$_3$, R$_4$=H, R$_5$=CH$_3$ and R$_6$=

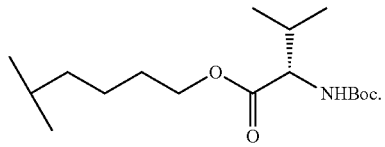

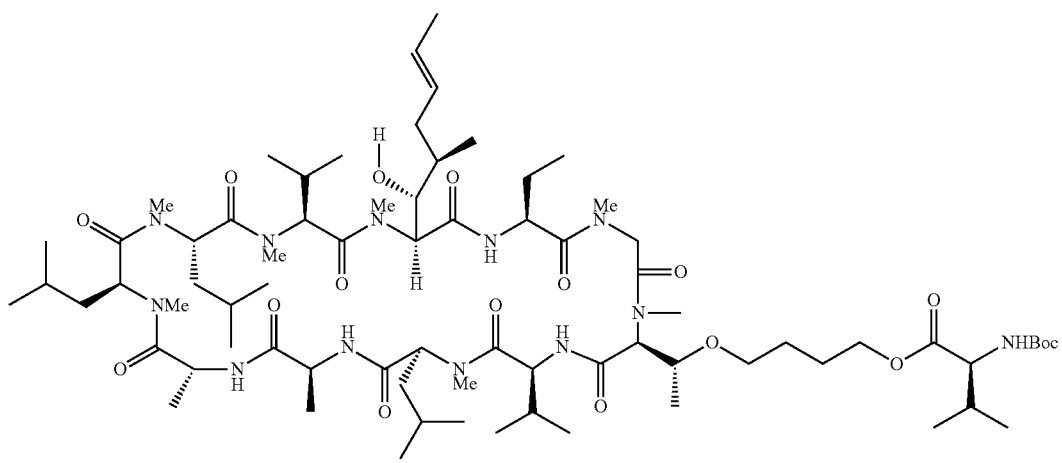

A mixture of compound of example 14 (50 mg, 0.040 mmol), Boc-Val-OH (43 mg, 0.20 mmol), HATU (75 mg, 0.20 mmol), DIPEA (34.5 μL, 0.20 mmol), DMAP (4.8 mg, 0.040 mmol) in CH$_2$Cl$_2$ (1 mL) was stirred at room temperature for 2 hrs. The crude reaction mixture was directly purified on silica gel column to afford the title compound (13.6 mg).

ESI MS m/z=1461.7 [M+H]$^+$.

Example 20

Compound of Formula V: R$_3$=CH$_3$, R$_4$=H, R$_5$=CH$_3$ and R$_6$=

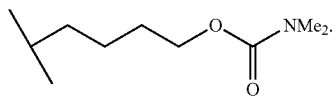

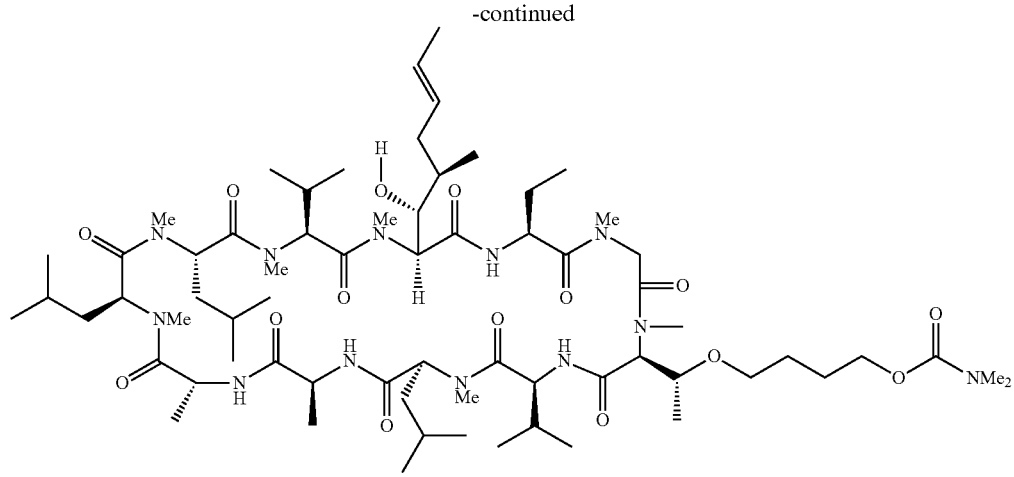

The compound of example 18 was prepared using essential same procedure in the preparation of example 19 (18 mg).

ESI MS m/z=1347.6 [M+H]$^+$.

Example 21

Compound of Formula V: $R_3$=CH$_3$, $R_4$=H, $R_5$=CH$_3$ and $R_6$=

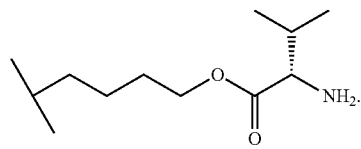

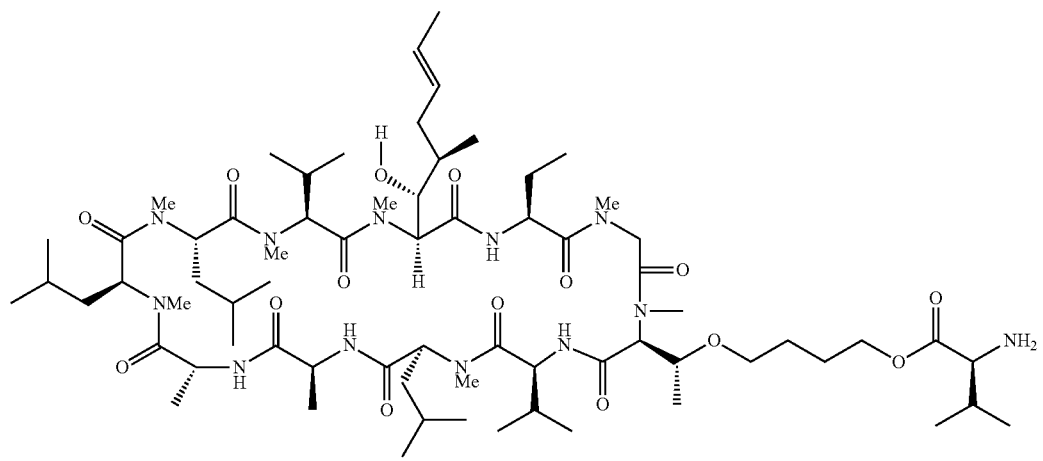

A solution of compound of example 19 (4 mg, 0.0027 mmol) in TFA/CH$_2$Cl$_2$ (2.4 mL, 1:2, v/v) was stirred at room temperature for 20 min. The solvent was removed and the residue was purified by flash chromatography to afford the title compound (3.5 mg).

ESI MS m/z=1361.6 [M+H]$^+$.

Example 22

Compound of Formula V: R$_3$=CH$_3$, R$_4$=H, R$_5$=CH$_3$ and R$_6$=

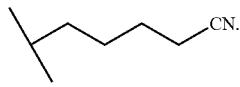

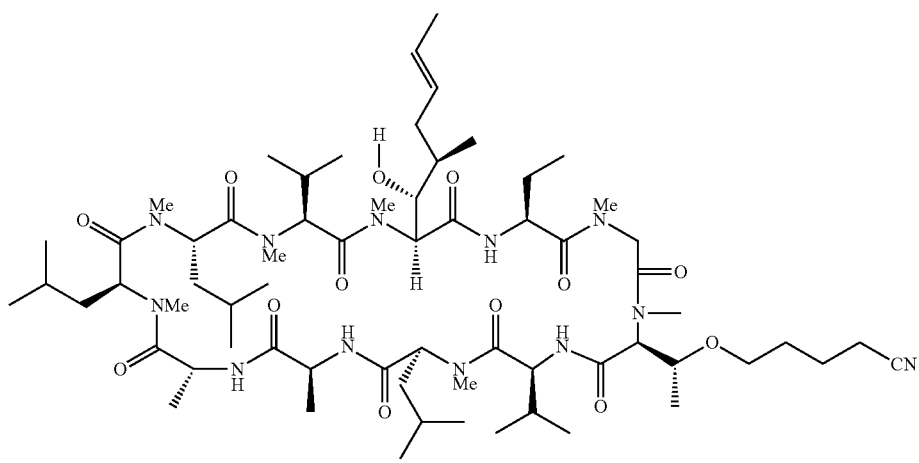

To a 1-dram vial were added the compound of example 14 (20 mg, 0.016 mmol), THF (1 mL), triphenylphosphine (55 mg, 0.21 mmol), DEAD (32.6 μL, 0.21 mmol) and acetone cyanohydrin (43.9 μL, 0.48 mmol) respectively and the solution was stirred for 0.5 h at 50° C. The crude product mixture was passed through a short column by eluting with a mixed solvent MeOH in CH$_2$Cl$_2$ (0~10%). Prep TLC purification afforded the title compound as white foam (12 mg).

ESI MS m/z=1271.8 [M+H]$^+$.

Example 23

Compound of Formula V: R$_3$=CH$_3$, R$_4$=H, R$_5$=CH$_3$ and R$_6$=

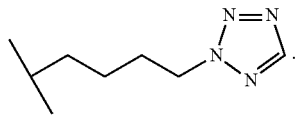

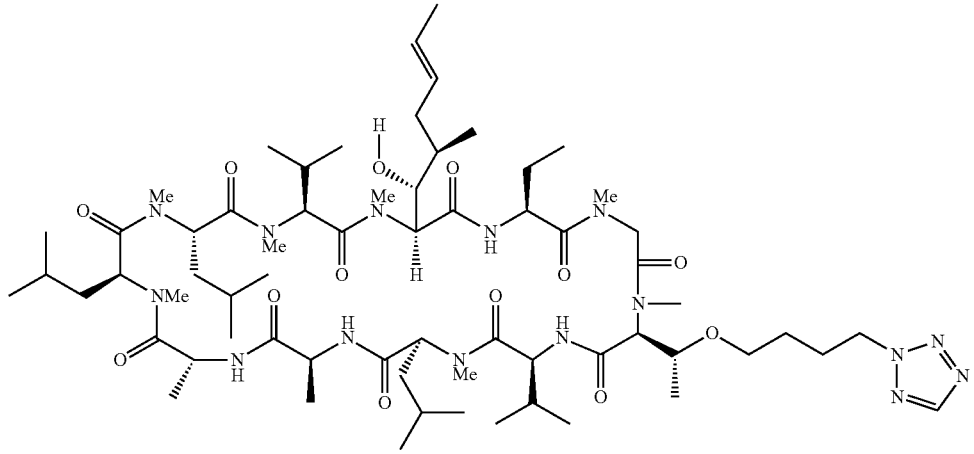

To a 1-dram vial were added the compound of example 14 (20 mg, 0.016 mmol), THF (1 mL), triphenylphosphine (55 mg, 0.21 mmol), DEAD (32.6 µL, 0.21 mmol) and tetrazole in acetonitrile (0.48 mmol) respectively and the solution was stirred for 0.5 h at 50° C. The crude product mixture was passed through a short column by eluting with a mixed solvent MeOH in $CH_2Cl_2$ (0~10%). HPLC purification afforded the title compound as white foam (8 mg).

ESI MS m/z=1314.8 $[M+H]^+$.

Example 24

Compound of Formula V: $R_3$=$CH_3$, $R_4$=H, $R_5$=$CH_3$ and $R_6$=

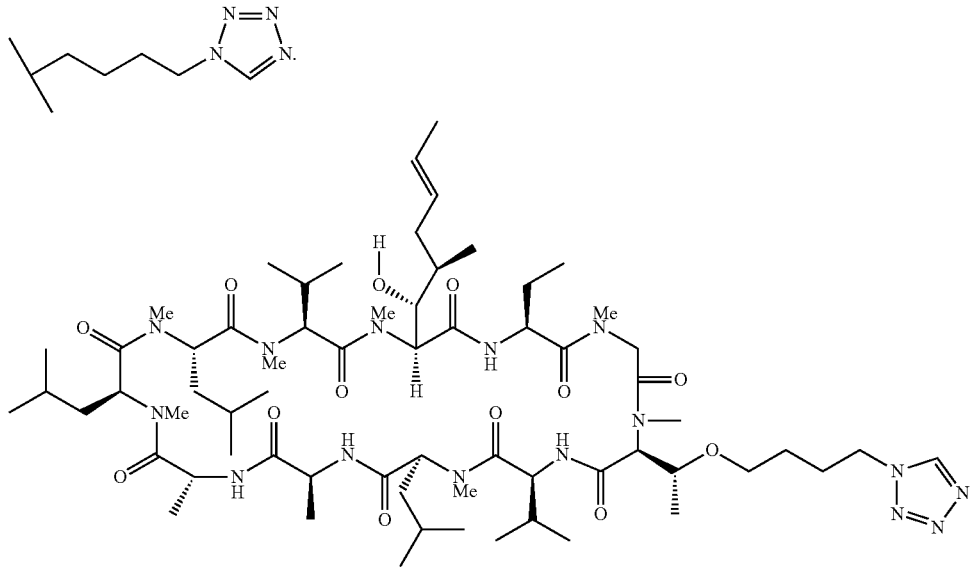

To a 1-dram vial were added the compound of example 14 (20 mg, 0.016 mmol), THF (1 mL), triphenylphosphine (55 mg, 0.21 mmol), DEAD (32.6 µL, 0.21 mmol) and tetrazole in acetonitrile (0.48 mmol) respectively and the solution was stirred for 0.5 h at 50° C. The crude product mixture was passed through a short column by eluting with a mixed solvent MeOH in $CH_2Cl_2$ (0~10%). HPLC purification afforded the title compound as white foam (6 mg).

ESI MS m/z=1314.8 $[M+H]^+$.

Example 25

Compound of Formula V: $R_3$=CH$_3$, $R_4$=H, $R_5$=CH$_3$ and $R_6$=

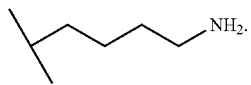

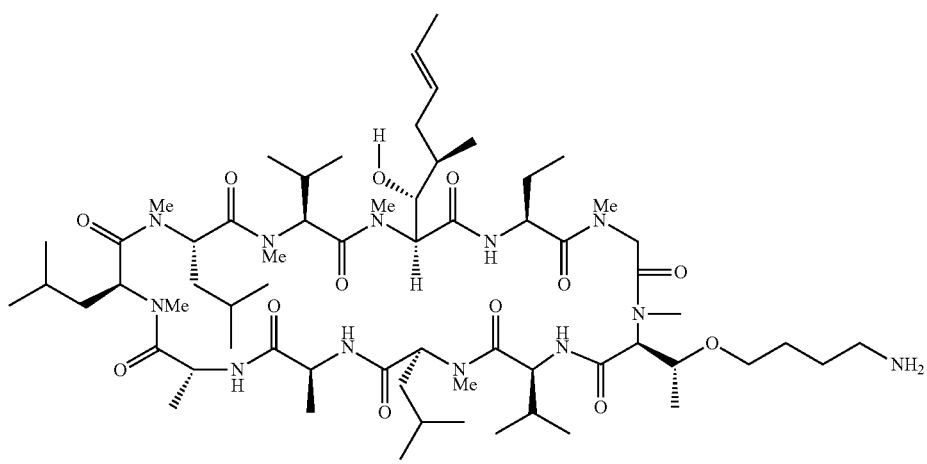

To a 1-dram vial were added compound of example 16 (50 mg, 0.039 mmol), PPh$_3$ (20.4 mg, 0.078 mmol), THF (1 mL) respectively and then the solution was heated at 60° C. for 1 h. Water (14 µL, 0.78 mmol) was added and the reaction was heated at 60° C. for 0.5 h. Solvents were removed and the residue was purified by flash chromatography (MeOH/TEA, 4/1) to give the title compound as white foam (46.8 mg).

ESI MS m/z=1261.4 [M+H]$^+$.

Example 26

Compound of Formula V: $R_3$=CH$_3$, $R_4$=H, $R_5$=CH$_3$ and $R_6$=

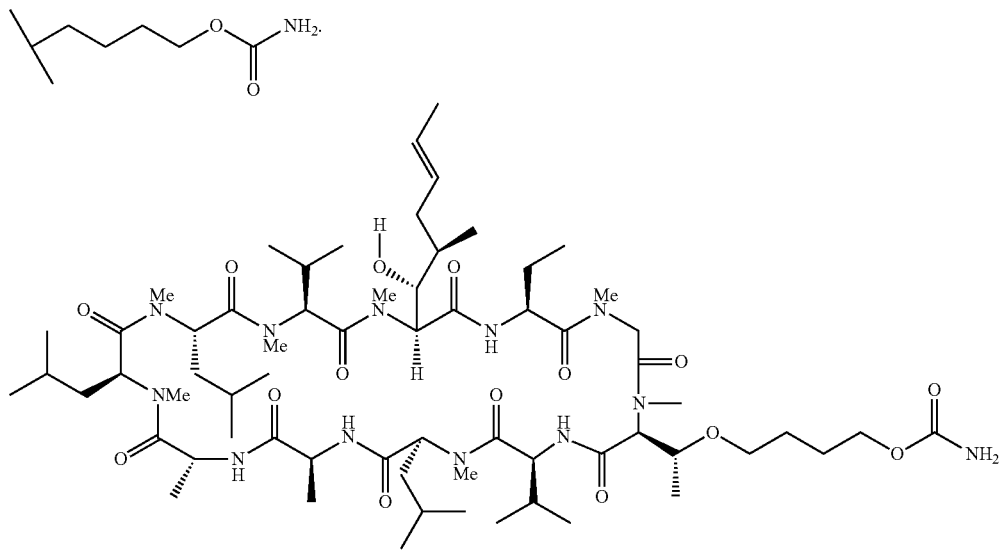

The compound of example 26 was prepared using essential same procedure in the preparation of example 17 (20 mg).

ESI MS m/z=1305.6 [M+H]$^+$.

Example 27

Compound of Formula V: $R_3$=$CH_3$, $R_4$=H,
$R_5$=$CH_3$ and $R_6$=

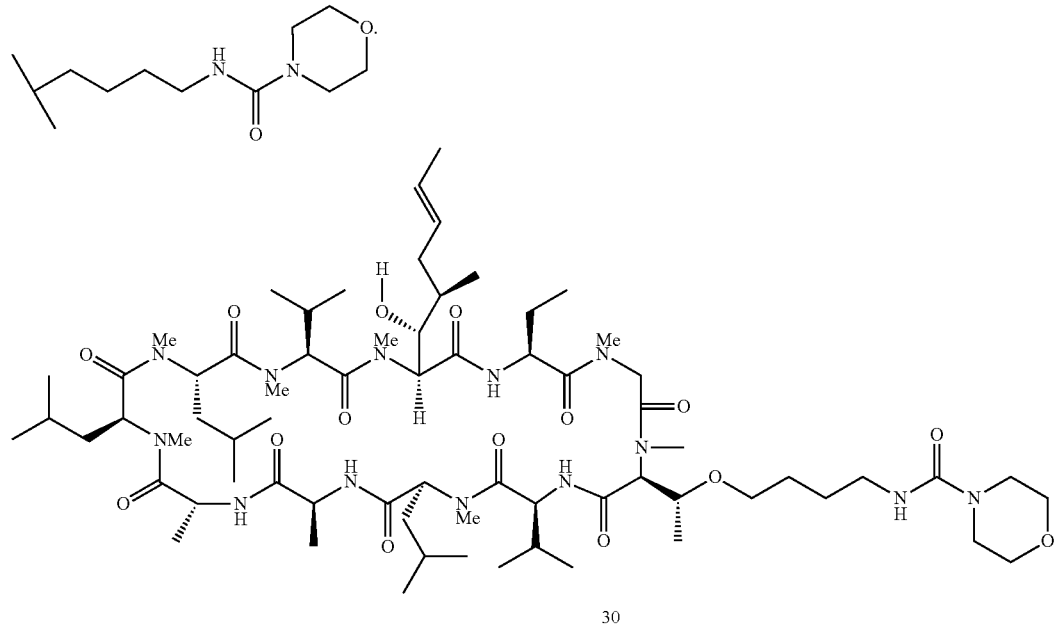

To a 1-dram vial were added triphosgene (19.2 mg, 0.065 mmol), $CH_2Cl_2$ (1 mL), morpholine (16.6 μL, 0.19 mmol) respectively and the turbid mixture was stirred at room temperature for 20 mins followed by addition of the compound of example 25 (20 mg, 0.016 mmol) and DIPEA (50 μL, 0.29 mmol). The mixture was stirred at 40° C. for 1.5 hrs. Solvents were removed and the crude product mixture was purified by HPLC to give the title compound as white foam (6.0 mg).
ESI MS m/z=1374.7 [M+H]$^+$.

Example 28

Compound of Formula V: $R_3$=$CH_3$, $R_4$=H,
$R_5$=$CH_3$ and $R_6$=

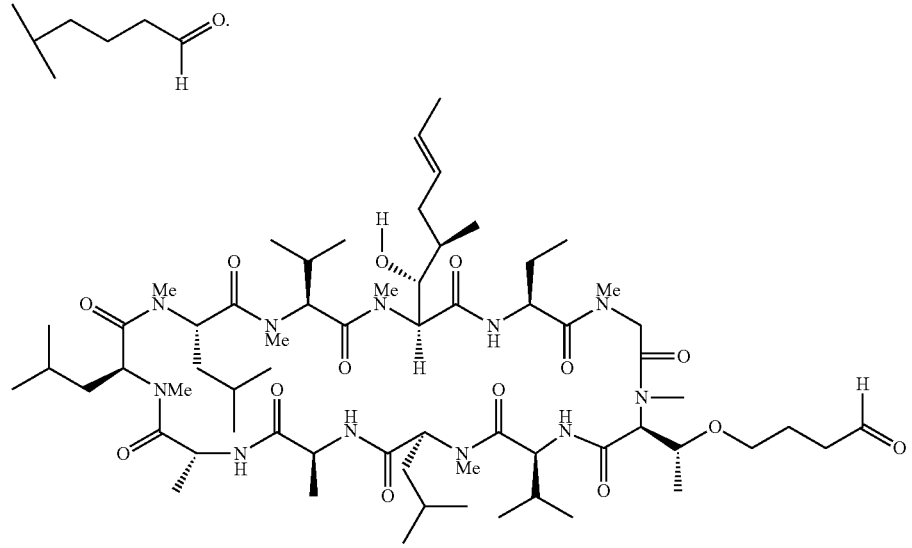

To a 1-drum vial were added compound of example 14 (100 mg, 0.079 mmol), $CH_2Cl_2$ (2 mL), Dess-Martin periodinane (40.3 mg, 0.095 mmol) respectively and the reaction was stirred at room temperature for 20 min. Diluted with $CH_2Cl_2$, washed with saturated $NaHCO_3$, brine, and dried over $Na_2SO_4$. Filtered, concentrated, purified by HPLC to give the title compound as white foam (47 mg).

ESI MS m/z=1260.6 $[M+H]^+$.

Example 29

Compound of Formula V: $R_3$=$CH_3$, $R_4$=H, $R_5$=$CH_3$ and $R_6$=

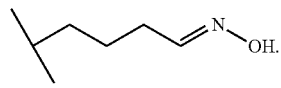

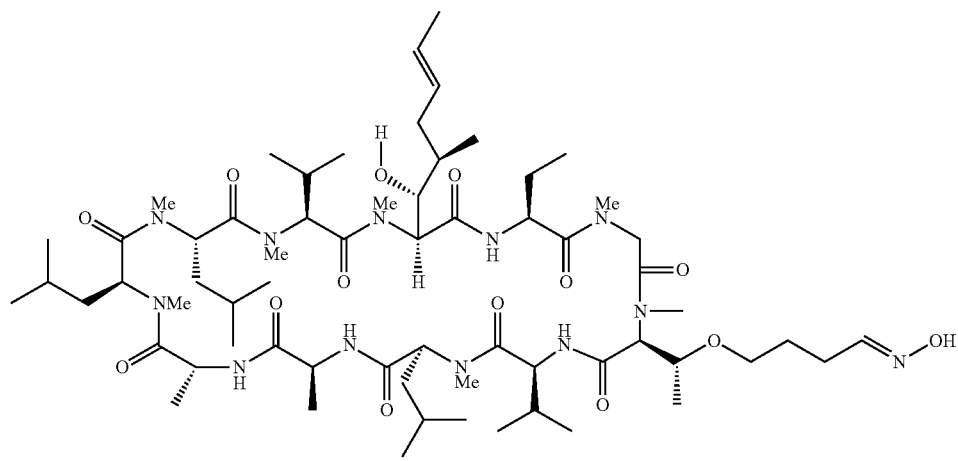

To a 1-drum vial were added the compound of example 28 (10 mg, 0.0079 mmol), EtOH (1 mL), $HONH_2 \cdot HCl$ (excess) respectively and the reaction was stirred at room temperature for 1 hr. The crude reaction mixture was directly purified by HPLC to give the title compound (5.5 mg).

ESI MS m/z=1276.6 $[M+H]^+$.

Example 30

Compound of Formula V: $R_3$=$CH_3$, $R_4$=H, $R_5$=$CH_3$ and $R_6$=

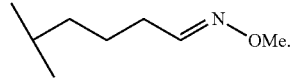

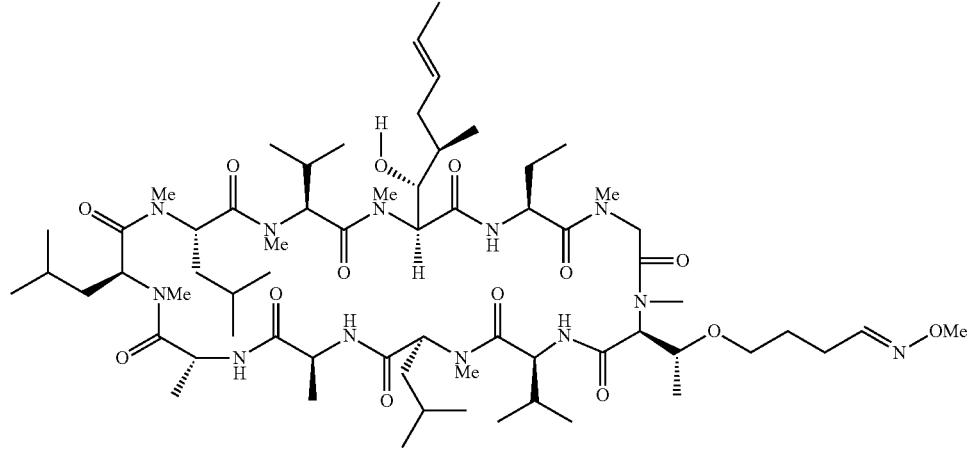
20
The compound of example 30 was prepared using essential same procedure in the preparation of example 29 (9 mg).
ESI MS m/z=1289.8 [M+H]$^+$.
Example 31
Compound of Formula V: $R_3$=CH$_3$, $R_4$=H, $R_5$=CH$_3$ and $R_6$=
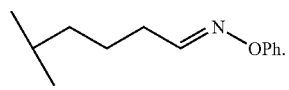
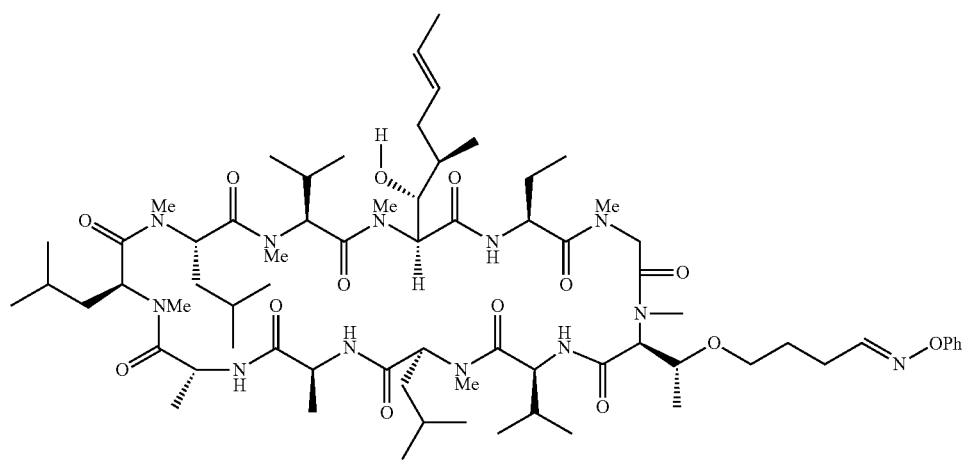
The compound of example 31 was prepared using essential same procedure in the preparation of example 29 (10 mg).
ESI MS m/z=1351.8[M+H]$^+$.

Example 32

Compound of Formula V: $R_3$=$CH_3$, $R_4$=H, $R_5$=$CH_3$ and $R_6$=

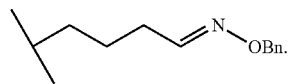

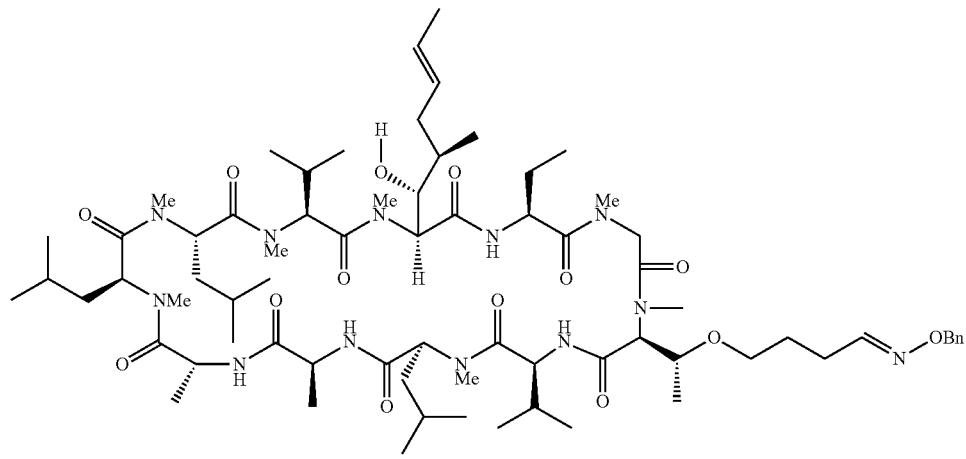

The compound of example 32 was prepared using essential same procedure in the preparation of example 29 (10 mg).

ESI MS m/z=1365.7 [M+H]$^+$.

Example 33

Compound of Formula V: $R_3$=$CH_3$, $R_4$=H, $R_5$=$CH_3$ and $R_6$=

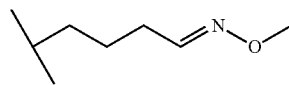

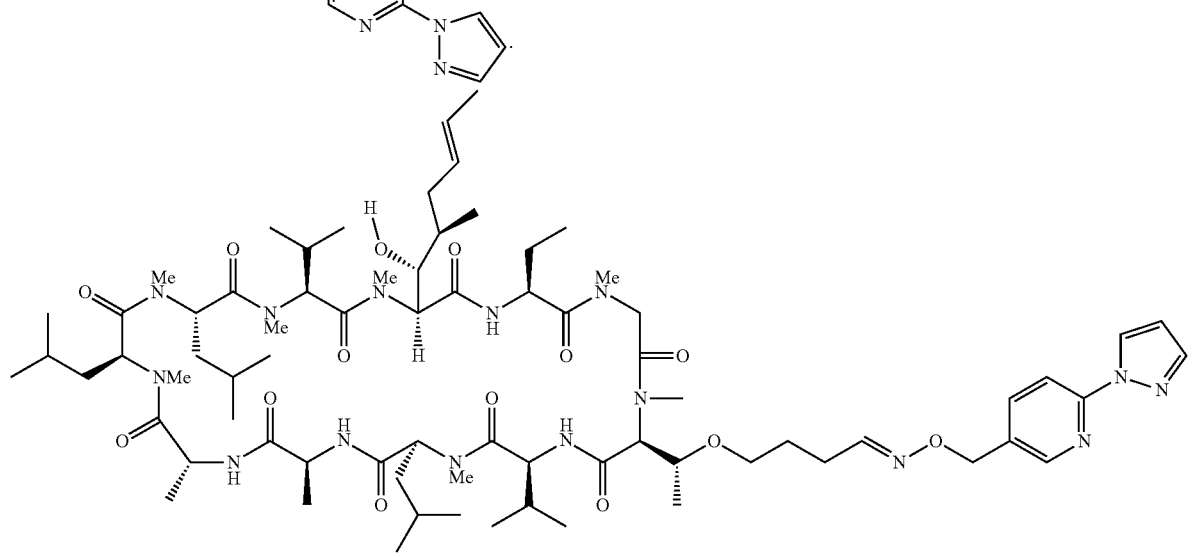

The compound of example 33 was prepared using essential same procedure in the preparation of example 29 (11 mg).

ESI MS m/z=1432.8 [M+H]$^+$.

Example 34
Compound of FormulaV: $R_3$=$CH_3$, $R_4$=H, $R_5$=$CH_3$ and $R_6$=
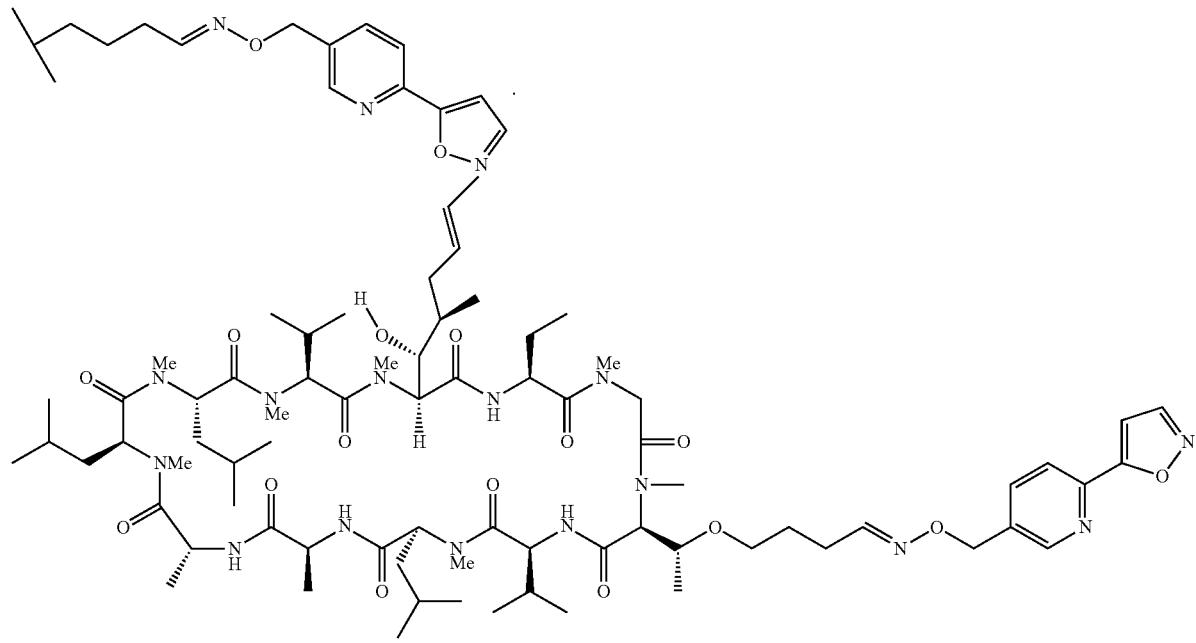
The compound of example 34 was prepared using essential same procedure in the preparation of example 29 (11 mg).
ESI MS m/z=1433.8 $[M+H]^+$.
Example 35
Compound of Formula V: $R_3$=$CH_3$, $R_4$=H, $R_5$=$CH_3$ and $R_6$=
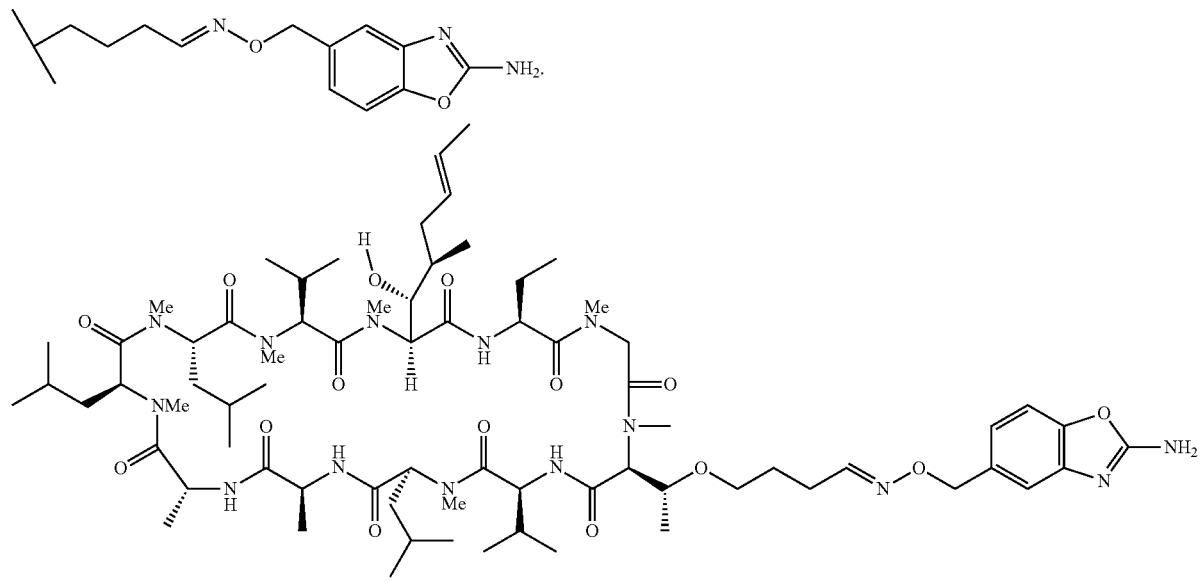

The compound of example 35 was prepared using essential same procedure in the preparation of example 29 (11 mg).
ESI MS m/z=1421.8 [M+H]+.

Example 36

Compound of Formula V: $R_3$=$CH_3$, $R_4$=H, $R_5$=$CH_3$ and $R_6$=

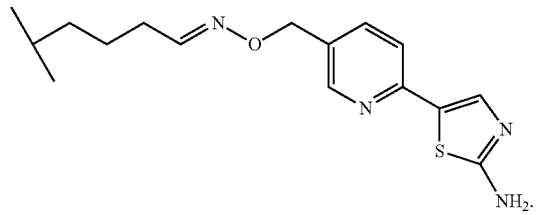

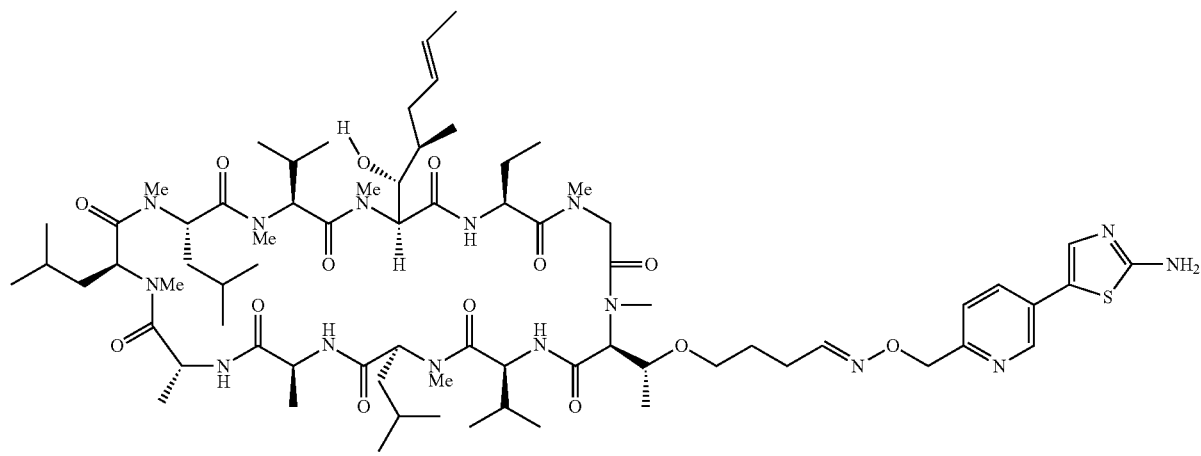

The compound of example 36 was prepared using essential same procedure in the preparation of example 29 (11 mg).
ESI MS m/z=1464.9 [M+H]+.

Example 37

Compound of Formula V: $R_3$=$CH_3$, $R_4$=H, $R_5$=$CH_3$ and $R_6$=

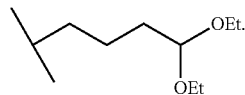

-continued

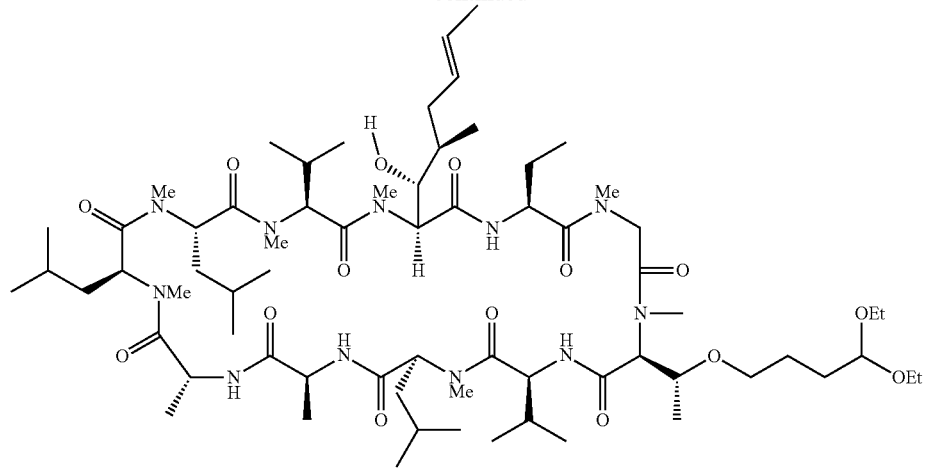

To a 1-dram vial were added the compound of example 28 (10 mg, 0.0079 mmol), EtOH (1 mL), Et$_3$N.HCl (excess) respectively and the reaction was stirred at room temperature for 1 hr. The crude reaction mixture was directly purified by HPLC to give the title compound (8.5 mg).

ESI MS m/z=1334.9 [M+H]$^+$.

Example 38

Compound of Formula V: R$_3$=CH$_3$, R$_4$=H, R$_5$=CH$_3$ and R$_6$=

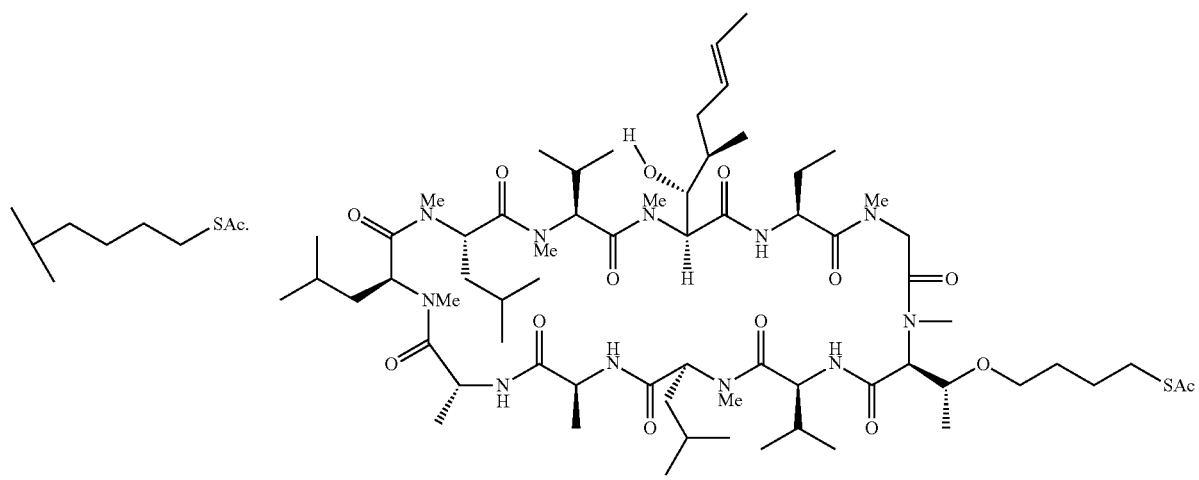

The compound of example 38 was prepared using essential same procedure in the preparation of example 29 (11 mg).

ESI MS m/z=1464.9 [M+H]$^+$.

Example 39

Compound of Formula V: $R_3$=CH$_3$, $R_4$=H, $R_5$=CH$_3$ and $R_6$=

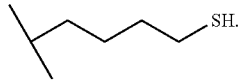

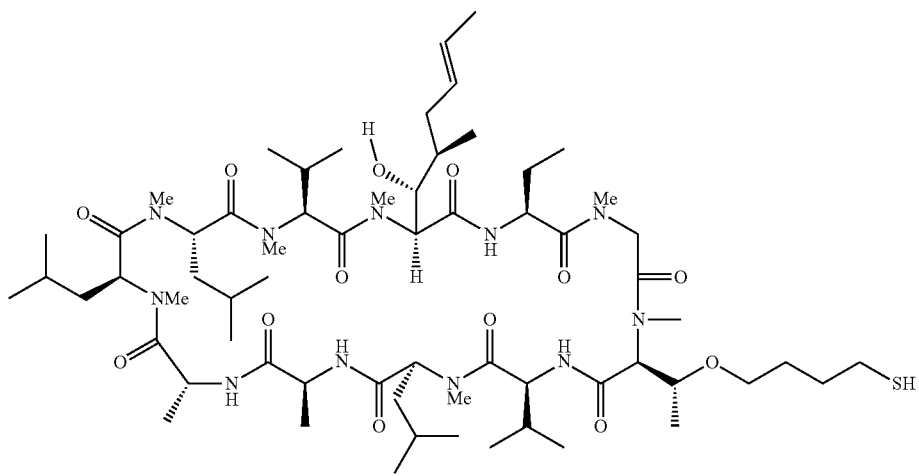

A solution of the compound of example 39 (10 mg, 0.0076 mmol) in 7 N NH$_3$ in MeOH (2 mL) was stirred for 0.5 hr at room temperature. Concentrated and purified by silica gel column (7% MeOH in CH$_2$Cl$_2$) to give the title compound as white solid (6.0 mg).

ESI MS m/z=1278.8 [M+H]$^+$.

Example 40

Compound of Formula V: $R_3$=CH$_3$, $R_4$=H, $R_5$=CH$_3$ and $R_6$=

To a 2-drum vial were added the compound of example 14 (100 mg, 0.079 mmol), CH$_2$Cl$_2$ (1 mL), TEA (48.4 µL, 0.35 mmol) respectively and the solution was cooled to 0° C. followed by addition of mesyl chloride (13.5 µL, 0.174 mmol). The reaction was stirred at 0° C. for 2 hrs and then quenched with water. Extracted with CH$_2$Cl$_2$, dried, concentrated and a portion of crude product 13 mg was purified by silica gel column (10% MeOH in CH$_2$Cl$_2$) to give the title compound as white powder (10 mg).

ESI MS m/z=1340.7 [M+H]$^+$.

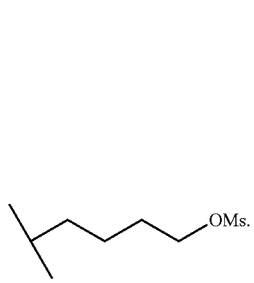

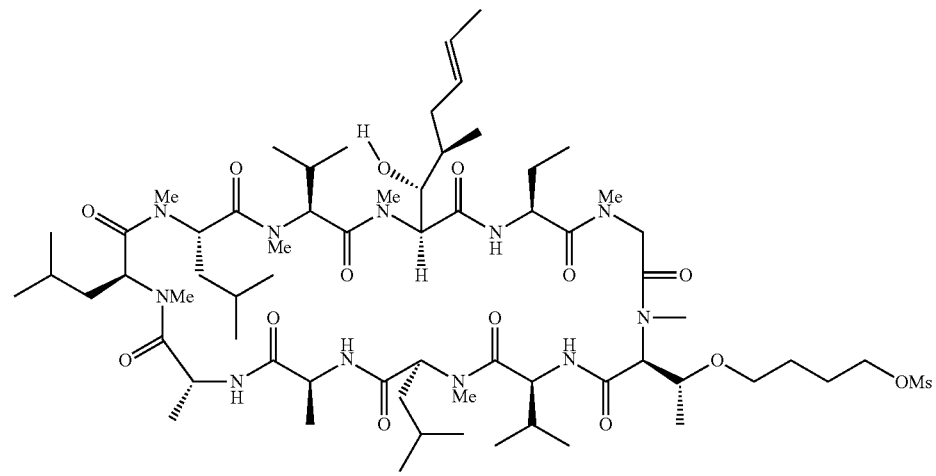

Example 41

Compound of Formula V: R$_3$=CH$_3$, R$_4$=H, R$_5$=CH$_3$ and R$_6$=

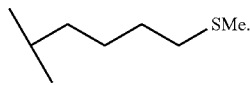

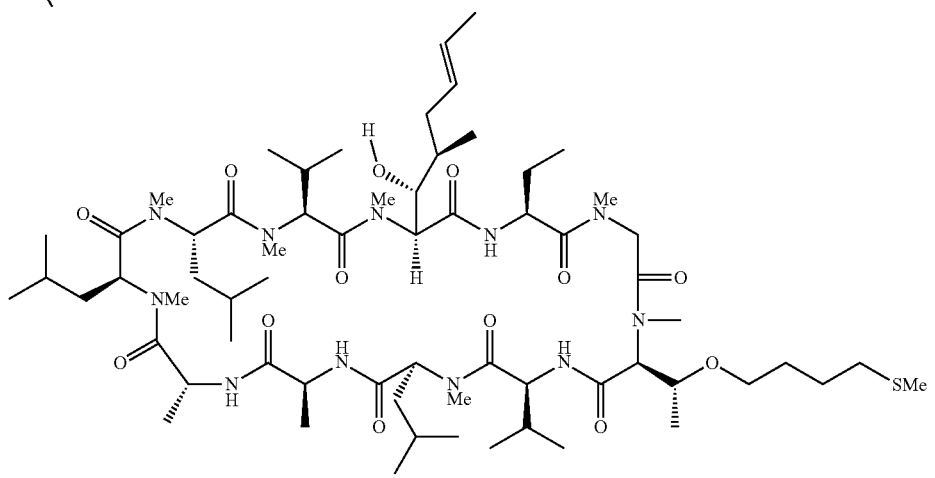

To a 1-drum vial were added the compound of example 40 (45 mg, 0.034 mmol), DMF (1.5 mL) and NaSMe (excess) respectively and the reaction was stirred at 0° C. for 0.5 hr. Diluted with CH$_2$Cl$_2$ and then quenched with acetic acid. Extracted with CH$_2$Cl$_2$, Washed with water, dried, concentrated and purified by Prep TLC to give the title compound as white powder (26.2 mg).

ESI MS m/z=1292.6 [M+H]$^+$.

Example 42

Compound of Formula V: R$_3$=CH$_3$, R$_4$=H, R$_5$=CH$_3$ and R$_6$=

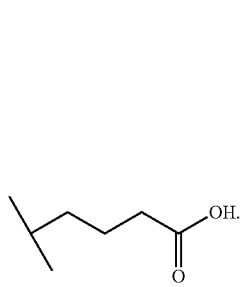

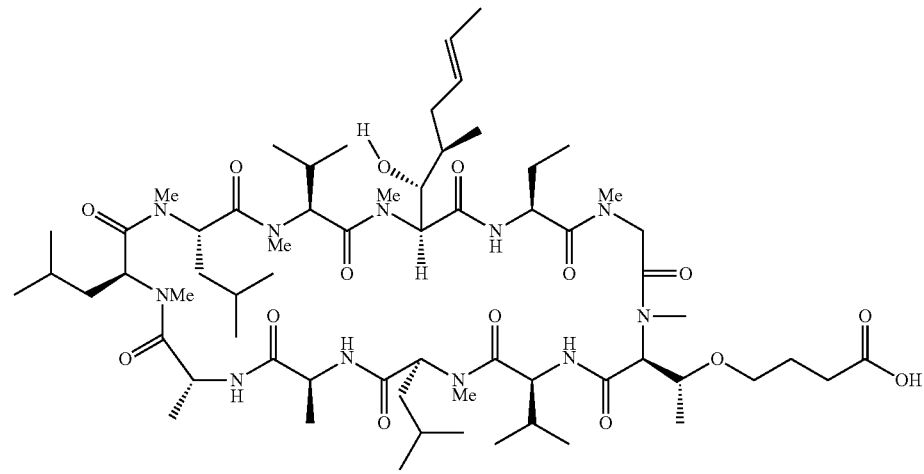

To a 2-drum vial were added the compound of example 28 (104 mg, 0.083 mmol), acetonitrile (2 mL), 2-methyl-2-butene (0.5 mL), a freshly prepared solution of 45 mg (0.4 mmol) of 80% NaClO$_2$, 45 mg (0.3 mmol) of NaH$_2$PO$_4$.H$_2$O, and 1.5 mL of H$_2$O. After stirred for 15 min at 0° C., the reaction was diluted with CH$_2$Cl$_2$, washed with brine. Dried, concentrated, purified by flash chromatography eluting with MeOH/CH$_2$Cl$_2$ (1~10%) to give the title compound as white foam (70 mg).

ESI MS m/z=1276.6 [M+H]$^+$.

Example 43

Compound of Formula V: R$_3$=CH$_3$, R$_4$=H,
R$_5$=CH$_3$ and R$_6$=

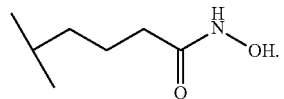

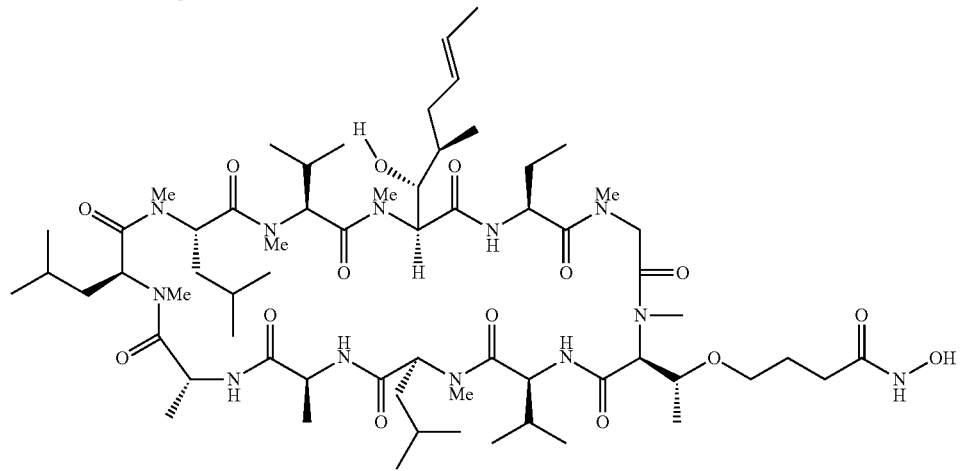

A mixture of the compound of example 42 (20 mg, 0.016 mmol), HONH$_2$.HCl (11 mg, 0.16 mmol), HATU (60.8 mg, 0.16 mmol), and DIPEA (56 μL, 0.32 mmol) in CH$_2$Cl$_2$ (1 mL) was stirred at room temperature for 0.5 hr. Concentrated and purified by HPLC to give the title compound as white foam (4.4 mg).
ESI MS m/z=1291.6 [M+H]$^+$.

Example 44

Compound of Formula V: R$_3$=CH$_3$, R$_4$=H,
R$_5$=CH$_3$ and R$_6$=

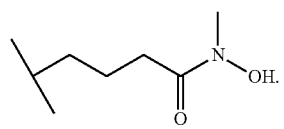

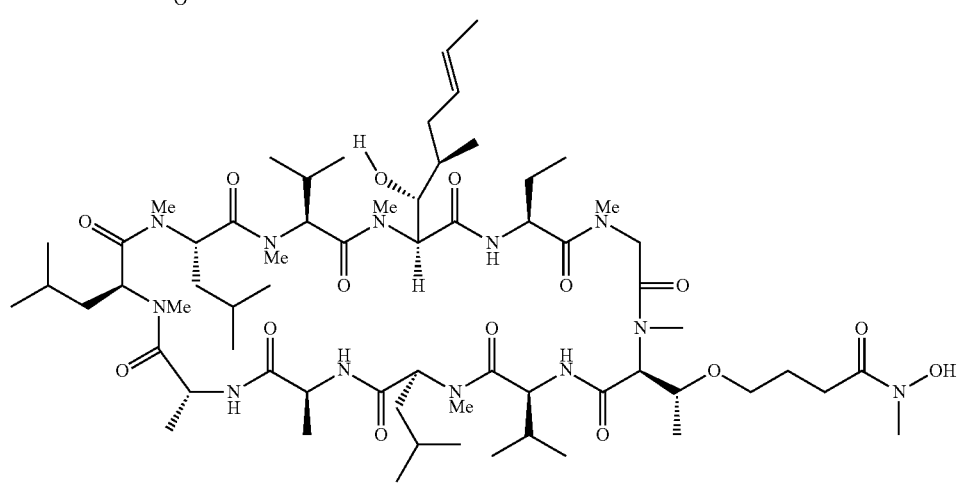

The compound of example 44 was prepared using essentially the same procedure in the preparation of example 43 (5.0 mg).
ESI MS m/z=1305.7 [M+H]$^+$.

Example 45

Compound of Formula V: $R_3$=CH$_3$, $R_4$=H, $R_5$=CH$_3$ and $R_6$=

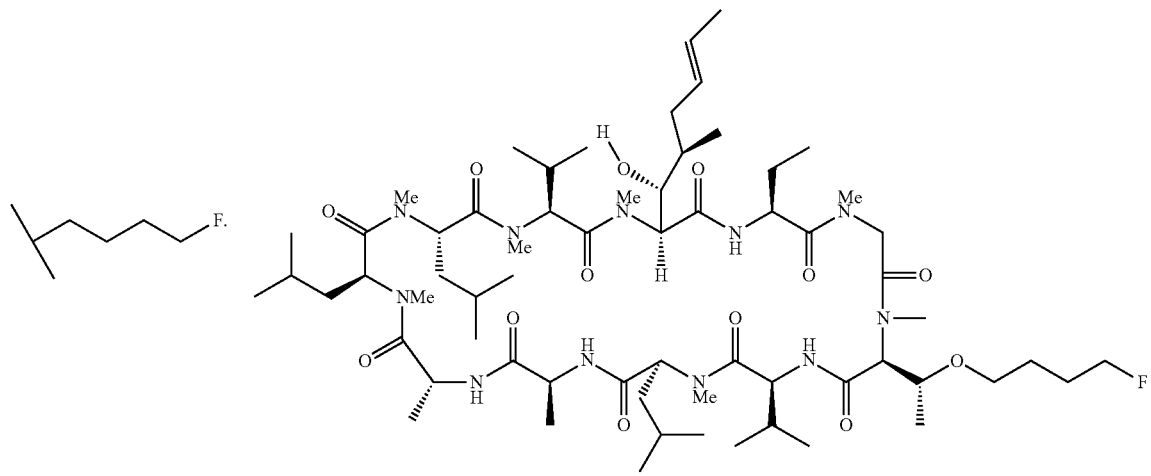

To a 10 mL Schlenk tube were added the compound of example 14 (15 mg, 0.011 mmol), CH$_2$Cl$_2$ (1 mL), and the solution was cooled to −78° C. under N$_2$ followed by addition of DAST (6.1 μL, 0.046 mmol). The reaction was warmed to room temperature slowly and stirred overnight. Quenched with water, extracted with CH$_2$Cl$_2$, dried, concentrated and purified by Prep TLC (4% MeOH in CH$_2$Cl$_2$) to give the title compound as white foam (7.0 mg).
ESIMS m/z=1264.4 [M+H]$^+$.

Example 46

Compound of Formula V: $R_3$=CH$_3$, $R_4$=H, $R_5$=CH$_3$ and $R_6$=

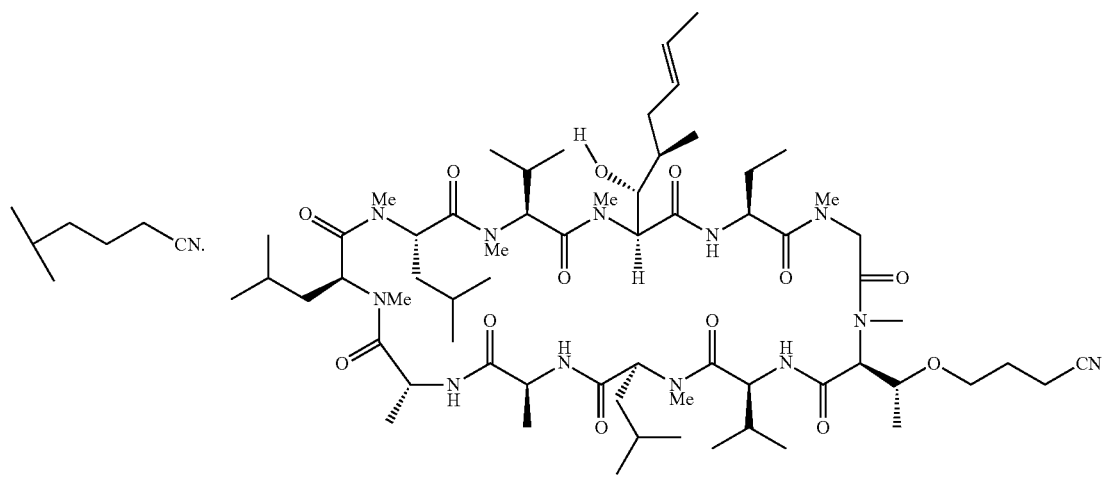

To a 1-drum vial were added the compound of example 29 (10 mg, 0.0078 mmol), CH₂Cl₂ (1 mL), CDI (3.8 mg, 0.024 mmol), TEA (11 μL, 0.078 mmol) respectively and the solution was stirred at room temperature for 19 hrs. Concentrated and purified by Prep TLC (5% MeOH in CH₂Cl₂) to give the title compound as white foam (6.2 mg).

ES IMS m/z=1257.8 [M+H]⁺.

Example 47

Compound of Formula V: R₃=allyl, R₄=H, R₅=CH₃ and R₆=

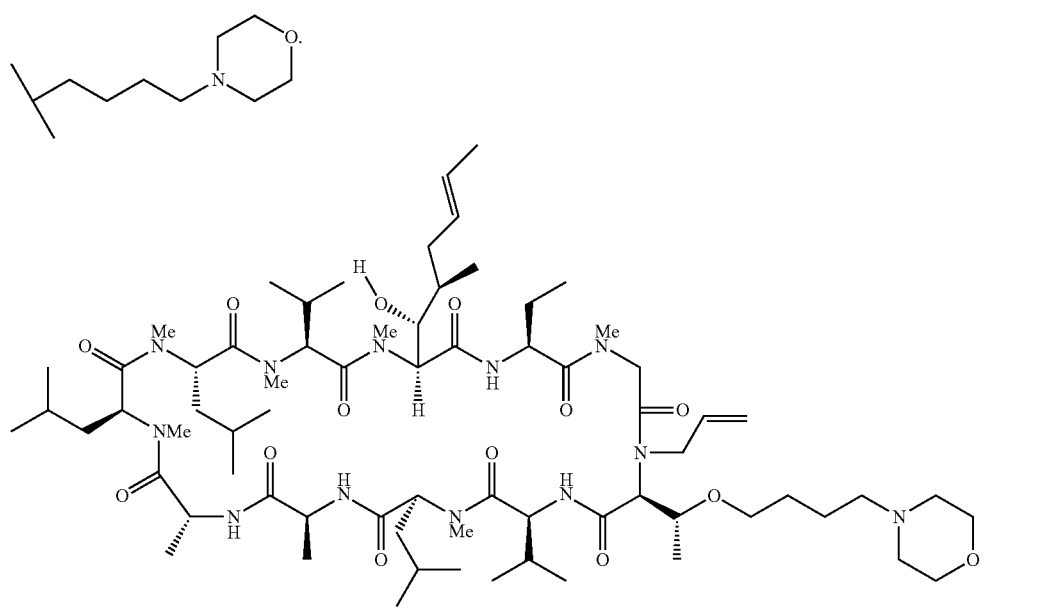

Step 47a: Compound of Formula (2-2) where R₃ is H, R₄=H, R₅=CH₃ and R₆ is ═

To a 500 mL round-bottomed flask were added the compound of formula (2-2) where R₃ is H and R₆ is allyl, which was prepared in step 2a (6.4 g, 24.7 mmol), Cis-1,4-Diactoxy-2-butene (42.5 g, 247 mmol), Hoveyda-Grubbs 2$^{nd}$ generation catalyst (770 mg, 1.23 mmol) and the flask was capped with a rubber septum stopper. Vacuum was applied and backflashed with N₂ three times. Degassed DCE (250 mL) was added and the reaction was heated at 40° C. for 18 h. Concentrated and charged with water (100 mL). The biphasic mixture was cooled to 0° C. followed by addition of 2 N NaOH (12.4 mL). The mixture was stirred for 10 min at 0° C., and then transferred to a separational funnel. Water (150 mL) and Et₂O (300 mL) were added. The ether layer was discarded and the aqueous layer was extracted again with Et₂O (200 mL). The aqueous layer was poured into 1 L flask and acidified with 2 N HCl (20 mL) at 0° C. Extracted with Et₂O (250 mL×3) and the combined organic layers were washed with brine, dried, concentrated and purified by flash chromatography to give the title compound as a yellow foam (6.5 g, 79.5% yield).

ESI MS m/z=332.25 [M+H]⁺.

Step 47b: Compound of Formula (2-2) where R₃ is H, R₄=H, R₅=CH₃ and R₂ is

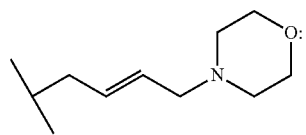

To a 100 mL round-bottomed flask were added the compound of formula (2-2) where R₃ is H and R₆ is

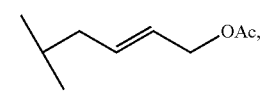

which was prepared in step 47a (3.4 g, 10.2 mmol), Pd₂(dba)₃ (748 mg, 0.8 mmol), dppe (650 mg, 1.6 mmol), THF (50 mL), morpholine (8.7 g, 100 mmol) under N₂ and the mixture was stirred at 65° C. for 2 hrs. Solvents were removed and the residue was purified by flash chromatography to give the title compound as yellow foam (3.4 g (contaminated with morpholine).

ESI MS m/z=359.30 [M+H]⁺.

Step 47c: Compound of Formula (2-2) where R₃ is H, R₄=H, R₅=CH₃ and R₆ is

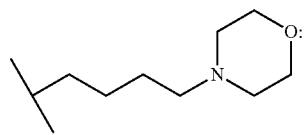

A mixture of compound of formula (2-2) where R₃ is H and R₂ is

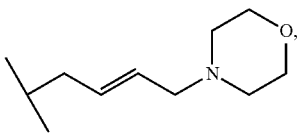

which was prepared in step 47b (1.7 g, 4.7 mmol) and 10% Pd/C (110 mg) in MeOH (50 mL) was stirred at room temperature under $H_2$ for 20 hrs followed by passing through a pad of celite. Concentrated to give the title compound as an oil (1.7 g, 100% yield).

ESI MS m/z=361.35 [M+H]$^+$.

Step 47d: Compound of Formula (3-3) where $R_3$ is allyl, $R_4$=H, $R_5$=$CH_3$ and $R_6$ is

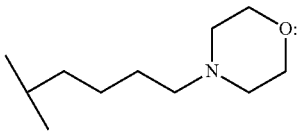

To a 25 mL round-bottomed flask were added the compound of formula (2-2) where $R_3$ is H and $R_6$ is

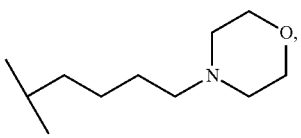

which was prepared in step 47c (238 mg, 0.66 mmol), THF (2 mL), $^t$BuOK (78.5 mg, 0.70 mmol), Pd$_2$(dba)$_3$ (60.4 mg, 0.066 mmol), dppe (52.6 mg, 0.13 mmol), and allylic tert-butoxy carbonate (418 mg, 2.64 mmol). The solution was stirred at 75° C. for 0.5 h. The reaction mixture was then cooled to room temperature, diluted with EtOAc, filtered through a pad of celite. The filtrate was concentrated and purified by flash chromatography (Acetone/Hexane, 0-10%, v/v) to give the compound as an oil (148 mg, 51% yield).

ESI MS m/z=441.27 [M+H]$^+$.

To a solution of the above compound (138 mg, 0.31 mmol) in $CH_2Cl_2$ (3 mL) was added TFA (2 mL) at 0° C. dropwise. After stirred at 0° C. for 2 hrs, the solvents were removed in vacuo and the residue was dissolved in $CH_2Cl_2$. Washed with 10% $Na_2CO_3$, brine and dried over anhydrous $Na_2SO_4$, filtered, concentrated to give the title compound as yellow oil (111 mg in 100% yield).

ESI MS m/z=341.27 [M+H]$^+$.

Step 47e: Compound of Formula (3-1) where $R_p$ is TMS

To a solution of compound of formula (2-1)(3.5 g, 3.16 mmol) and DIPEA (1.22 g, 9.5 mmol) in 1,4-dioxane (140 mL) was added a solution of Boc$_2$O (1.37 g, 6.32 mmol) in 1,4-dioxane (30 mL) at 0° C. dropwise. After stirred at 0° C. for 10 mins and room temperature for 2 hrs, the reaction was quenched with MeOH. The solvents were removed in vacuo and the residue was dissolved in EtOAc. Washed with saturated KHSO$_4$ solution, brine and dried over anhydrous Na$_2$SO$_4$, the solvent was removed and the residue was purified by flash chromatography (MeOH/CH$_2$Cl$_2$, 0-10%, v/v) to give the compound 3.3 g as white foam in 87% yield.

ESI MS m/z=1208.37 [M+H]$^+$.

To a solution of the above compound (1.2 g, 1.0 mmol), 1-methylimidazole (246 mg, 3 mmol) and N, O-bis(trimethylsilyl)acetamide (2.03 g, 10 mmol) in $CH_2Cl_2$ (2 mL) was added TMSCl (107 mg, 1.0 mmol) at 0° C. dropwise. After stirred at 0° C. for 10 mins and room temperature for 1 hr, the reaction was quenched with MeOH. The solvents were removed in vacuo and the residue was dissolved in EtOAc, washed with saturated KHSO$_4$ solution, brine and dried over anhydrous Na$_2$SO$_4$, filtered, concentrated, and purified by flash chromatography (Hexanes/Acetone, 90-50%, v/v) to give the title compound as white foam (921 mg, 72% yield).

ESIMS m/z=1280.45 [M+H]$^+$.

Step 47f: Compound of Formula (3-2)

To a solution of compound of formula (3-1) where $R_p$ is TMS (0.66 g, 0.52 mmol) in THF (10 mL) and water (5 mL) at 0° C. was added LiOH solution (2.0 mmol, 4 mL 0.5 M solution in water). After stirred at 0° C. for 1 h, the reaction mixture was diluted with EtOAc, washed with saturated KHSO$_4$ solution, brine and dried over anhydrous Na$_2$SO$_4$. Filtered, the filtrate was concentrated to give the title compound as a white foam (603 mg).

ESI MS m/z=1194.21 [M+H]$^+$.

Step 47g: Compound of Formula (3-4) where $R_3$ is allyl and $R_6$ is

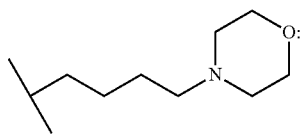

To a solution of compound of formula (3-2), which was prepared in step 47f (500 mg, 0.40 mmol), compound of formula (3-3) where $R_3$ is allyl and $R_6$ is

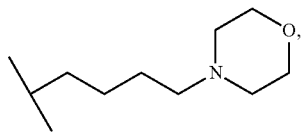

which was prepared in step 47d (110 mg, 0.32 mmol) and DMAP (138 mg, 1.12 mmol) in DMF (2 mL) was added HATU (307 mg, 0.81 mmol) at room temperature. After stirred at room temperature for 48 hrs and 40° C. for 4 hrs, the reaction mixture was quenched with aqueous saturated NaHCO$_3$. The resulting mixture was extracted with $CH_2Cl_2$. The organic layer was washed with saturated KHSO$_4$ solution, brine and dried over anhydrous Na$_2$SO$_4$, filtered, concentrated, and purified by flash chromatography ($CH_2Cl_2$/MeOH, 100-90%, v/v) to give the title compound 120 mg as white foam in 25% yield.

ESI MS m/z=1516.71 [M+H]$^+$.

Step 47h: Compound of Formula (3-5) where $R_3$ is allyl and $R_6$ is

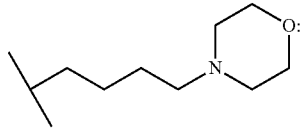

To a solution of compound of formula (3-4) where $R_3$ is allyl and $R_6$ is

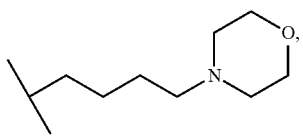

which was prepared in step 47g (60 mg, 0.04 mmol), Dimedone (11.2 mg, 0.08 mmol) in THF (1 mL) was added Pd(Ph$_3$P)$_4$ (4.6 mg, 0.004 mmol) at room temperature. The reaction mixture was stirred at room temperature for 20 mins and diluted with EtOAc. Filtered through a pad of celite, the filtrate was concentrated and the residue was purified by flash chromatography (CH$_2$Cl$_2$/MeOH, 5%, v/v) to give the compound 24 mg as an oil in 40% yield.

ESI MS m/z=1476.47 [M+H]$^+$.

To a solution of the above compound (24 mg, 0.016 mmol) in CH$_2$Cl$_2$ (1 mL) was added TFA (1 mL) at 0° C. dropwise. After stirred at 0° C. for 2 h, the solvents were removed in vacuo and the residue was dissolved in CH$_2$Cl$_2$, then washed with saturated aqueous NaHCO$_3$ solution, brine and dried over anhydrous Na$_2$SO$_4$, filtered, concentrated to give the title compound as a pale yellow foam (14 mg, 64% yield).

ESI MS m/z=1376.47 [M+H]$^+$.

Step 47i: Compound of Formula (3-6) where R$_3$ is allyl and R$_6$ is

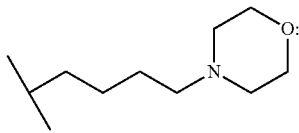

To a solution of TFFH (5.4 mg, 0.021 mmol), 2,4,6-sym-collidine (2.5 mg, 0.021 mmol) in CH$_2$Cl$_2$ (50 mL) was added Compound of formula (3-5) where R$_3$ is allyl and R$_6$ is

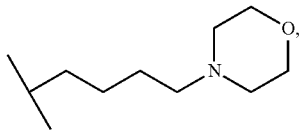

which was prepared in step 47h (14 mg, 0.010 mmol) in CH$_2$Cl$_2$ (20 mL) at room temperature. The solution was stirred at room temperature for 16 h. The reaction mixture was then washed with aqueous KHSO$_4$, 10% aqueous Na$_2$CO$_3$, brine, dried over anhydrous Na$_2$SO$_4$, filtered, concentrated, and purified by HPLC to give the title compound 2.2 mg as a white foam 16% yield.

ESI MS m/z=1357.54 [M+H]$^+$.

Example 48

Compound of Formula V: R$_3$=CH$_3$, R$_4$=CH$_3$, R$_5$=H and R$_6$=allyl

The compound of example 48 was prepared using essentially same procedure in the preparation of the compound of example 2 with the compound from step 1d and the compound of formula (2-2) where R$_3$=CH$_3$, R$_4$=CH$_3$, R$_5$=H and R$_6$=allyl.

MS (ESI): 1230.7 m/z (M+1).

Example 49

Compound of Formula VI: R$_3$=CH$_3$, R$_4$=H, R$_5$=CH$_3$ and R$_6$=H

Step 49a: Compound of Formula (4-1)

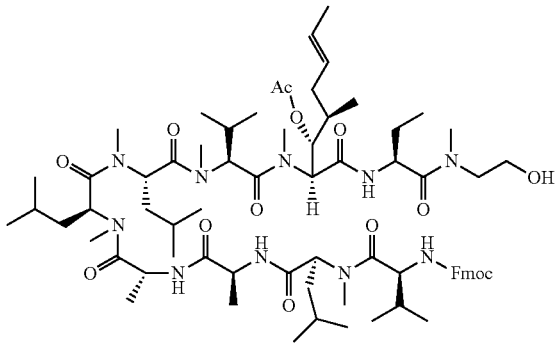

Compound of formula (1-3) (61 g, 53 mmole) was dissolved in isopropanol (450 ml) and methanol (50 ml), and NaBH$_4$ (9.0 g, 266 mmole) was added during 1 hrs 1 at 0° C. The reaction mixture was stirred at room temperature for 2 hrs. Ethyl acetate (50 ml) was added and the mixture was stirred at room temperature for 30 min and then quenched with 1N HCl at 0° C. The pH of mixture was adjusted to pH~9 by adding saturated NaHCO$_3$ and Na$_2$CO$_3$. Extracted with ethyl acetate and washed with saturated NaHCO$_3$ and brine. Dried over Na$_2$SO$_4$ and the solvent was removed. The residue was dried on vacuum to give the alcohol compound (59.7 g). Then the resulted compound was dissolved in DCM (500 ml). FmocCl (11.7 g, 45 mmole) and DIPEA (12.9 g, 100 mmol) were added at 0° C. The reaction mixture was stirred at 0° C. for 2 hrs. Diluted with DCM (500 ml) and washed with 10% citric acid, saturated NaHCO$_3$ and brine. Dried over Na$_2$SO$_4$ and the solvent was removed. The residue was purified on by silica gel column to give the compound of formula (4-1) (46 g). MS:

(ESI) m/z (M+H) 1343.8.

Step 49b: Compound of Formula (4-2)

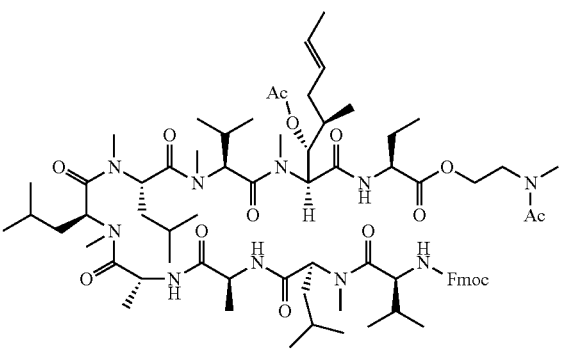

Compound of formula (4-1) (13.4 g, 10 mmole) was dissolved in isopropanol (100 ml). Methanesulfonic acid (100 mmole) was added at room temperature. The reaction mixture was stirred at 50° C. for 8 hrs. The reaction mixture was condensed to ~40 ml and was diluted with ethyl acetate (500 ml) and quenched with saturated NaHCO$_3$. The pH of the mixture was further adjusted to ~9 by adding saturated Na$_2$CO$_3$. The organic layer was separated and washed with brine. Dried over Na$_2$SO$_4$ and the solvent was removed. The residue was dissolved in DCM (100 ml) and was added acetic anhydride (2.04 g, 20 mmol) followed by TEA (4.04 g, 40 mmol). The mixture was stirred at room temperature for 3 hrs and quenched with saturated NaHCO$_3$. The organic layer was separated and washed with brine. Dried over Na$_2$SO$_4$ and concentrated. The residue was purified on by silica gel column to give the compound of formula (4-2) (10 g). MS: (ESI) m/z (M+H) 1385.8.

Step 49c: Compound of Formula (4-3)

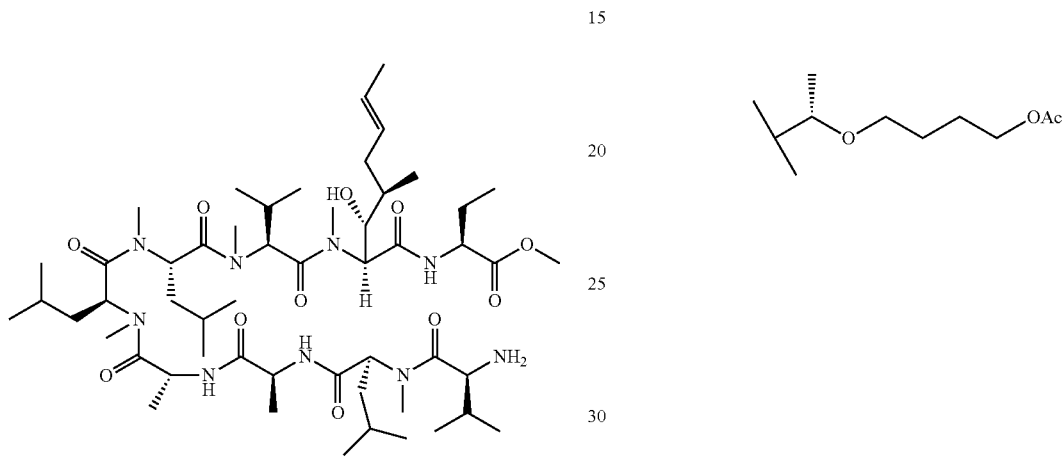

Compound of formula (4-2) (6.9 g, 5 mmole) was dissolved in methanol (50 ml). NaOMe (2N in methanol, 25 ml) was added at room temperature. The reaction mixture was stirred at room temperature for 18 hrs and quenched with saturated NaHCO$_3$. The pH of the mixture was further adjusted to ~9 by adding saturated Na$_2$CO$_3$. Organic layer was separated and washed with brine. Dried over Na$_2$SO$_4$ and the solvent was removed. The residue was purified on by silica gel column to give the compound of formula (4-3) (4.2 g).

MS: (ESI) m/z (M+H) 1036.7.

Step 49d: Compound of Formula (4-5)

To a 250 mL round-bottomed flask were added the compound of formula (4-3) (1.04 g, 1.0 mmol), the compound of formula (4-4), where $R_{11}$ is

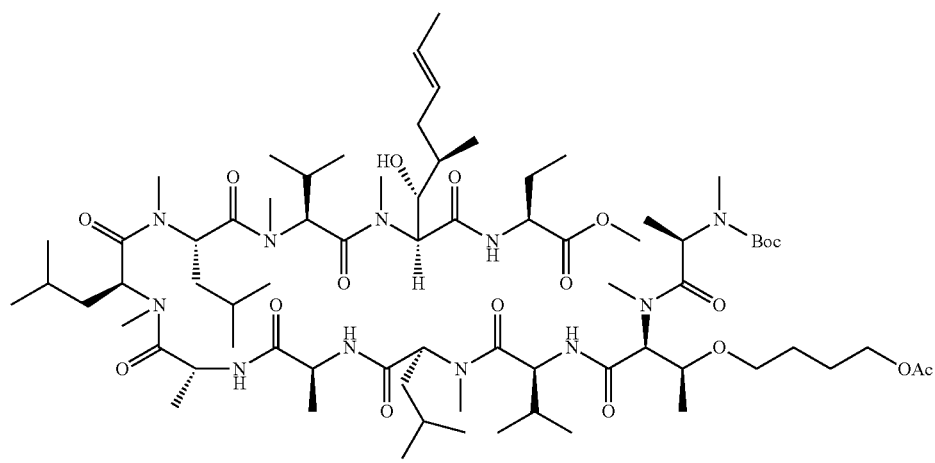 [SMILES: C/C=C/C[C@@H](C)[C@@H](O)[C@@H](C(=O)N[C@@H](CC)C(=O)OC)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)OCCCCOC(C)=O)N(C)C(=O)[C@@H](C)N(C)C(=O)OC(C)(C)C)C(C)C]

(475 mg, 1.1 mmol), CH$_2$Cl$_2$ (20 mL), BOP (531 mg, 1.2 mmol), and DMAP (241.9 mg, 1.98 mmol) respectively. The solution was stirred at room temperature for 16 hrs. Diluted with CH$_2$Cl$_2$, washed with 10% citric acid, water, saturated NaHCO$_3$, brine and dried over Na$_2$SO$_4$. Concentrated and the residue was purified by flash chromatography (MeOH in CH$_2$Cl$_2$, 0~20%, v/v) to afford a white solid 1.4 g.

MS (ESI): 1450.8 m/z (M+1)

Step 49e: Compound of Formula (4-6)

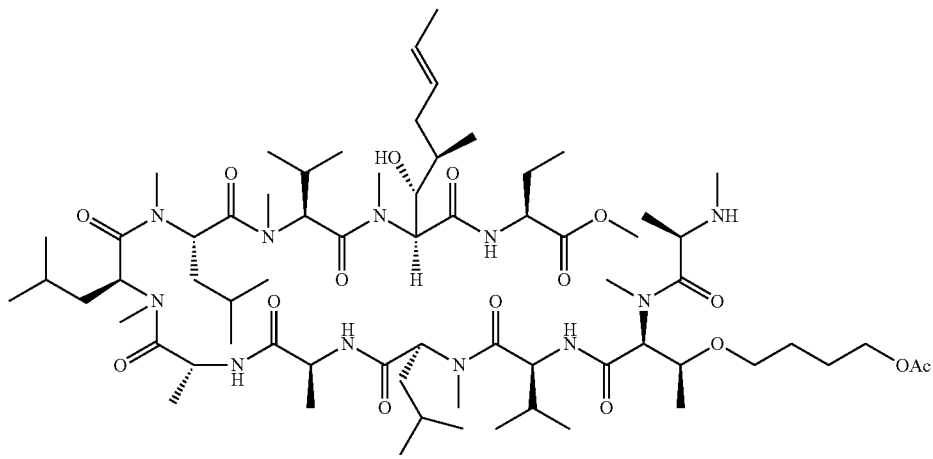 [SMILES: C/C=C/C[C@@H](C)[C@@H](O)[C@@H](C(=O)N[C@@H](CC)C(=O)OC)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)OCCCCOC(C)=O)N(C)C(=O)[C@@H](C)NC)C(C)C]

To a 50 mL round-bottomed flask were added the compound of formula (4-5) (725 mg, 0.50 mmol) from step 2d were added CH$_2$Cl$_2$ (3 mL) and the solution was cooled to 0° C. followed by the addition of TFA (3 mL) dropwise. The reaction mixture was stirred at 0° C. for 2 hrs and the solvents were removed in vacuo and the residue was dissolved in CH$_2$Cl$_2$ (30 mL). Washed with saturated NaHCO$_3$, brine and dried over anhydrous Na$_2$SO$_4$, The solvent was removed and the residue was purified by flash chromatography (MeOH/CH$_2$Cl$_2$, 1-10%, v/v) to give colorless oil 730 mg.

MS (ESI): 1350.8 m/z (M+1)

Step 49f: Compound of Formula (4-7)

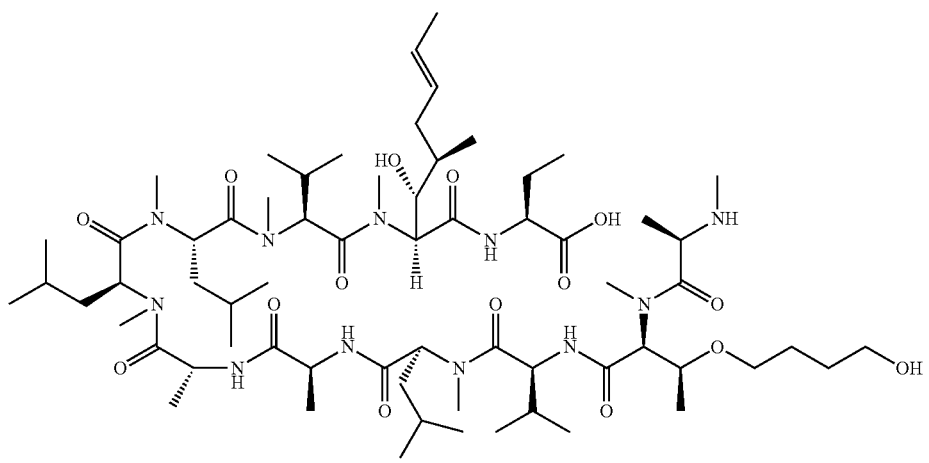 [SMILES: C/C=C/C[C@@H](C)[C@@H](O)[C@@H](C(=O)N[C@@H](CC)C(=O)O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)OCCCCO)N(C)C(=O)[C@@H](C)NC)C(C)C]

To a 50 ml, round-bottomed flask were added the compound from step 2e (675 mg, 0.5 mmol), THF (7 mL) and water (3 mL) respectively and the solution was cooled to 0° C. followed by the addition of lithium hydroxide monohydrate (100 mg, 2.4 mmol). After stirred at 0° C. for 3 h, the reaction mixture was diluted with ethyl acetate (50 ml), washed with 10% citric acid solution, brine and dried over anhydrous Na$_2$SO$_4$. The solvent was removed to give the desired product 650 mg as white foam which was used for next step reaction without further purification.

MS (ESI): 1294.8 m/z (M+1)

Step 49g: Compound of Formula (4-8)

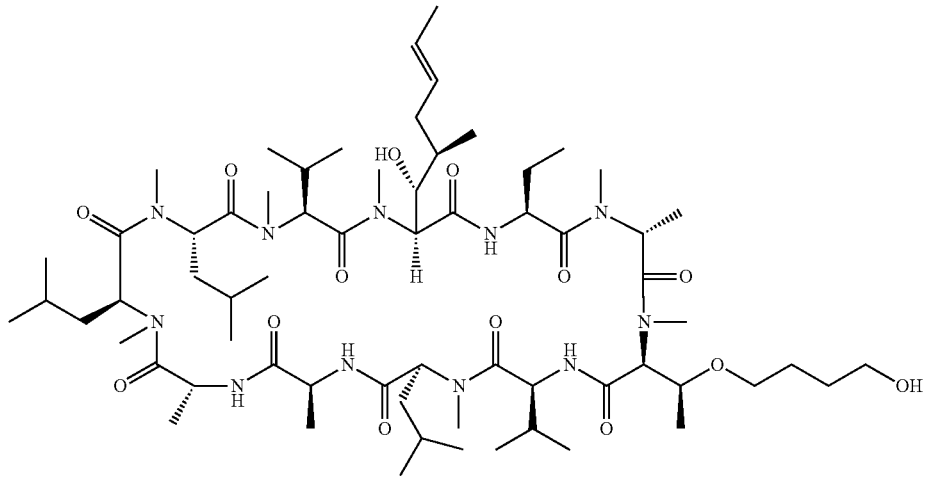 [SMILES: C/C=C/C[C@@H](C)[C@@H](O)[C@H]1C(=O)N[C@@H](CC)C(=O)N(C)[C@H](C)C(=O)N(C)[C@@H]([C@H](C)OCCCCO)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

To a 500 ml round-bottomed flask equipped with a dropping funnel were added BOP (141.5 mg, 0.32 mmol), $CH_2Cl_2$ (250 ml) followed by addition of a solution of DMAP (39.1 mg, 0.32 mmol) and the compound from step 2f (200 mg, 0.16 mmol) in $CH_2Cl_2$ (100 mL) during 2 hrs at room temperature. The solution was stirred at room temperature for 16 hrs. The reaction was quenched with saturated $NaHCO_3$. The organic layer was separated and washed with brine dried over anhydrous $Na_2SO_4$. The solvent was removed and the residue was purified by flash chromatography (MeOH/$CH_2Cl_2$, 1-10%, v/v) to give a white solid 134 mg.

MS (ESI): 1276.9 m/z (M+1)

The compounds of Example 50 to Example 131 were synthesized using the general methods described in Examples 1 to 49.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of producing a compound represented by Formula (4-8):

(4-8)

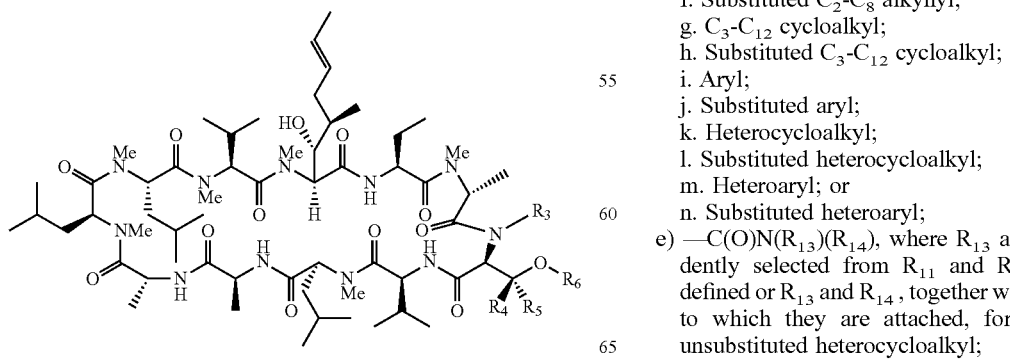

wherein;

$R_4$ and $R_5$ are independently selected from hydrogen, methyl, ethyl, allyl, propyl or isopropyl; and $R_6$ is a) $R_{11}$, where $R_{11}$ is selected from:
1) Hydrogen;
2) Deuterium;
3) $C_1$-$C_8$ alkyl;
4) Substituted $C_1$-$C_8$ alkyl;
5) $C_2$-$C_8$ alkenyl;
6) Substituted $C_2$-$C_8$ alkenyl;
7) $C_2$-$C_8$ alkynyl;
8) Substituted $C_2$-$C_8$ alkynyl;
9) $C_3$-$C_{12}$ cycloalkyl;
10) Substituted $C_3$-$C_{12}$ cycloalkyl;
11) Aryl;
12) Substituted aryl;
13) Heterocycloalkyl;
14) Substituted heterocycloalkyl;
15) Heteroaryl; and
16) Substituted heteroaryl;

b) —C(O)O$R_{11}$, where $R_{11}$ is as previously defined;

c) —C(O) $R_{11}$, where $R_{11}$ is as previously defined;

d) —C(O)OCH$_2$-T-$R_{12}$, where T is —O— or —S— and $R_{12}$ is selected from:
a. $C_1$-$C_8$ alkyl;
b. Substituted $C_1$-$C_8$ alkyl;
c. $C_2$-$C_8$ alkenyl;
d. Substituted $C_2$-$C_8$ alkenyl;
e. $C_2$-$C_8$ alkynyl;
f. Substituted $C_2$-$C_8$ alkynyl;
g. $C_3$-$C_{12}$ cycloalkyl;
h. Substituted $C_3$-$C_{12}$ cycloalkyl;
i. Aryl;
j. Substituted aryl;
k. Heterocycloalkyl;
l. Substituted heterocycloalkyl;
m. Heteroaryl; or
n. Substituted heteroaryl;

e) —C(O)N($R_{13}$)($R_{14}$), where $R_{13}$ and $R_{14}$ are independently selected from $R_{11}$ and $R_{11}$ is as previously defined or $R_{13}$ and $R_{14}$, together with the nitrogen atom to which they are attached, form a substituted or unsubstituted heterocycloalkyl;

f) —C(O)S$R_{11}$, $R_{11}$ is as previously defined;

g) —C(S)O $R_{11}$, where $R_{11}$ is as previously defined;

h) —C(O)OCH$_2$OC(O) R$_{12}$, where R$_{12}$ is as previously defined;

i) —C(S)S R$_{11}$, where R$_{11}$ is as previously defined;

j) R$_{15}$, where R$_{15}$ is selected from:

a. —M—R$_{11}$, where R$_{11}$ is as previously defined and M is selected from:
    i. C$_1$-C$_8$ alkyl;
    ii. Substituted C$_1$-C$_8$ alkyl;
    iii. C$_2$-C$_8$ alkenyl;
    iv. Substituted C$_2$-C$_8$ alkenyl;
    v. C$_2$-C$_8$ alkynyl;
    vi. Substituted C$_2$-C$_8$ alkynyl;
    vii. C$_3$-C$_{12}$ cycloalkyl; and
    viii. Substituted C$_3$-C$_{12}$ cycloalkyl;

b. —M—NR$_{16}$R$_{11}$, where R$_{16}$ is R$_{11}$ or R$_{16}$ and R$_{11}$ together with the nitrogen atom to which they are attached form a substituted or unsubstituted heterocycloalkyl, M is as previously defined;

c. —M—S(O)$_m$R$_{11}$, where m =0, 1,or 2; M and R$_{11}$ are as previously defined;

d. —M—OR$_{11}$, where M and R$_{11}$ are as previously defined;

e. —M—C(O) R$_{11}$, where M and R$_{11}$ are as previously defined;

f. —M—OC(O) R$_{12}$, where M and R$_{12}$ are as previously defined;

g. —M—OC(O)O R$_{12}$, where M and R$_{12}$ are as previously defined;

h. —M—NR$_{17}$C(O) R$_{12}$, where R$_{17}$ is R$_{11}$, M and R$_{12}$ are as previously defined;

i. —MNR$_{17}$C(O)O R$_{12}$, where R$_{17}$, M and R$_{12}$ are as previously defined;

j. —M—C(O)NR$_{16}$ R$_{11}$, where R$_{16}$, M and R$_{11}$ are as previously defined;

k. —M—C(O)N(R$_{16}$)—OR$_{11}$, where R$_{16}$, M and R$_{11}$ are as previously defined;

l. —M—OC(O)NR$_{16}$ R$_{11}$, where R$_{16}$, M and R$_{11}$ are as previously defined;

m. —M—NR$_{17}$C(O)NR$_{16}$ R$_{11}$, where M, R$_{11}$, R$_{16}$ are as previously defined or R$_{16}$ and R$_{11}$ together with the nitrogen atom to which they are attached form a substituted or unsubstituted heterocycloalkyl;

n. —M—C(S)S R$_{11}$, where M and R$_{11}$ are as previously defined;

o. —M—OC(S)S R$_{12}$, where M and R$_{12}$ are as previously defined;

p. —M—NR$_{17}$C(O)S R$_{12}$, where M, R$_{17}$ and R$_{12}$ are as previously defined;

q. —M—SC(O)NR$_{16}$ R$_{11}$, where M, R$_{11}$ and R$_{16}$ are as previously defined or R$_{16}$ and R$_{11}$ together with the nitrogen atom to which they are attached form a substituted or unsubstituted heterocycloalkyl;

r. —M—CH=N—O R$_{11}$, where M and R$_{11}$ are as previously defined;

s. —M—CH=N—NR$_{16}$ R$_{11}$ R$_{16}$ are as previously defined or R$_{16}$ and R$_{11}$ together with the nitrogen atom to which they are attached form a substituted or unsubstituted heterocycloalkyl;

said method comprising the steps of:

(1) reacting a compound of Formula 1-3,

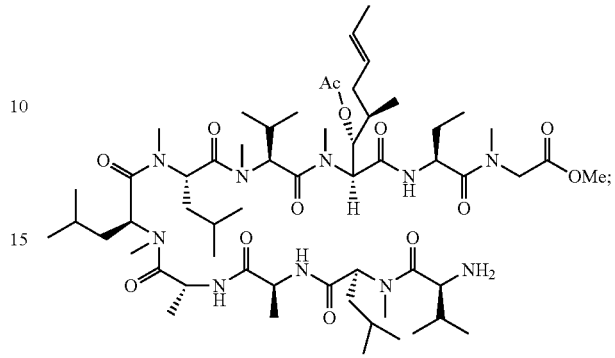

(1-3)

with a reducing agent in a protic solvent;

(2) reacting the product of step (1) with Fmoc-Cl in an aprotic solvent in the presence of an organic base to produce a compound of Formula (4-1),

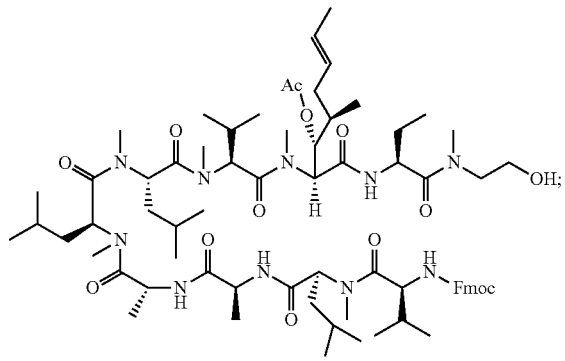

(4-1)

(3) contacting the compound of Formula (4-1) with an acid in a protic solvent;

(4) reacting the product of step (3) with acetic anhydride in an aprotic solvent in the presence of a base, thereby producing a compound of Formula (4-2),

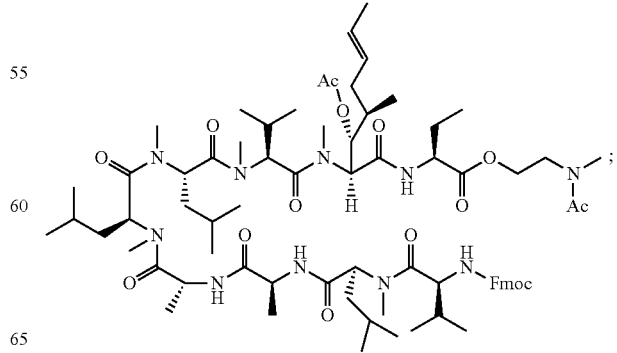

(4-2)

(5) reacting the compound of Formula (4-2) with sodium methoxide in methanol to produce a compound of Formula (4-3).
(6) reacting the compound of Formula (4-3) with a compound of Formula (4-4),
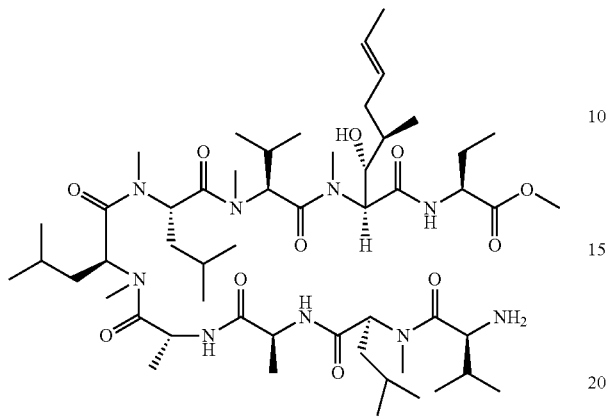
(4-3)
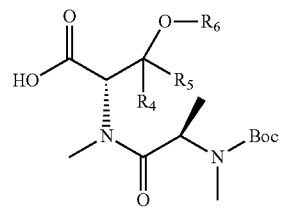
(4-4)
in an aprotic solvent in the presence of a coupling reagent and a base to produce a compound of Formula (4-5),
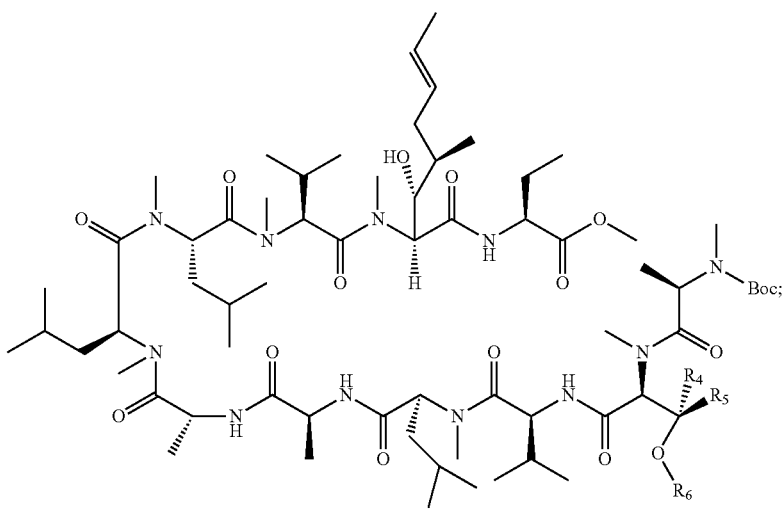
(4-5)
(7) reacting the compound of Formula (4-5) with an acid to produce a compound of Formula (4-6),
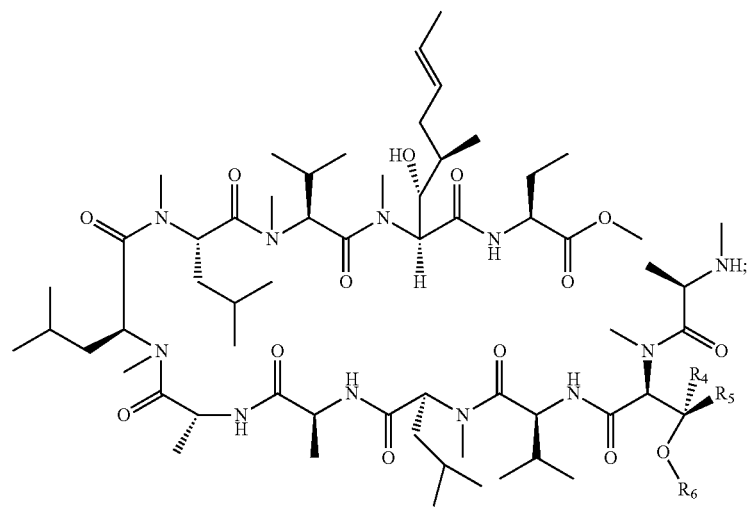
(4-6)

(8) reacting the compound of Formula (4-6) with alkali in a protic solvent to produce a compound of Formula (4-7), (4-7)

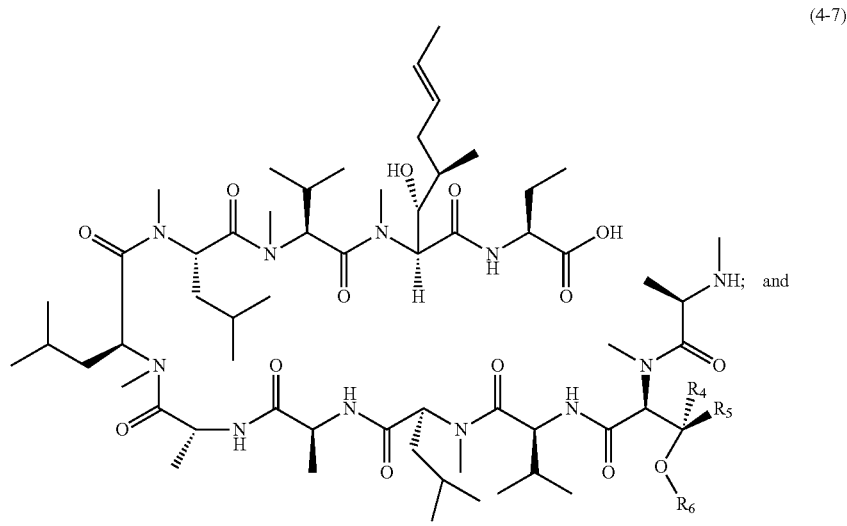

(9) reacting the compound of Formula (4-7) with a coupling reagent and a base in an aprotic solvent, thereby producing the compound of Formula (4-8).

2. The method of claim 1, wherein $R_4$ and $R_5$ are each independently hydrogen or methyl.

3. The method of claim 2, wherein $R_4$ is hydrogen and $R_5$ is methyl.

4. The method of claim 3, wherein $R_6$ is selected from the group set forth below:

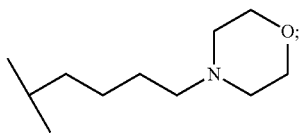

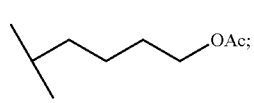

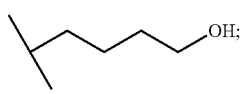

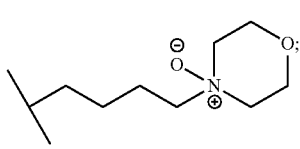

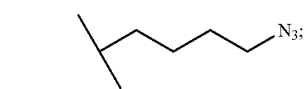

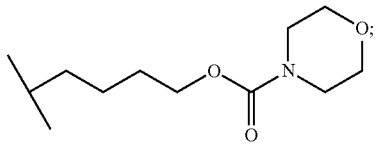 [SMILES: CC(C)CCCCOC(=O)N1CCOCC1]

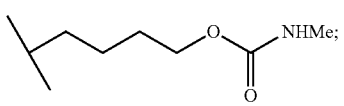

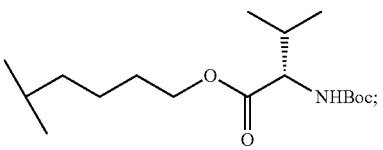

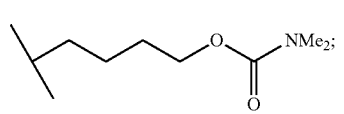

143 144
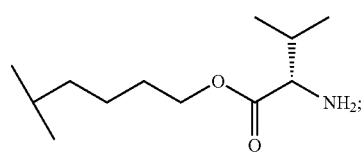
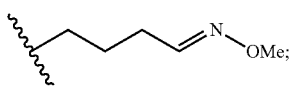
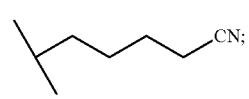
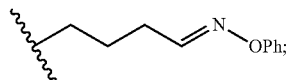
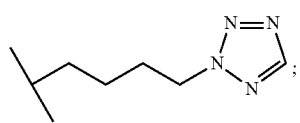
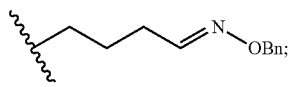
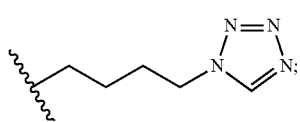 [SMILES: *CCCCn1cnnn1]
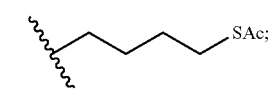
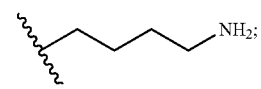 [SMILES: *CCCCN]
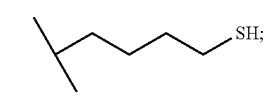
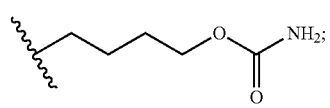 [SMILES: *CCCCOC(N)=O]
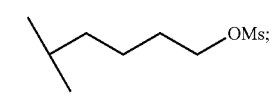
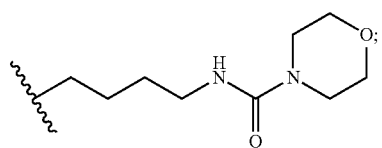 [SMILES: *CCCCNC(=O)N1CCOCC1]
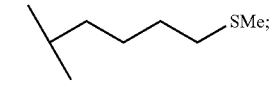
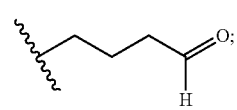 [SMILES: *CCCC=O]
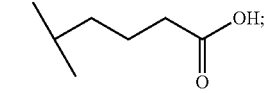
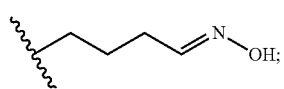 [SMILES: *CCC/C=N/O]
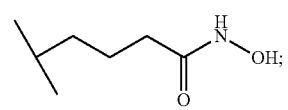
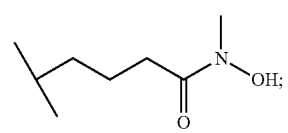

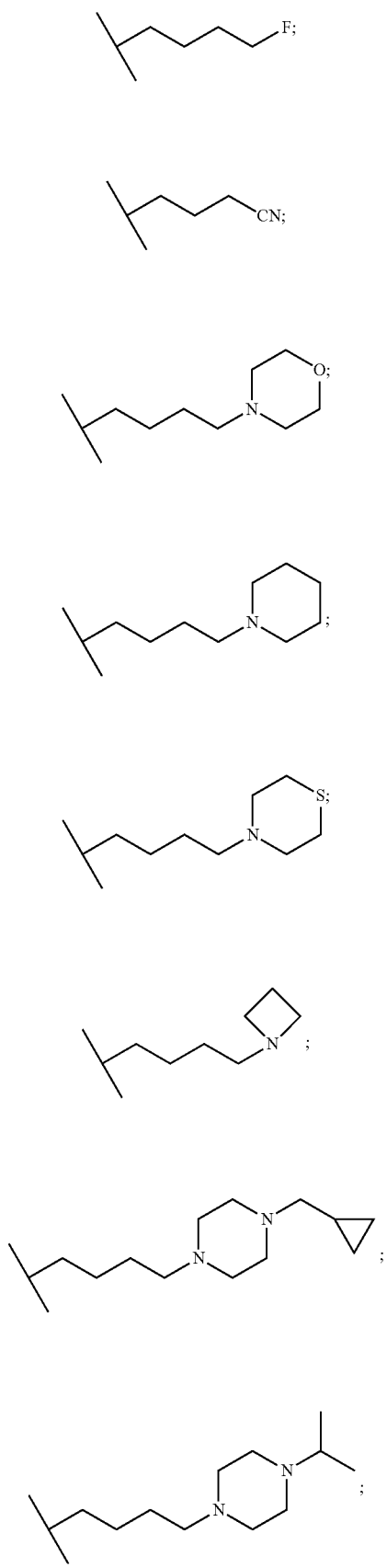
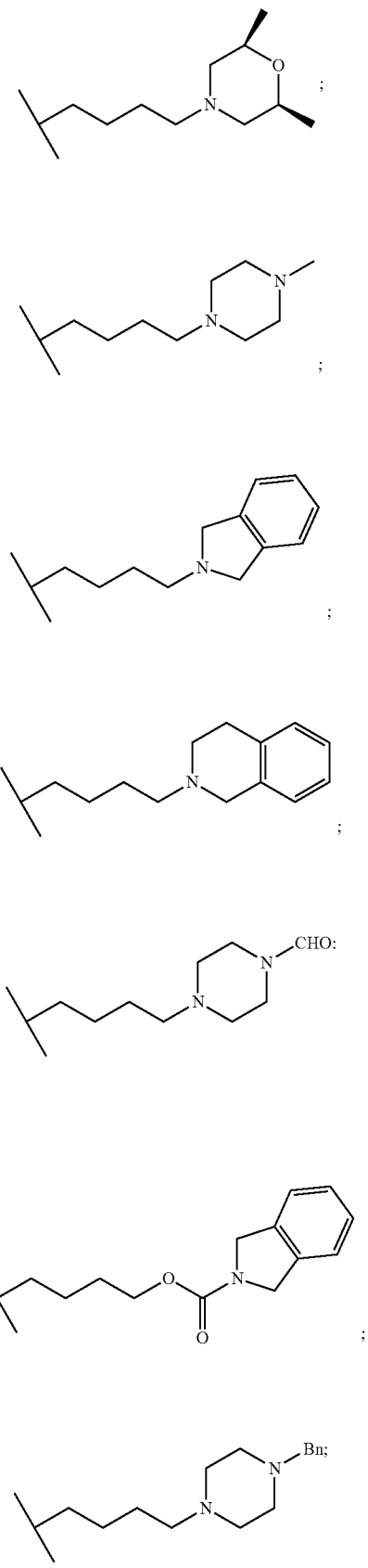

| 147 | 148 |
|---|---|
| 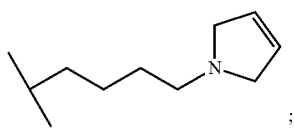 | 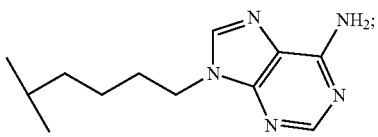 |
| 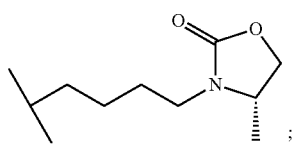 | 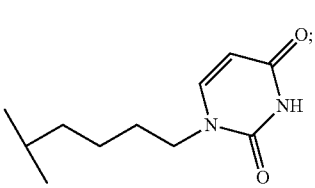 |
| 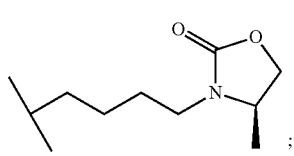 | 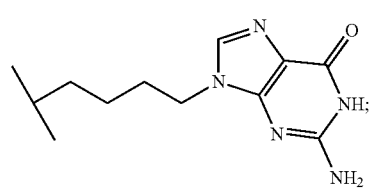 |
| 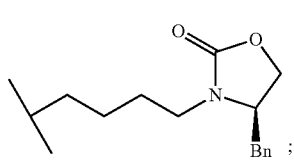 [SMILES: CC(C)CCCCN1C(=O)OC[C@H]1Cc1ccccc1] | 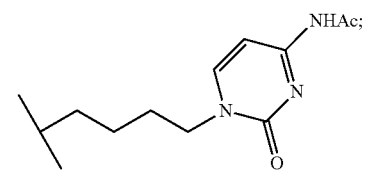 |
| 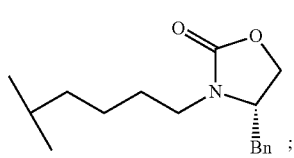 [SMILES: CC(C)CCCCN1C(=O)OC[C@@H]1Cc1ccccc1] | 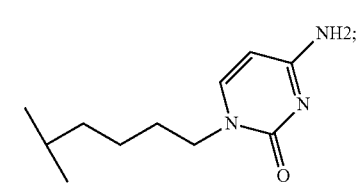 |
| 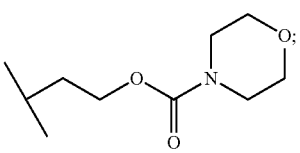 | 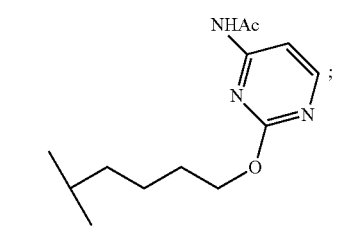 [SMILES: CC(=O)Nc1ccnc(OCCCCC(C)C)n1] |
| 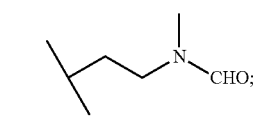 | |
| 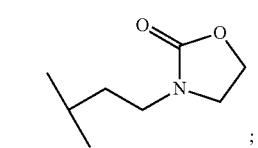 | |

149
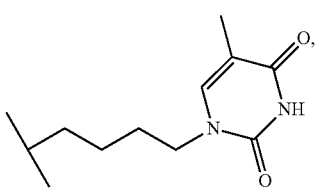 [SMILES: Cc1cn(CCCCC(C)C)c(=O)[nH]c1=O]
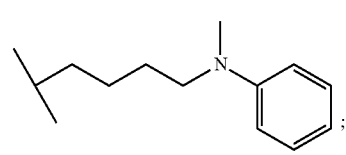
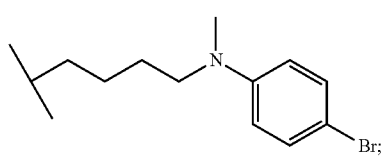 [SMILES: CC(C)CCCCN(C)c1ccc(Br)cc1]
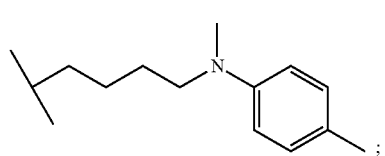 [SMILES: Cc1ccc(N(C)CCCCC(C)C)cc1]
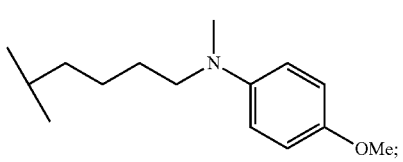 [SMILES: COc1ccc(N(C)CCCCC(C)C)cc1]
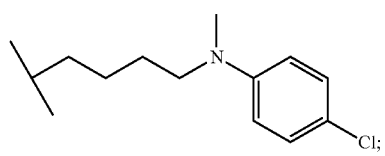 [SMILES: CC(C)CCCCN(C)c1ccc(Cl)cc1]
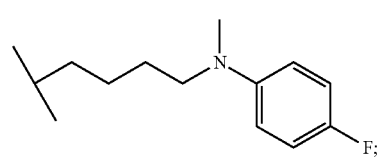 [SMILES: CC(C)CCCCN(C)c1ccc(F)cc1]
150
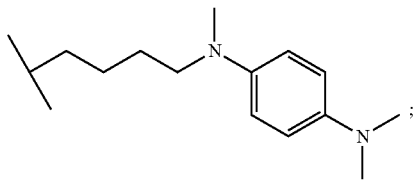 [SMILES: CC(C)CCCCN(C)c1ccc(N(C)C)cc1]
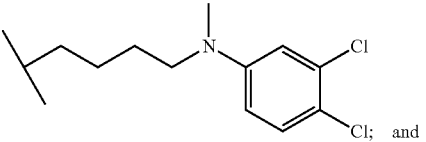 [SMILES: CC(C)CCCCN(C)c1ccc(Cl)c(Cl)c1] and
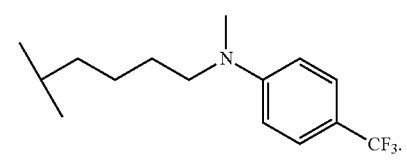
5. The method of claim 3, wherein $R_6$ is selected from the group set forth below:
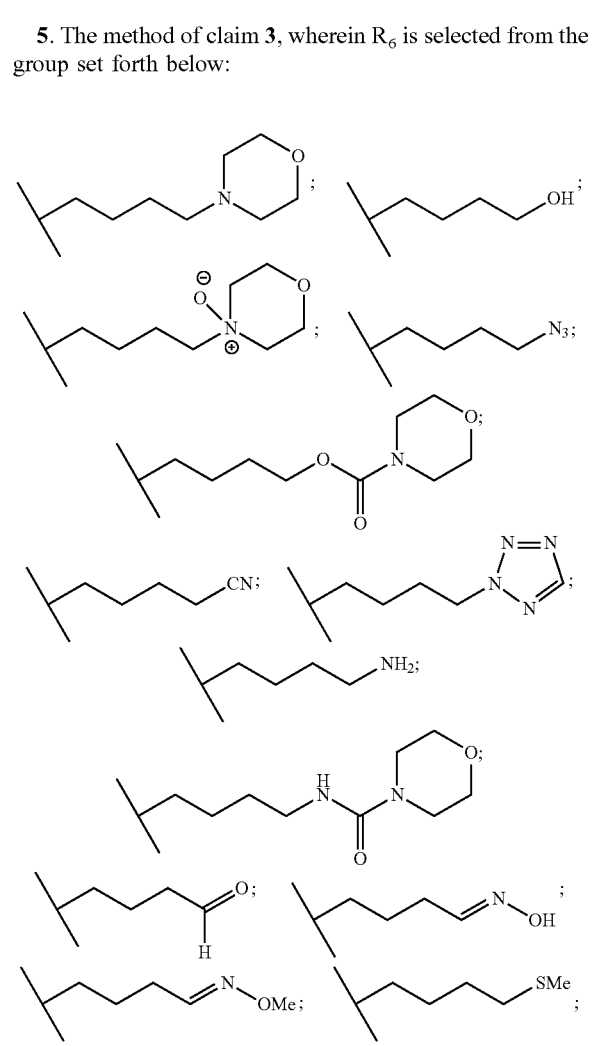

-continued

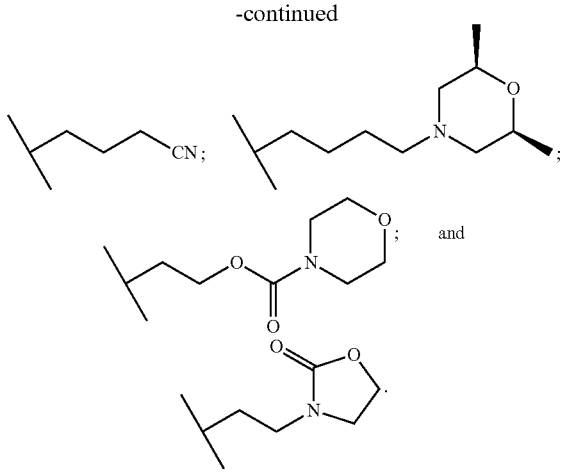

6. The method of claim 3, wherein R₆ is

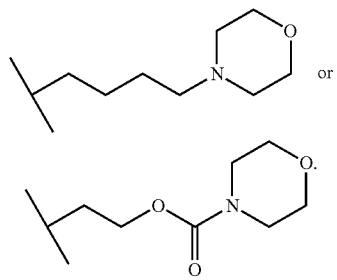

7. The method of claim 3, wherein R₆ is is allyl;

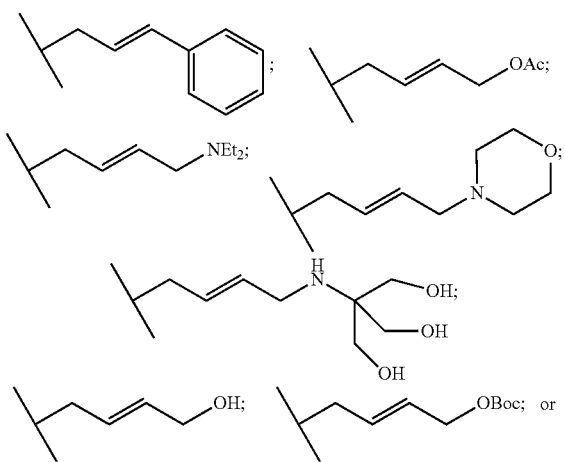

-continued

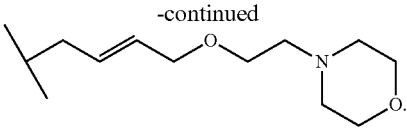

8. The method of claim 3, wherein R₆ is

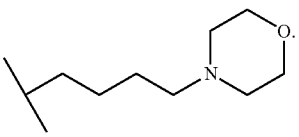

9. The method of claim 1, wherein in step (1), the reducing agent is NaBH4 and the protic solvent is selected from methanol, ethanol, isopropanol, tert-butanol or a mixture of any two thereof.

10. The method of claim 1, wherein in step (2) the organic base is triethylamine, diisopropylamine, 1,8-diazabicyclo[5.4.0]undec-7-ene, N-methylmorpholine or 4-dimethylaminopyridine and the aprotic solvent is dichloromethane, N,N-dimethylformamide or tetrahydrofuran.

11. The method of claim 1, wherein in step (3) the acid is methanesulfonic acid, toluenesulfonic acid or camphorsulfonic acid and the protic solvent is methanol, ethanol, isopropanol or tert-butanol.

12. The method of claim 1, wherein in step (4), the base is trimethylamine, diisopropylamine, 1,8-diazabicyclo[5.4.0]undec-7-ene, N-methylmorpholine or 4dimethylaminopyridine and the aprotic solvent is dichloromethane, 1,2-dichloroethane, N,N-dimethylformamide or tetrahydrofuran.

13. The method of claim 1, wherein in step (6) the aprotic solvent is dichloromethane, N,N-dimethylformamide or tetrahydrofuran, the coupling agent is N,N'-dicyclohexylcarbodiimide, N-(3-dimethylaminopropyl)-N'-ethylcarbodiimide, di-isopropyl carbodiimide, BOP—Cl, PyBOP, PyAOP, TFFH and HATU and the base is triethylamine, diisopropylethylamine, 1,8-diazabicyclo[5.4.0]undec-7-ene, N-methylmorpholine or 4-dimethylaminopyridine.

14. The method of claim 1, wherein in step (7) the acid is TFA, HC1 in dioxane or methanesulfonic acid.

15. The method of claim 1, wherein in claim (8) the alkali is lithium hydroxide, sodium hydroxide, potassium hydroxide.

16. The method of claim 1, wherein in step (9) the aprotic solvent is dichloromethane, N,N-dimethylformamide or tetrahydrofuran, the coupling agent is N,N'-dicyclohexylcarbodiimide, N-(3-dimethylaminopropyl)-N'-ethylcarbodiimide, di-isopropyl carbodiimide, BOP—Cl, PyBOP, PyAOP, TFFH and HATU and the base is triethylamine, diisopropylethylamine, 1,8-diazabicyclo[5.4.0]undec-7-ene, N-methylmorpholine or 4-dimethylaminopyridine.

* * * * *